US012371467B2

(12) United States Patent
Klebanoff et al.

(10) Patent No.: US 12,371,467 B2
(45) Date of Patent: Jul. 29, 2025

(54) T CELL RECEPTORS TARGETING PIK3CA MUTATIONS AND USES THEREOF

(71) Applicant: MEMORIAL SLOAN-KETTERING CANCER CENTER, New York, NY (US)

(72) Inventors: Christopher A. Klebanoff, New York, NY (US); Smita S. Chandran, Long Island City, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 1126 days.

(21) Appl. No.: 17/095,288

(22) Filed: Nov. 11, 2020

(65) Prior Publication Data

US 2021/0060076 A1 Mar. 4, 2021

Related U.S. Application Data

(63) Continuation of application No. PCT/US2019/031749, filed on May 10, 2019.

(60) Provisional application No. 62/688,066, filed on Jun. 21, 2018, provisional application No. 62/670,407, filed on May 11, 2018.

(51) Int. Cl.
| | |
|---|---|
| *C07K 14/725* | (2006.01) |
| *A61K 40/11* | (2025.01) |
| *A61K 40/32* | (2025.01) |
| *A61K 40/42* | (2025.01) |
| *A61K 40/50* | (2025.01) |

(52) U.S. Cl.
CPC ........ *C07K 14/7051* (2013.01); *A61K 40/11* (2025.01); *A61K 40/32* (2025.01); *A61K 40/4251* (2025.01); *A61K 40/4269* (2025.01); *A61K 40/4272* (2025.01); *A61K 40/50* (2025.01); *A61K 2239/49* (2023.05); *C07K 2319/03* (2013.01)

(58) Field of Classification Search
None
See application file for complete search history.

(56) References Cited

U.S. PATENT DOCUMENTS

| | | | |
|---|---|---|---|
| 5,399,346 A | 3/1995 | Anderson et al. | |
| 5,595,756 A * | 1/1997 | Bally ............... | A61K 9/1272 |
| | | | 264/4.1 |
| 2004/0209363 A1 | 10/2004 | Watts et al. | |
| 2013/0121960 A1 | 5/2013 | Sadelain et al. | |
| 2013/0295063 A1 | 11/2013 | Jakobsen et al. | |
| 2014/0212446 A1 | 7/2014 | Riley et al. | |

FOREIGN PATENT DOCUMENTS

| | | | |
|---|---|---|---|
| CN | 102174576 A | 9/2011 | |
| EP | 3 173 474 A1 | 5/2017 | |
| WO | WO 2008/059252 A2 | 5/2008 | |
| WO | WO 2008/060510 A2 | 5/2008 | |
| WO | WO 2009/146179 A1 | 12/2009 | |
| WO | WO 2013/163628 A2 | 10/2013 | |
| WO | WO 2014/040370 A1 | 3/2014 | |
| WO | WO 2014/093661 A2 | 6/2014 | |
| WO | WO 2014/134412 A1 | 9/2014 | |
| WO | WO 2014/160030 A2 | 10/2014 | |
| WO | WO 2015/071763 A2 | 5/2015 | |
| WO | WO 2015/089354 A1 | 6/2015 | |
| WO | WO 2015/123339 A1 | 8/2015 | |
| WO | WO 2016/146618 A1 | 9/2016 | |
| WO | WO-2016187508 A2 * | 11/2016 | ............ A61K 38/00 |
| WO | WO 2017/120428 A2 | 7/2017 | |
| WO | WO 2017/173321 A1 | 10/2017 | |
| WO | WO 2018/057447 A1 | 3/2018 | |
| WO | WO 2019/217831 A1 | 11/2019 | |

OTHER PUBLICATIONS

Bonovas et al (Anticancer Research. 28: 1857-1866 (2008)) (Year: 2008).*
Sporn et al, "Chemoprevention of Cancer," Carcinogenesis, vol. 21 (2000), 525-530 (Year: 2000).*
Auerbach et al (Cancer and Metastasis Reviews, 2000, 19: 167-172) (Year: 2000).*
Gura T (Science, 1997, 278(5340): 1041-1042, encloses 1-5) (Year: 1997).*
HogenEsch et al (J Control Release. Dec. 10, 2012; 164(2): 183-186.) (Year: 2012).*
Hait (Nature Reviews/Drug Discovery, 2010, 9, pp. 253-254) (Year: 2010).*
Gravanis et al. (Chin Clin Oncol, 2014, 3, pp. 1-5) (Year: 2014).*
Beans (PNAS 2018; 115(50): 12539-12543) (Year: 2018).*
Jain RK (Scientific American, Jul. 1994,58-65) (Year: 1994).*
Mankoo et al (Proteins. May 1, 2009; 75(2): 499-508) (Year: 2009).*
Iiizumi et al., "Identification of Novel HLA Class II-Restricted Neoantigens Derived from Driver Mutations," Cancers, 11:266 (2019) 14 pgs.
Mackay et al., "Molecular determinants of outcome with mammalian target of rapamycin inhibition in endometrial cancer," Cancer, 120:603-610 (2014).

(Continued)

*Primary Examiner* — Brian Gangle
*Assistant Examiner* — Andrea K McCollum
(74) *Attorney, Agent, or Firm* — Baker Botts L.L.P.

(57) ABSTRACT

The presently disclosed subject matter provides for methods and compositions for treating cancer (e.g., breast cancer). It relates to mutant phosphatidylinositol-4,5-bisphosphate 3-kinase catalytic subunit alpha (PIK3CA)-targeted T cell receptors (TCRs) that specifically target a mutant PIK3CA peptide (e.g., a human mutant PIK3CA peptide), and immunoresponsive cells comprising such TCRs. The presently disclosed mutant PIK3CA peptide-specific TCRs have enhanced immune-activating properties, including anti-tumor activity.

28 Claims, 32 Drawing Sheets

Specification includes a Sequence Listing.

(56) References Cited

OTHER PUBLICATIONS

Supplementary Partial European Search Report dated Jun. 14, 2022 in Application No. EP 19800639.
Arimoto-Miyamoto et al., "Optimal stimulation for CD70 induction on human monocyte-derived dendritic cells and the importance of CD70 in naive CD4+ T-cell differentiation," Immunology 130:137-149 (2010).
Extended European Search Report dated Aug. 2, 2022 in Application No. EP 19799471.
Gilboa, "Knocking the SOCS1 off dendritic cells," Nature Biotechnology 22(12):1521-1522 (2004).
Extended European Search Report dated Oct. 11, 2023 in Application No. EP 23167921.
Abhinandan et al., "Analysis and improvements to Kabat and structurally correct numbering of antibody variable domains," Mol. Immunol. 45:3832-3839 (2008).
Altschul et al., "Gapped BLAST and PSI-BLAST: a new generation of protein database search programs," Nucleic Acids Res. 25(17):3389-3402 (1997).
Anderson, "Prospects for Human Gene Therapy," Science 226:401-409 (1984).
Benton et al., "Screening kgt Recombinant Clones by Hybridization to Single Plaques in situ," Science 196:180 (1977).
Blomer et al., "Highly Efficient and Sustained Gene Transfer in Adult Neurons with a Lentivirus Vector," Journal of Virology 71:6641-6649 (1997).
Bregni, et al., "Human Peripheral Blood Hematopoietic Progenitors Are Optimal Targets of Retroviral-Mediated Gene Transfer," Blood 80(6):1418-1422 (1992).
Brigham et al., "Rapid Communication: In vivo Transfection of Murine Lungs with a Functioning Prokaryotic Gene Using a Liposome Vehicle," Am. J. Med. Sci. 298(4):278-281 (1989).
Cayouette et al., "Adenovirus-Mediated Gene Transfer of Ciliary Neurotrophic Factor Can Prevent Photoreceptor Degeneration in the Retinal Degeneration (rd) Mouse," Human Gene Therapy 8:423-430 (1997).
Chothia et al., "Canonical Structures for the Hypervariable Regions of Immunoglobulins," J. Mol. Biol. 196:901-917 (1987).
Cohen et al., "Enhanced Antitumor Activity of Murine-Human Hybrid T-Cell Receptor (TCR) in Human Lymphocytes is Associated with Improved Pairing and TCR/CD3, Stability," Cancer Res. 66(17):8878-8886 (2006).
Cohen et al., "Enhanced Antitumor Activity of T cells Engineered to Express T-cell Receptors with a Second Disulfide Bond," Cancer Res. 67(8):3898-3903 (2007).
Cornetta et al., "Gene Transfer into Primates and Prospects for Gene Therapy in Humans," Nucleic Acid Research and Molecular Biology 36:311-322 (1987).
Danos et al., "Safe and efficient generation of recombinant retroviruses with amphotropic and ecotropic host ranges," Proc. Natl. Acad. Sci. USA 85:6460-6464 (1988).
Dupont et al., "Artificial Antigen-Presenting Cells Transduced with Telomerase Efficiently Expand Epitope-Specific, Human Leukocyte Antigen-Restricted Cytotoxic T Cells," Cancer Res 65:5417-5427 (2005).
Eglitis et al., "Retroviral Vectors for Introduction of Genes into Mammalian Cells," Bio-Techniques 6(7):608-614 (1988).
Fang et al., "Cartilage-reactive T cells in rheumatoid synovium," International Immunology, 12(5):659-669 (2000).
Felgner et al., "Lipofection: A highly efficient, lipid-mediated DNA-transfection procedure," Proc. Natl. Acad. Sci. U.S.A. 84:7413-7417 (1987).
Friedmann, "Progress toward Human Gene Therapy," Science 244:1275-1281 (1989).
Grunstein et al., "Colony hybridization: A method for the isolation of cloned DNAs that contain a specific gene," Proc. Natl Acad. Sci., USA 72:3961-3965 (1975).
Haga-Friedman et al., "Incorporation of Transmembrane Hydrophobic Mutations in the TCR Enhance Its Surface Expression and T Cell Functional Avidity," Journal of Immunology 188:5538-5546 (2012).
Hughes et al., "Retroviral Gene Transfer to Primitive Normal and Leukemic Hematopoietic Cells Using Clinically Applicable Procedures," J. Clin. Invest. 89:1817-1824 (1992).
International Search Report mailed Aug. 29, 2019 in International Application No. PCT/US19/31743.
International Search Report mailed Aug. 30, 2019 in International Application No. PCT/US19/31749.
Johnson, "Gene Therapy for Cystic Fibrosis," Chest 107:77S-83S (1995).
Kido et al., "Use of a retroviral vector with an internal opsin promoter to direct gene expression to retinal photoreceptor cells," Current Eye Research 15:833-844 (1996).
Kimmel, "Identification and Characterization of Specific Clones: Strategy for Confirming the Validity of Presumptive Clones," Methods Enzymol. 152:507-511 (1987).
Kuball et al., "Facilitating matched pairing and expression of TCR chains introduced into human T cells," Blood 109:2331-2338 (2007).
Le Gal La Salle et al., "An Adenovirus Vector for Gene Transfer into Neurons and Glia in the Brain," Science 259:988-990 (1993).
Miller et al., "Generation of Helper-Free Amphotropic Retroviruses That Transduce a Dominant-Acting, Methotrexate-Resistant Dihydrofolate Reductase Gene," Mol. Cell. Biol. 5(3):431-437 (1985).
Miller et al., "Improved Retroviral Vectors for Gene Transfer and Expression," Biotechniques 7:980-990 (1989).
Miller et al., "Redesign of Retrovirus Packaging Cell Lines to Avoid Recombination Leading to Helper Virus Production," Mol. Cell. Biol. 6(8):2895-2902 (1986).
Miller, "Retrovirus Packaging Cells," Human Gene Therapy 1:5-14 (1990).
Millis et al., "Landscape of Phosphatidylinositol-3-Kinase Pathway Alterations Across 19 784 Diverse Solid Tumors," JAMA Oncol. 2(12):1565-1573 (2016).
Miyoshi et al., "Stable and efficient gene transfer into the retina using an HIV-based lentiviral vector," Proc. Natl. Acad. Sci. U.S.A. 94:10319-10323 (1997).
Moen, "Directions in Gene Therapy," Blood Cells 17:407-416 (1991).
Morgan et al., "Cancer Regression in Patients After Transfer of Genetically Engineered Lymphocytes," Science 314:126-129 (2006).
Myers et al., "Optimal alignments in linear space," CABIOS 4:11-17 (1988).
Naldini et al., "In Vivo Gene Delivery and Stable Transduction of Nondividing Cells by a Lentiviral Vector," Science 272:263-267 (1996).
Needleman et al., "A General Method Applicable to the Search for Similarities in the Amino Acid Sequence of Two Proteins," J Mol. Biol. 48:443-453 (1970).
Ono et al., "Plasmid DNAs directly injected into mouse brain with lipofectin can be incorporated and expressed by brain cells," Neuroscience Letters 117:259-263 (1990).
Panelli et al., "A Tumor-Infiltrating Lymphocyte from a Melanoma Metastasis with Decreased Expression of Melanoma Differentiation Antigens Recognizes MAGE-12," J Immunol 164:4382-4392 (2000).
Panelli et al., "Expansion of Tumor-T Cell Pairs from Fine Needle Aspirates of Melanoma Metastases," J Immunol 164:495-504 (2000).
Papanicolaou et al., "Rapid expansion of cytomegalovirus-specific cytotoxic T lymphocytes by artificial antigen-presenting cells expressing a single HLA allele," Blood 102:2498-2505 (2003).
Partial Supplementary European Search Report dated Mar. 24, 2022 in Application No. EP 19799471.
Ping et al., "T-cell receptor-engineered T cells for cancer treatment: current status and future directions," Protein Cell March 9(3):254-266 (2018).
Rosenberg et al., "Gene Transfer into Humans—Immunotherapy of Patients with Advanced Melanoma, Using Tumor-Infiltrating Lymphocytes Modified By Retroviral Gene Transduction," N. Engl. J Med 323:570-578 (1990).

(56) References Cited

OTHER PUBLICATIONS

Sadelain et al., "Targeting Tumours With Genetically Enhanced T Lymphocytes," Nat Rev Cancer 3:35-45 (2003).
Shao et al., "Identification of peptide-specific TCR genes by in vitro peptide stimulation and CDR3 length polymorphism analysis," Cancer Letters, 363:83-91 (2015).
Sharp, "Gene Therapy," The Lancet 337:1277-1278 (1991).
Straubinger et al., "Liposomes as Carriers for Intracellular Delivery of Nucleic Acids," Methods in Enzymology 101:512-527 (1983).
Tolstoshev et al., "Gene expression using retroviral vectors," Current Opinion in Biotechnology 1:55-61 (1990).
Wahl et al., "Molecular Hybridization of Immobilized Nucleic Acids: Theoretical Concepts and Practical Considerations," Methods Enzymol. 152:399-407 (1987).
Wolff et al., "Direct Gene Transfer into Mouse Muscle in Vivo," Science 247:1465-1468 (1990).
Wu et al., "Receptor-mediated Gene Delivery and Expression in Vivo," Journal of Biological Chemistry 263:14621-14624 (1988).
Wu et al., "Targeting Genes: Delivery and Persistent Expression of a Foreign Gene Driven by Mammalian Regulatory Elements in Vivo," Journal of Biological Chemistry 264:16985-16987 (1989).
Xu et al., "Correction of the enzyme deficiency in hemapoietic cells of Gaucher patients using a clinically acceptable retroviral supernatant transduction protocol," Exp. Hemat. 22:223-230 (1994).
Afik et al., "Targeted reconstruction of T cell receptor sequence from single cell RNA-seq links CDR3 length to T cell differentiation state," Nucleic Acids Research, 45(16):e148 (2017) 13 pgs.
Linnemann et al., "High-throughput identification of antigen-specific TCRS by TCR gene capture," Nature Medicine, 19:1534-1541 (2013).
Munks et al., "4-1BB and OX40 stimulation enhance CD8 and CD4 T-cell responses to a DNA prime, poxvirus boost vaccine," Immunology 112(4):559-566 (2004).
Sohn et al., "Development of a qPCR method to rapidly assess the function of NKT cells," J Immunol Methods 407:82-89 (2014).
Altschul et al., "Basic Local Alignment Search Tool," J. Mol. Biol. 215:403-410 (1990).
U.S. Appl. No. 17/095,216, Feb. 13, 2025 Non-Final Office Action.
Grunebach et al., "Cotransfection of dendritic cells with RNA coding for HER-2/neu and 4-1BBL increases the induction of tumor antigen specific cytotoxic T lymphocytes," Cancer Gene Therapy 12:749-756 (2005).
Youlin et al., "Anti-tumor immune response induced by dendritic cells transduced with truncated PSMA IRES 4-1BBL recombinant adenovirus," Cancer Letters 293:254-262 (2010).

\* cited by examiner

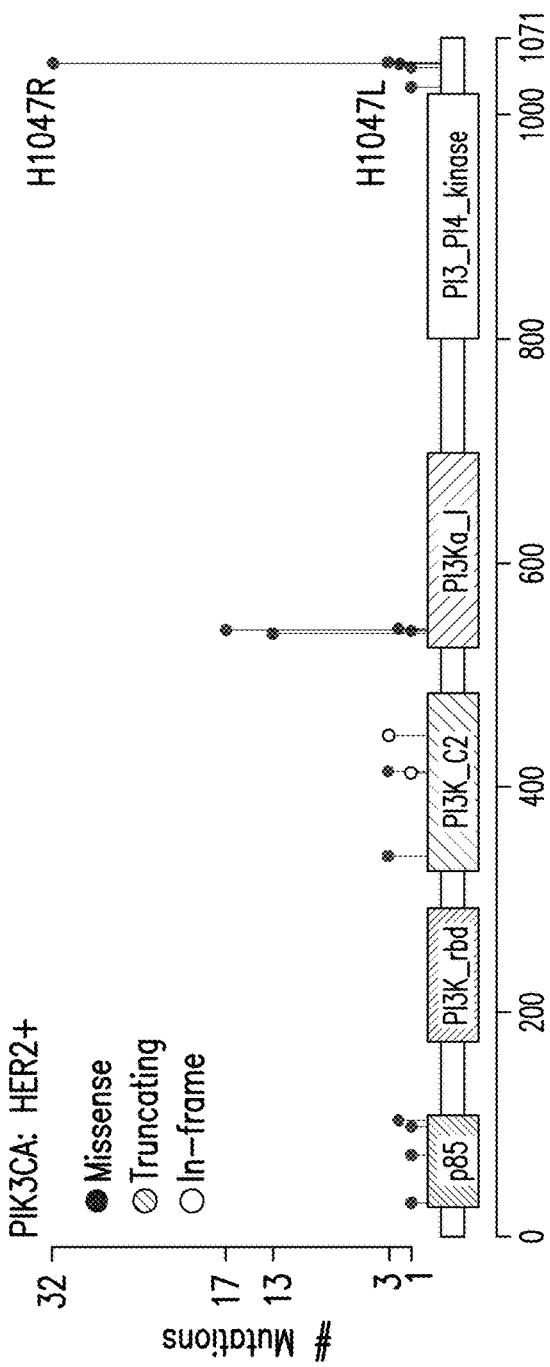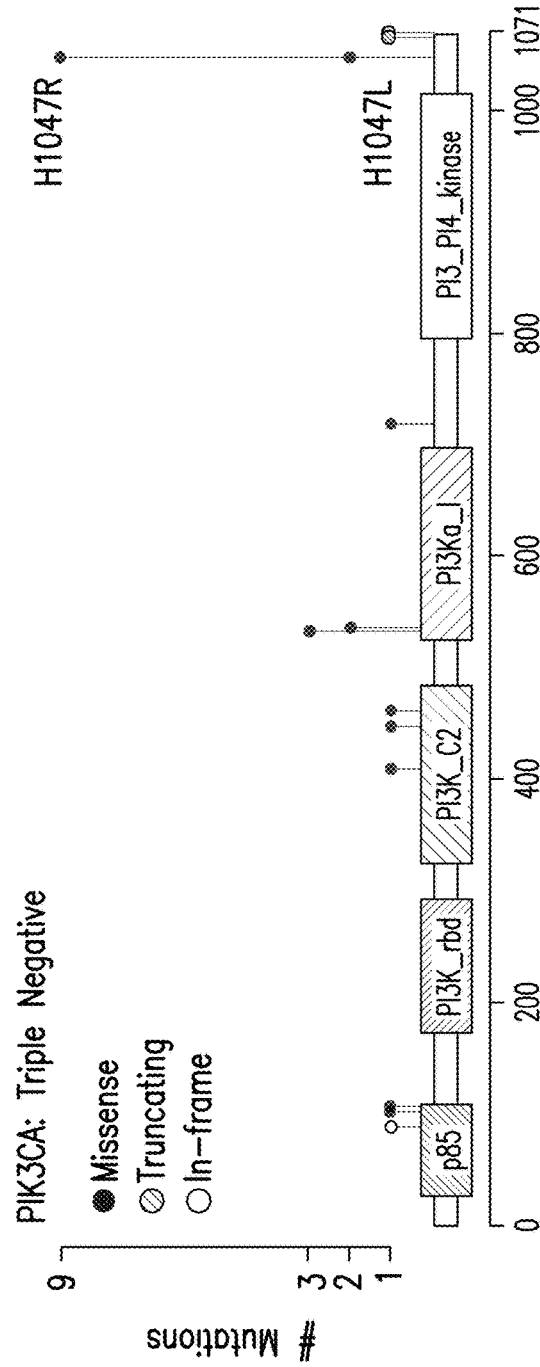
FIG. 2

Stimulation and screening constructs for mPIK3CA

PIK3CA hot spot mutations
c. 1624G>A (E542K)
c. 1633G>A (E545K)
c. 3140A>G (H1047R)/(H1047L)

542E-RE-MART-MAGE
haglsnrlardnelrendkeqlkaistrdplseiteqekdflwshrhycvtipeilpklllsvkw 542E2K-RE-MART-MAGE
haglsnrlardnelrendkeqlkaistrdplskiteqekdflwshrhycvtipeilpklllsvkw 545E-RE-MART-MAGE
lsnrlardnelrendkeqlkaistrdplseiteqekdflwshrhycvtipeilpklllsvkwnsr 545E2K-RE-MART-MAGE
lsnrlardnelrendkeqlkaistrdplseitkqekdflwshrhycvtipeilpklllsvkwnsr 1047H-RE-MART-MAGE
ktlaldkteqealeyfmkqmndahhggwttkmdwifhtikqhaln 1047H2R-RE-MART-MAGE
ktlaldkteqealeyfmkqmndarhggwttkmdwifhtikqhaln 1047H2L-RE-MART-MAGE
ktlaldkteqealeyfmkqmndalhggwttkmdwifhtikqhaln RE' = restriction enzyme digest site.

MART-1/A2:01 (modified):
ghsyttaeelagigiltvilgvlll
MAGE-A3 DPB04:
ILGDPKKLLTQHFVQENYLEYRQVP
} MHC Class I and class II restricted transfection controls

FIG. 8

| Clonotype | Frequency of reads | Proportion | CDR3: Alpha | CDR3: Beta | Comments |
|---|---|---|---|---|---|
| 1 | 22 | 0.45 | CAVRPLYGGSYIPTF | CASSYVGNTGELFF | 1G4 TCR |
| 2 | 22 | 0.45 | CAVNFGGGKLIF | CASSLSFGTEAFF | F5 TCR |
| 3 | 6 | 0.12 | | CASSRMNTEAFF | |
| 4 | 4 | 0.08 | | CASSYFQGAAEAFF | |
| 5 | 3 | 0.06 | CVLGGGSARQLTF | CASSPKQQYEQYF | |
| 6 | 3 | 0.06 | | CASSFTTGVGTEAFF | |
| 7 | 3 | 0.06 | | CASRKQNYGYTF | |
| 8 | 3 | 0.06 | | CASSENGGVDEQFF | |
| 9 | 3 | 0.06 | | CASSSAFTGTEDPGYTF | |
| 10 | 2 | 0.04 | CAVNKRSNYQLIW | CASSEWTSGDNEQFF | |
| 11 | 2 | 0.04 | CWNDGTYKYIF | | |
| 12 | 2 | 0.04 | CAASMIARLMF | CASSLGITFSIDIQYF | |
| 13 | 2 | 0.04 | CAMRDFSGGYNKLIF | | |
| 14 | 2 | 0.04 | CAGHPLNDMRF | CASSQGRGEYEAFF | |
| 15 | 2 | 0.04 | CAFVRNNNARLMF | | |
| 16 | 2 | 0.04 | CAESLMDTGRRALTF | | |
| 17 | 2 | 0.04 | | CASSPGYEQFF | |
| 18 | 2 | 0.04 | | CASSHPLGGQGNTWGNEQFF | |
| 19 | 2 | 0.04 | | CASSFSGTGAFF | |
| 20 | 2 | 0.04 | | CASSPTGTSGNEQYF | |
| 21 | 2 | 0.04 | | CASSEGHLNTEAFF | |
| 22 | 2 | 0.04 | | CASSRVQNEQFF | |
| 23 | 2 | 0.04 | | CASSFSGTPPQPQHF | |
| 24 | 2 | 0.04 | | CASSLQGYNEQFF | |
| 25 | 2 | 0.04 | | CASSIPGKETQYF | |
| 26 | 2 | 0.04 | | CASSTTLTGIKDTF | |
| 27 | 2 | 0.04 | | CASSYGLTYEQYF | |
| 28 | 2 | 0.04 | | CASSSLGDVMNTEAFF | |
| 29 | 2 | 0.04 | | CASSRGLQPTQYF | |
| 30 | 2 | 0.04 | | CASSFNPSYEQYF | |

- Estimated Number of Cells: 4875
- Total Number of Clonotypes: 1599
- Top 30 clonotypes shown here.
- Increase sequencing depth would increase productive α/β pairing for rare populations.

▨ = unpaired TCR α or β sequence.

FIG. 13

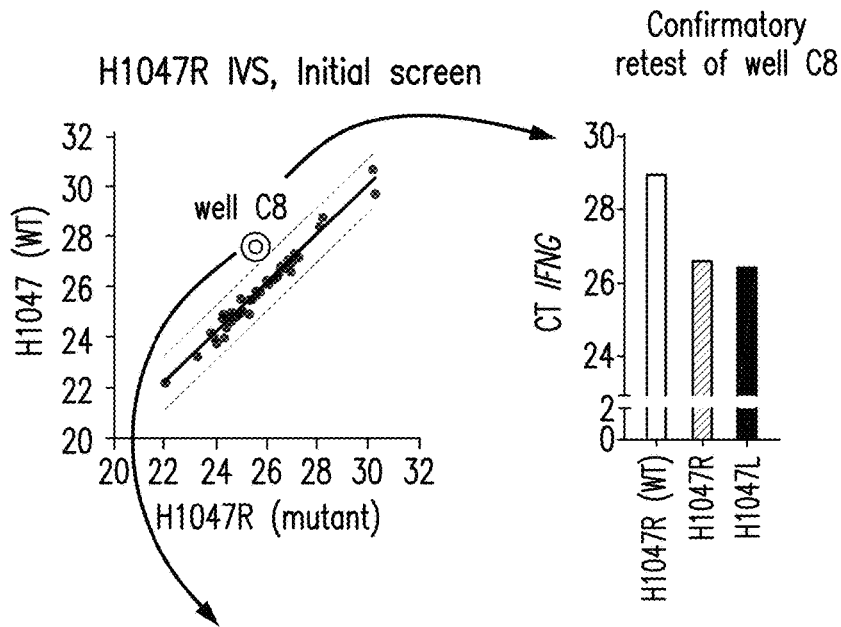

| RC8: Top 10 Clonotype CDR3 Sequences | | | | |
|---|---|---|---|---|
| Clonotype ID | CDR3s | Frequency | Proportion | |
| clonotype1 | TRA:CAVKGSDDYKLSF<br>TRB:CASSPVNLAGVSRADTQYF | 56 | 17.80% | 37.20% |
| clonotype2 | TRB:CASSPRGYQPQHF | 44 | 14.00% | 21.60% |
| clonotype3 | TRB:CASSPVNLAGVSRADTQYF | 37 | 11.80% | |
| clonotype4 | TRA:CAVKGSDDYKLSF | 24 | 7.60% | |
| clonotype5 | TRA:CAVTSWGKLQF<br>TRB:CASSPRGYQPQHF | 18 | 5.70% | |
| clonotype8 | TRB:CASSPPEAGLDTEAFF | 6 | 1.90% | 2.90% |
| clonotype7 | TRB:CASSLSGGGDYGYTF | 6 | 1.90% | |
| clonotype6 | TRA:CAVTSWGKLQF | 6 | 1.90% | |
| clonotype9 | TRA:CASGGSGNTGKLIF<br>TRB:CASSLGQFNYEQYF | 3 | 1.00% | |
| clonotype10 | TRA:CAMREVLDNTDKLIF<br>TRB:CASSPPEAGLDTEAFF | 3 | 1.00% | 1.00% |
| | | 203 | 64.60% | 62.70% |

Just 4 clones make up 62.7% of well C8 following IVS × 3 stims.

FIG. 14

RC8 top 3 clonotypes

1. TRBV18*01, TRBD2*02, TRJ2-3*01
   TRAV21*02, TRAJ20*01
   (Frequency: 51.1%)

CDR3 Beta: CASSPVNLAGVSRADTQYF
   CDR3 Alpha: CAVKGSDDYKLSF

MDTRVLCCAVICLLGAGLSNAGVMQNPRHLVRRRGQEARLRCSPMKGHSHVYWYRQLPEEGLKFMVYLQKENIIDESGMPKE
   RFSAEFPKEGPSILRIQQVVRGDSAAYFCASSPVNLAGVSRADTQYFGPGTRLTVLEDLRNVTPPKVSLFEPSKAEIANKQKATLV
   CLARGFFPDHVELSWWVNGKEVHSGVCTDPQAYKESNYSYCLSSRLRVSATFWHNPRNHFRCQVQFHGLSEEDKWPEGSPK
   PVTQNISAEAWGRADCGITSASYQQGVLSATILYEILLGKATLYAVLVSTLVVMAMVKRKNSRAKRSGSGATNFSLLKQAGDVEE
   NPGPMETLLGLLILWLQLQWVSSKQEVTQIPAALSVPEGENLVLNCSFTDSAIYNLQWFRQDPGKGLTSLLLIQSSQREQTSGRL
   NASLDKSSGRSTLYIAASQPGDSATYLCAVKGSDDYKLSFGAGTTVTVRANIQNPEPAVYQLKDPRSQDSTLCLFTDFDSQINVP
   KTMESGTFITDKCVLDMKAMDSKSNGAIAWSNQTSFTCQDIFKETNATYPSSDVPCDATLTEKSFETDMNLNFQNLLVIVLRILLL
   KVAGFNLLMTLRLWSS

2. TRBV7-2*02, TRBD1*01, TRBJ1-5*01
   TRAV1-2*01, TRAJ24*02
   (Frequency: 29.7%)

CDR3 Beta: CASSPRGYQPQHF
   CDR3 Alpha: CAVTSWGKLQF

MGTRLLFWVAFCLLGAYHTGAGVSQSPSNKVTEKGKDVELRCDPISGHTALYWYRQRLGQGLEFLIYFQGNSAPDKSGLPSDR
   FSAERTGESVSTLTIQRTQQEDSAVYLCASSPRGYQPQHFGDGTRLSILEDLRNVTPPKVSLFEPSKAEIANKQKATLVCLARGFF
   PDHVELSWWVNGKEVHSGVCTDPQAYKESNYSYCLSSRLRVSATFWHNPRNHFRCQVQFHGLSEEDKWPEGSPKPVTQNIS
   AEAWGRADCGITSASYQQGVLSATILYEILLGKATLYAVLVSTLVVMAMVKRKNSRAKRSGSGATNFSLLKQAGDVEENPGPMW
   GVFLLYVSMKMGGTTGQNIDQPTEMTATEGAIVQINCTYQTSGFNGLFWYQQHAGEAPTFLSYNVLDGLEEKGRFSSFLSRSK
   GYSYLLLKELQMKDSASYLCAVTSWGKLQFKLQFGAGTQVVVTPNIQNPEPAVYQLKDPRSQDSTLCLFTDFDSQINVPKTMES
   GTFITDKCVLDMKAMDSKSNGAIAWSNQTSFTCQDIFKETNATYPSSDVPCDATLTEKSFETDMNLNFQNLLVIVLRILLLKVAGFN
   LLMTLRLWSS

FIG. 17

3. TRVB18, TRBD2, TRBJ1-1TRAV14DV4*02, TRAJ34
   (Frequency: 4.8%)

CDR3 Beta: CASSPPEAGLDTEAFF
   CDR3 Alpha: CAMREVLDNTDKLIF

MDTRVLCCAVICLLGAGLSNAGVMQNPRHLVRRRGQEARLRCSPMKGHSHVYWYRQLPEEGLKFMVYLQKENIIDESGMP
KERFSAEFPKEGPSILRIQQVVRGDSAAYFCASSPPEAGLDTEAFFGQGTRLTVVEDLRNVTPPKVSLFEPSKAEIANKQKAT
LVCLARGFFPDHVELSWWVNGKEVHSGVCTDPQAYKESNYSYCLSSRLRVSATFWHNPRNHFRCQVQFHGLSEEDKWPE
GSPKPVTQNISAEAWGRADCGITSASYQQGVLSATILYEILLGKATLYAVLVSTLVVMAMVKRKNSRAKRSGSGATNFSLLKQ
AGDVEENPGPMSLSSLLKVVTASLWLGPGIAQKITQTQPGMFVQEKEAVTLDCTYDTSDQSYGLFWYKQP
SSGEMIFLIYQGSYDEQNATEGRYSLNFQKARKSANLVISASQLGDSAMYFCAMREVLDNTDKLIFGTGTRLQVFPNIQNPEP
AVYQLKDPRSQDSTLCLFTDFDSQINVPKTMESGTFITDKCVLDMKAMDSKSNGAIAWSNQTSFTCQDIFKETNATYPSSDVP
CDATLTEKSFETDMNLNFQNLLVIVLRILLLKVAGFNLLMTLRLWSS

LB11 top 4 clonotypes

1. TRBV20-1*02, TRBD1*01, TRBJ2-7*01
   TRAV12-3*01, TRAJ13*01
   (Frequency: 39.6%)

CDR3 Beta: CSAREQGPLEEQYF
   CDR3 Alpha: CAMNSGGYQKVTF

MLLLLLLLGPAGSGLGAVVSQHPSRVICKSGTSVKIECRSLDFQATTMFWYRQFPKQSLM
LMATSNEGSKATYEQGVEKDKFLINHASLTLSTLTVTSAHPEDSSFYICSACSAREQGPLEEQYFGPGTRLTVTEDLRNVTPPKVS
LFEPSKAEIANKQKATLVCLARGFFPDHVELSWWVNGKEVHSGVCTDPQAYKESNYSYCLSSRLRVSATFWHNPRNHFRCQVQ
FHGLSEEDKWPEGSPKPVTQNISAEAWGRADCGITSASYQQGVLSATILYEILLGKATLYAVLVSTLVVMAMVKRKNSRAKRSGS
GATNFSLLKQAGDVEENPGPMMKSLRVLLVILWLQLSWVWSQQKEVEQDGPLSVPEGAIVSLNCTYSNSAFQYFMWYRQYS
RKGPELLMYTYSSGNKEDGRFTAQVDKSSKYISLFIRDSQPSDSATYLCAMNSGGYQKVTFGIGTKLQVIPNIQNPEPAVYQLKDP
RSQDSTLCLFTDFDSQINVPKTMESGTFITDKCVLDMKAMDSKSNGAIAWSNQTSFTCQDIFKETNATYPSSDVPCDATLTEKSFE
TDMNLNFQNLLVIVLRILLLKVAGFNLLMTLRLWSS

FIG. 17 continued

2. TRBV5-6*01, TRD1*01, TRJ2-7*01 (other variant is identical)
   TRAV26-1*02, TRAJ22*01
   (Frequency: 28.5%)

CDR3 Beta: CASSFGTATYEQYF
   CDR3 Alpha: CIVRVAGSARQLTF

MGPGLLCWALLCLLGAGLVDAGVTQSPTHLIKTRGQQVTLRCSPKSGHDTVSWYQQALGQGPQFIFQYYEEEERQRGNFPDRF
SGHQFPNYSSELNVNALLLGDSALYLCASSFGTATYEQYFGPGTRLTVTEDLRNVTPPKVSLFEPSKAEIANKQKATLVCLARGFF
PDHVELSWWVNGKEVHSGVCTDPQAYKESNYSYCLSSRLRVSATFWHNPRNHFRCQVQFHGLSEEDKWPEGSPKPVTQNISA
EAWGRADCGITSASYQQGVLSATILYEILLGKATLYAVLVSTLVVMAMVKRKNSRAKRSGSGATNFSLLKQAGDVEENPGPMRLVA
RVTVFLTFGTIIDAKTTQPPSMDCAEGRAANLPCNHSTISGNEYVYWYRQIHSQGPQYIIHGLKNNETNEMASLIITEDRKSSTLILP
HATLRDTAVYYCIVRVAGSARQLTFGSGTQLTVLPNIQNPEPAVYQLKDPRSQDSTLCLFTDFDSQINVPKTMESGTFITDKCVLDM
KAMDSKSNGAIAWSNQTSFTCQDIFKETNATYPSSDVPCDATLTEKSFETDMNLNFQNLLVIVLRILLLKVAGFNLLMTLRLWSS

3. TRBV27*01, TRBD1*01, TRBJ1-2*01
   TRAV13-1*01, TRAJ44*01
   (Frequency: 15.6%)

CDR3 Beta: CASSPYRQGSYGYTF
   CDR3 Alpha: CAASIPGTASKLTF

MGPQLLGYVVLCLLGAGPLEAQVTQNPRYLITVTGKKLTVTCSQNMNHEYMSWYRQDPGLGLRQIYYSMNVEVTDKGDV
PEGYKVSRKEKRNFPLILESPSPNQTSLYFCASSPYRQGSYGYTFGSGTRLTVVEDLRNVTPPKVSLFEPSKAEIANKQKATLVCL
ARGFFPDHVELSWWVNGKEVHSGVCTDPQAYKESNYSYCLSSRLRVSATFWHNPRNHFRCQVQFHGLSEEDKWPEGSPKPV
TQNISAEAWGRADCGITSASYQQGVLSATILYEILLGKATLYAVLVSTLVVMAMVKRKNSRAKRSGSGATNFSLLKQAGDVEENPG
PMTSIRAVFIFLWLQLDLVNGENVEQHPSTLSVQEGDSAVIKCTYSDSASNYFPWYKQELGKGPQLIIDIRSNVGEKKDQRIAVTLN
KTAKHFSLHITETQPEDSAVYFCAASIPGTASKLTFGTGTRLQVTLNIQNPEPAVYQLKDPRSQDSTLCLFTDFDSQINVPKTMESG
TFITDKCVLDMKAMDSKSNGAIAWSNQTSFTCQDIFKETNATYPSSDVPCDATLTEKSFETDMNLNFQNLLVIVLRILLLKVAGFNLL
MTLRLWSS

Note: The TRAV family has been identified as TRAV13-1*02 based on the 10X sequencing data. However, IMGT does not carry information for TRAV13-1*02, so the sequence for TRAV13-1*01 has been used instead.

FIG. 17 continued

4. TRBV12-3*01, TRBD1*01, TRBJ1-1*01
   TRAV23DV6*01, TRAJ21*01
   (Frequency: 2.9%)

CDR3 Beta: CASNRQGTVTEAFF
   CDR3 Alpha: CAASTGNFNKFYF

MDSWTFCCVSLCILVAKHTDAGVIQSPRHEVTEMGQEVTLRCKPISGHNSLFWYRQTMMRGLELLIYFNNNVPIDDSGMP
   EDRFSAKMPNASFSTLKIQPSEPRDSAVYFCASNRQGTVTEAFFGQGTRLTVVEDLRNVTPPKVSLFEPSKAEIANKQKATLVCLA
   RGFFPDHVELSWWVNGKEVHSGVCTDPQAYKESNYSYCLSSRLRVSATFWHNPRNHFRCQVQFHGLSEEDKWPEGSPKPVT
   QNISAEAWGRADCGITSASYQQGVLSATILYEILLGKATLYAVLVSTLVVMAMVKRKNSRAKRSGSGATNFSLLKQAGDVEENPGP
   MDKILGASFLVLWLQLCWVSGQQKEKSDQQQVKQSPQSLIVQKGGISIINCAYENTAFDYFPWYQQFPGKGPALLIAIRPDVSEKK
   EGRFTISFNKSAKQFSLHIMDSQPGDSATYFCAASTGNFNKFYFGSGTKLNVKPNIQNPEPAVYQLKDPRSQDSTLCLFTDFDSQI
   NVPKTMESGTFITDKCVLDMKAMDSKSNGAIAWSNQTSFTCQDIFKETNATYPSSDVPCDATLTEKSFETDMNLNFQNLLVIVLRIL
   LLKVAGFNLLMTLRLWSS

FIG. 17 continued

Summary of PIK3CA mutation-specific TCR discovery pipeline

| Donor | Bulk culture reactivity | Clone ID, reactivity |
|---|---|---|
| 1 | Pooled H1047 mutants | #2, H1047L only |
| 1 | Pooled H1047 mutants | #10, H1047L only |
| 1 | Pooled H1047 mutants | #13, H1047, R and L |
| 3 | H1047L only | NA |
| 3 | H1047, R and L | NA |

Donor #1: blood type = A/B+, HLA = A3+, class II = DRB1*11:04:01 (2.3%), 15:01:01 (15.9%) DRB3*02:02:01 (in progress), DRB5*01:01:01 (in progress), DQB1*06:02:01 (15.5%), 06:03:01 (4.6%), DPB1*04:01:01 (65%)

Donor #3: blood type = A−, HLA = A3+, remaining loci TBD.

FIG. 18

T CELL RECEPTORS TARGETING PIK3CA MUTATIONS AND USES THEREOF

CROSS-REFERENCE TO RELATED APPLICATIONS

This application is a continuation of International Application No. PCT/US2019/031749, filed May 10, 2019, which claims priority to U.S. Provisional Application No. 62/670,407 filed May 11, 2018, and to U.S. Provisional Application No. 62/688,066 filed Jun. 21, 2018, the contents of each of which are incorporated by reference in their entireties herein, and to each of which priority is claimed.

SEQUENCE LISTING

The specification further incorporates by reference the Sequence Listing submitted herewith via EFS on Nov. 11, 2020. Pursuant to 37 C.F.R. § 1.52(e)(5), the Sequence Listing text file, identified as 072734_0872CON_SL.txt, is 123,243 bytes and was created on Nov. 11, 2020. The Sequence Listing, electronically filed herewith, does not extend beyond the scope of the specification and thus does not contain new matter.

INTRODUCTION

The presently disclosed subject matter provides methods and compositions for treating cancer (e.g., breast cancer). It relates to T cell receptors (TCRs) that specifically target phosphatidylinositol-4,5-bisphosphate 3-kinase catalytic subunit alpha (PIK3CA) that comprises a mutation. The presently disclosed subject matter further provides immunoresponsive cells comprising such TCRs, and methods of using such TCRs and such cells for treating any human PIK3CA-mutated cancers, including but not limited to, breast cancer, endometrial cancer, cervical cancer, anal cancer, bladder cancer, colorectal cancer, head and neck squamous cell carcinoma, nonmelanoma skin cancer and salivary gland cancer.

BACKGROUND OF THE INVENTION

Cell-based immunotherapy is a therapy with curative potential for the treatment of cancer. T cells and other immune cells may be modified to target tumor antigens through the introduction of genetic material coding for TCRs specific to selected antigens. Targeted T cell therapy using specific TCRs has shown recent clinical success in treating hematologic malignancies.

A third of breast cancer patients carry PIK3CA mutations, where location of hotspot mutations in PIK3CA are similar across breast cancer subtypes. Furthermore, PIK3CA has only a limited number of hotspot mutations conserved across patients in breast cancer. These features make targeting specific mutations of PIK3CA a promising strategy for targeting and eliminating breast cancer cells. Accordingly, there are needs for novel therapeutic strategies to identify and generate TCRs targeting PIK3CA comprising mutations, and for strategies capable of inducing potent cancer eradication with minimal toxicity and immunogenicity.

SUMMARY OF THE INVENTION

The presently disclosed subject matter generally provides a T cell receptor (TCR) specifically targeting a PIK3CA peptide, wherein the PIK3CA peptide comprises a mutation. In certain embodiments, the mutation is selected from the group consisting of H104R, E545K, E542K, N345K, H1047L, E726K, C420R and any combination thereof. In certain embodiments, the mutation is H1047R or H1047L.

In certain embodiments, the TCR comprises an extracellular domain, a transmembrane domain and an intracellular domain, wherein the extracellular domain binds to the PIK3CA peptide. In certain embodiments, the extracellular domain comprises:

a) an α chain variable region CDR3 comprising the amino acid sequence set forth in SEQ ID NO: 3 or a conservative modification thereof, and a β chain variable region CDR3 comprising the amino acid sequence set forth in SEQ ID NO: 6 or a conservative modification thereof;

b) an α chain variable region CDR3 comprising the amino acid sequence set forth in SEQ ID NO: 13 or a conservative modification thereof, and a β chain variable region CDR3 comprising the amino acid sequence set forth in SEQ ID NO: 16 or a conservative modification thereof;

c) an α chain variable region CDR3 comprising the amino acid sequence set forth in SEQ ID NO: 23 or a conservative modification thereof, and a β chain variable region CDR3 comprising the amino acid sequence set forth in SEQ ID NO: 26 or a conservative modification thereof;

d) an α chain variable region CDR3 comprising the amino acid sequence set forth in SEQ ID NO: 33 or a conservative modification thereof, and a β chain variable region CDR3 comprising the amino acid sequence set forth in SEQ ID NO: 36 or a conservative modification thereof;

e) an α chain variable region CDR3 comprising the amino acid sequence set forth in SEQ ID NO: 43 or a conservative modification thereof, and a β chain variable region CDR3 comprising the amino acid sequence set forth in SEQ ID NO: 46 or a conservative modification thereof;

f) an α chain variable region CDR3 comprising the amino acid sequence set forth in SEQ ID NO: 53 or a conservative modification thereof, and a β chain variable region CDR3 comprising the amino acid sequence set forth in SEQ ID NO: 56 or a conservative modification thereof; or g) an α chain variable region CDR3 comprising the amino acid sequence set forth in SEQ ID NO: 63 or a conservative modification thereof, and a β chain variable region CDR3 comprising the amino acid sequence set forth in SEQ ID NO: 66 or a conservative modification thereof.

In certain embodiments, the extracellular domain comprises:

a) an α chain variable region CDR2 comprising the amino acid sequence set forth in SEQ ID NO: 2 or a conservative modification thereof, and a β chain variable region CDR2 comprising the amino acid sequence set forth in SEQ ID NO: 5 or a conservative modification thereof;

b) an α chain variable region CDR2 comprising the amino acid sequence set forth in SEQ ID NO: 12 or a conservative modification thereof, and a β chain variable region CDR2 comprising the amino acid sequence set forth in SEQ ID NO: 15 or a conservative modification thereof;

c) an α chain variable region CDR2 comprising the amino acid sequence set forth in SEQ ID NO: 22 or a conservative modification thereof, and a β chain variable region CDR2 comprising the amino acid sequence set forth in SEQ ID NO: 25 or a conservative modification thereof;
d) an α chain variable region CDR2 comprising the amino acid sequence set forth in SEQ ID NO: 32 or a conservative modification thereof, and a β chain variable region CDR2 comprising the amino acid sequence set forth in SEQ ID NO: 35 or a conservative modification thereof;
e) an α chain variable region CDR2 comprising the amino acid sequence set forth in SEQ ID NO: 42 or a conservative modification thereof, and a β chain variable region CDR2 comprising the amino acid sequence set forth in SEQ ID NO: 45 or a conservative modification thereof;
f) an α chain variable region CDR2 comprising the amino acid sequence set forth in SEQ ID NO: 52 or a conservative modification thereof, and a β chain variable region CDR2 comprising the amino acid sequence set forth in SEQ ID NO: 55 or a conservative modification thereof; or
g) an α chain variable region CDR2 comprising the amino acid sequence set forth in SEQ ID NO: 62 or a conservative modification thereof, and a β chain variable region CDR2 comprising the amino acid sequence set forth in SEQ ID NO: 65 or a conservative modification thereof.

In certain embodiments, the extracellular domain comprises:
a) an α chain variable region CDR1 comprising the amino acid sequence set forth in SEQ ID NO: 1 or a conservative modification thereof, and a β chain variable region CDR1 comprising the amino acid sequence set forth in SEQ ID NO: 4 or a conservative modification thereof;
b) an α chain variable region CDR1 comprising the amino acid sequence set forth in SEQ ID NO: 11 or a conservative modification thereof, and a β chain variable region CDR1 comprising the amino acid sequence set forth in SEQ ID NO: 14 or a conservative modification thereof;
c) an α chain variable region CDR1 comprising the amino acid sequence set forth in SEQ ID NO: 21 or a conservative modification thereof, and a β chain variable region CDR1 comprising the amino acid sequence set forth in SEQ ID NO: 24 or a conservative modification thereof;
d) an α chain variable region CDR1 comprising the amino acid sequence set forth in SEQ ID NO: 31 or a conservative modification thereof, and a β chain variable region CDR1 comprising the amino acid sequence set forth in SEQ ID NO: 34 or a conservative modification thereof;
e) an α chain variable region CDR1 comprising the amino acid sequence set forth in SEQ ID NO: 41 or a conservative modification thereof, and a β chain variable region CDR1 comprising the amino acid sequence set forth in SEQ ID NO: 44 or a conservative modification thereof;
f) an α chain variable region CDR1 comprising the amino acid sequence set forth in SEQ ID NO: 51 or a conservative modification thereof, and a β chain variable region CDR1 comprising the amino acid sequence set forth in SEQ ID NO: 54 or a conservative modification thereof, or
g) an α chain variable region CDR1 comprising the amino acid sequence set forth in SEQ ID NO: 61 or a conservative modification thereof, and a β chain variable region CDR1 comprising the amino acid sequence set forth in SEQ ID NO: 64 or a conservative modification thereof.

In certain embodiments, the extracellular domain comprises:
a) an α chain variable region CDR1 comprising the amino acid sequence set forth in SEQ ID NO: 1; an α chain variable region CDR2 comprising the amino acid sequence set forth in SEQ ID NO: 2; and an α chain variable region CDR3 comprising the amino acid sequence set forth in SEQ ID NO: 3;
b) an α chain variable region CDR1 comprising the amino acid sequence set forth in SEQ ID NO: 11; an α chain variable region CDR2 comprising the amino acid sequence set forth in SEQ ID NO: 12; and an α chain variable region CDR3 comprising the amino acid sequence set forth in SEQ ID NO: 13;
c) an α chain variable region CDR1 comprising the amino acid sequence set forth in SEQ ID NO: 21; an α chain variable region CDR2 comprising the amino acid sequence set forth in SEQ ID NO: 22; and an α chain variable region CDR3 comprising the amino acid sequence set forth in SEQ ID NO: 23;
d) an α chain variable region CDR1 comprising the amino acid sequence set forth in SEQ ID NO: 31; an α chain variable region CDR2 comprising the amino acid sequence set forth in SEQ ID NO: 32; and an α chain variable region CDR3 comprising the amino acid sequence set forth in SEQ ID NO: 33;
e) an α chain variable region CDR1 comprising the amino acid sequence set forth in SEQ ID NO: 41; an α chain variable region CDR2 comprising the amino acid sequence set forth in SEQ ID NO: 42; and an α chain variable region CDR3 comprising the amino acid sequence set forth in SEQ ID NO: 43;
f) an α chain variable region CDR1 comprising the amino acid sequence set forth in SEQ ID NO: 51; an α chain variable region CDR2 comprising the amino acid sequence set forth in SEQ ID NO: 52; and an α chain variable region CDR3 comprising the amino acid sequence set forth in SEQ ID NO: 53; or
g) an α chain variable region CDR1 comprising the amino acid sequence set forth in SEQ ID NO: 61; an α chain variable region CDR2 comprising the amino acid sequence set forth in SEQ ID NO: 62; and an α chain variable region CDR3 comprising the amino acid sequence set forth in SEQ ID NO: 63.

In certain embodiments, the extracellular domain comprises:
a) a β chain variable region CDR1 comprising the amino acid sequence set forth in SEQ ID NO: 4; a β chain variable region CDR2 comprising the amino acid sequence set forth in SEQ ID NO: 5; and a β chain variable region CDR3 comprising the amino acid sequence set forth in SEQ ID NO: 6;
b) a β chain variable region CDR1 comprising the amino acid sequence set forth in SEQ ID NO: 14; a β chain variable region CDR2 comprising the amino acid sequence set forth in SEQ ID NO: 15; and a β chain variable region CDR3 comprising the amino acid sequence set forth in SEQ ID NO: 16;
c) a β chain variable region CDR1 comprising the amino acid sequence set forth in SEQ ID NO: 24; a β chain variable region CDR2 comprising the amino acid sequence set forth in SEQ ID NO: 25; and a β chain variable region CDR3 comprising the amino acid sequence set forth in SEQ ID NO: 26;
d) a β chain variable region CDR1 comprising the amino acid sequence set forth in SEQ ID NO: 34; a β chain variable region CDR2 comprising the amino acid sequence set forth in SEQ ID NO: 35; and a β chain variable region CDR3 comprising the amino acid sequence set forth in SEQ ID NO: 36;
e) a β chain variable region CDR1 comprising the amino acid sequence set forth in SEQ ID NO: 44; a β chain variable region CDR2 comprising the amino acid sequence set forth in SEQ ID NO: 45; and a β chain variable region CDR3 comprising the amino acid sequence set forth in SEQ ID NO: 46;
f) a β chain variable region CDR1 comprising the amino acid sequence set forth in SEQ ID NO: 54; a β chain variable region CDR2 comprising the amino acid sequence set forth in SEQ ID NO: 55; and a β chain variable region CDR3 comprising the amino acid sequence set forth in SEQ ID NO: 56; or
g) a β chain variable region CDR1 comprising the amino acid sequence set forth in SEQ ID NO: 64; a β chain variable region CDR2 comprising the amino acid sequence set forth in SEQ ID NO: 65; and a β chain variable region CDR3 comprising the amino acid sequence set forth in SEQ ID NO: 66.

In certain embodiments, the extracellular domain comprises:
a) an α chain variable region CDR1 comprising the amino acid sequence set forth in SEQ ID NO: 1; an α chain variable region CDR2 comprising the amino acid sequence set forth in SEQ ID NO: 2; an α chain variable region CDR3 comprising the amino acid sequence set forth in SEQ ID NO: 3; a β chain variable region CDR1 comprising the amino acid sequence set forth in SEQ ID NO: 4; a β chain variable region CDR2 comprising the amino acid sequence set forth in SEQ ID NO: 5 and a β chain variable region CDR3 comprising the amino acid sequence set forth in SEQ ID NO: 6
b) an α chain variable region CDR1 comprising the amino acid sequence set forth in SEQ ID NO: 11; an α chain variable region CDR2 comprising the amino acid sequence set forth in SEQ ID NO: 12; an α chain variable region CDR3 comprising the amino acid sequence set forth in SEQ ID NO: 13; a β chain variable region CDR1 comprising the amino acid sequence set forth in SEQ ID NO: 14; a β chain variable region CDR2 comprising the amino acid sequence set forth in SEQ ID NO: 15 and a β chain variable region CDR3 comprising the amino acid sequence set forth in SEQ ID NO: 16;
c) an α chain variable region CDR1 comprising the amino acid sequence set forth in SEQ ID NO: 21; an α chain variable region CDR2 comprising the amino acid sequence set forth in SEQ ID NO: 22; an α chain variable region CDR3 comprising the amino acid sequence set forth in SEQ ID NO: 23; a β chain variable region CDR1 comprising the amino acid sequence set forth in SEQ ID NO: 24; a β chain variable region CDR2 comprising the amino acid sequence set forth in SEQ ID NO: 25 and a β chain variable region CDR3 comprising the amino acid sequence set forth in SEQ ID NO: 26;
d) an α chain variable region CDR1 comprising the amino acid sequence set forth in SEQ ID NO: 31; an α chain variable region CDR2 comprising the amino acid sequence set forth in SEQ ID NO: 32; an α chain variable region CDR3 comprising the amino acid sequence set forth in SEQ ID NO: 33; a β chain variable region CDR1 comprising the amino acid sequence set forth in SEQ ID NO: 34; a β chain variable region CDR2 comprising the amino acid sequence set forth in SEQ ID NO: 35 and a β chain variable region CDR3 comprising the amino acid sequence set forth in SEQ ID NO: 36;
e) an α chain variable region CDR1 comprising the amino acid sequence set forth in SEQ ID NO: 41; an α chain variable region CDR2 comprising the amino acid sequence set forth in SEQ ID NO: 42; an α chain variable region CDR3 comprising the amino acid sequence set forth in SEQ ID NO: 43; a β chain variable region CDR1 comprising the amino acid sequence set forth in SEQ ID NO: 44; a β chain variable region CDR2 comprising the amino acid sequence set forth in SEQ ID NO: 45 and a β chain variable region CDR3 comprising the amino acid sequence set forth in SEQ ID NO: 46;
f) an α chain variable region CDR1 comprising the amino acid sequence set forth in SEQ ID NO: 51; an α chain variable region CDR2 comprising the amino acid sequence set forth in SEQ ID NO: 52; an α chain variable region CDR3 comprising the amino acid sequence set forth in SEQ ID NO: 53; a β chain variable region CDR1 comprising the amino acid sequence set forth in SEQ ID NO: 54; a β chain variable region CDR2 comprising the amino acid sequence set forth in SEQ ID NO: 55 and a β chain variable region CDR3 comprising the amino acid sequence set forth in SEQ ID NO: 56; or
g) an α chain variable region CDR1 comprising the amino acid sequence set forth in SEQ ID NO: 61; an α chain variable region CDR2 comprising the amino acid sequence set forth in SEQ ID NO: 62; an α chain variable region CDR3 comprising the amino acid sequence set forth in SEQ ID NO: 63; a β chain variable region CDR1 comprising the amino acid sequence set forth in SEQ ID NO: 64; a β chain variable region CDR2 comprising the amino acid sequence set forth in SEQ ID NO: 65 and a β chain variable region CDR3 comprising the amino acid sequence set forth in SEQ ID NO: 66.

In certain embodiments, the extracellular domain comprises an α chain variable region CDR1 comprising the amino acid sequence set forth in SEQ ID NO: 41; an α chain variable region CDR2 comprising the amino acid sequence set forth in SEQ ID NO: 42; an α chain variable region CDR3 comprising the amino acid sequence set forth in SEQ ID NO: 43; a β chain variable region CDR1 comprising the amino acid sequence set forth in SEQ ID NO: 44; a β chain variable region CDR2 comprising the amino acid sequence set forth in SEQ ID NO: 45 and a β chain variable region CDR3 comprising the amino acid sequence set forth in SEQ ID NO: 46.

In certain embodiments, the extracellular domain and comprises an α chain variable region comprising an amino acid sequence that is at least about 80% homologous or identical to the amino acid sequence set forth in SEQ ID NO: 7, SEQ ID NO: 17, SEQ ID NO: 27, SEQ ID NO: 37, SEQ ID NO: 47, SEQ ID NO: 57 or SEQ ID NO: 67.

In certain embodiments, the extracellular domain comprises an α chain variable region comprising the amino acid sequence set forth in SEQ ID NO: 7, SEQ ID NO: 17, SEQ ID NO: 27, SEQ ID NO: 37, SEQ ID NO: 47, SEQ ID NO: 57, or SEQ ID NO: 67.

In certain embodiments, the extracellular domain comprises a β chain variable region comprising an amino acid sequence that is at least about 80% homologous or identical to the amino acid sequence set forth in SEQ ID NO: 8, SEQ ID NO: 18, SEQ ID NO: 28, SEQ ID NO: 38, SEQ ID NO: 48, SEQ ID NO: 58, or SEQ ID NO: 68.

In certain embodiments, the extracellular domain comprises a β chain variable region comprising the amino acid sequence set forth in SEQ ID NO: 8, SEQ ID NO: 18, SEQ ID NO: 28, SEQ ID NO: 38, SEQ ID NO: 48, SEQ ID NO: 58, or SEQ ID NO: 68.

In certain embodiments, the extracellular domain comprises:
  a) an α chain variable region comprising an amino acid sequence that is at least about 80% homologous or identical to the amino acid sequence set forth in SEQ ID NO: 7, SEQ ID NO: 17, SEQ ID NO: 27, SEQ ID NO: 37, SEQ ID NO: 47, SEQ ID NO: 57, or SEQ ID NO: 67; and
  b) a β chain variable region comprising an amino acid sequence that is at least about 80% homologous or identical to the amino acid sequence set forth in SEQ ID NO: 8, SEQ ID NO: 18, SEQ ID NO: 28, SEQ ID NO: 38, SEQ ID NO: 48 SEQ ID NO: 58, or SEQ ID NO: 68.

In certain embodiments, the extracellular domain comprises: an α chain variable region comprising the amino acid sequence set forth in SEQ ID NO: 7, SEQ ID NO: 17, SEQ ID NO: 27, SEQ ID NO: 37, SEQ ID NO: 47, SEQ ID NO: 57, or SEQ ID NO:67; and a β chain variable region comprising the amino acid sequence set forth in SEQ ID NO: 8, SEQ ID NO: 18, SEQ ID NO: 28, SEQ ID NO: 38, SEQ ID NO: 48, SEQ ID NO: 58, or SEQ ID NO: 68.

In certain embodiments, the extracellular domain comprises:
  a) an α chain variable region comprising an amino acid sequence that is at least about 80% homologous or identical to the amino acid sequence set forth in SEQ ID NO: 7; and a β chain variable region comprising an amino acid sequence that is at least about 80% homologous or identical to the amino acid sequence set forth in SEQ ID NO: 8;
  b) an α chain variable region comprising an amino acid sequence that is at least about 80% homologous or identical to the amino acid sequence set forth in SEQ ID NO: 17; and a β chain variable region comprising an amino acid sequence that is at least about 80% homologous or identical to the amino acid sequence set forth in SEQ ID NO: 18;
  c) an α chain variable region comprising an amino acid sequence that is at least about 80% homologous or identical to the amino acid sequence set forth in SEQ ID NO: 27; and a β chain variable region comprising an amino acid sequence that is at least about 80% homologous or identical to the amino acid sequence set forth in SEQ ID NO: 28;
  d) an α chain variable region comprising an amino acid sequence that is at least about 80% homologous or identical to SEQ ID NO: the amino acid sequence set forth in 37; and a β chain variable region comprising an amino acid sequence that is at least about 80% homologous or identical to the amino acid sequence set forth in SEQ ID NO: 38;
  e) an α chain variable region comprising an amino acid sequence that is at least about 80% homologous or identical to the amino acid sequence set forth in SEQ ID NO: 47; and a β chain variable region comprising an amino acid sequence that is at least about 80% homologous or identical to the amino acid sequence set forth in SEQ ID NO: 48;
  f) an α chain variable region comprising an amino acid sequence that is at least about 80% homologous or identical to the amino acid sequence set forth in SEQ ID NO: 57; and a β chain variable region comprising an amino acid sequence that is at least about 80% homologous or identical to the amino acid sequence set forth in SEQ ID NO: 58; or
  g) an α chain variable region comprising an amino acid sequence that is at least about 80% homologous or identical to SEQ ID NO: the amino acid sequence set forth in 67; and a β chain variable region comprising an amino acid sequence that is at least about 80% homologous or identical to the amino acid sequence set forth in SEQ ID NO: 68.

In certain embodiments, the extracellular domain comprises:
  a) an α chain variable region comprising the amino acid sequence set forth in SEQ ID NO: 7, and a β chain variable region comprising the amino acid sequence set forth in SEQ ID NO: 8;
  b) an α chain variable region comprising the amino acid sequence set forth in SEQ ID NO: 17, and a β chain variable region comprising the amino acid sequence set forth in SEQ ID NO: 18;
  c) an α chain variable region comprising the amino acid sequence set forth in SEQ ID NO: 27, and a β chain variable region comprising the amino acid sequence set forth in SEQ ID NO: 28;
  d) an α chain variable region comprising the amino acid sequence set forth in SEQ ID NO: 37, and a β chain variable region comprising the amino acid sequence set forth in SEQ ID NO: 38;
  e) an α chain variable region comprising the amino acid sequence set forth in SEQ ID NO: 47, and a β chain variable region comprising the amino acid sequence set forth in SEQ ID NO: 48; or
  f) an α chain variable region comprising the amino acid sequence set forth in SEQ ID NO: 57, and a β chain variable region comprising the amino acid sequence set forth in SEQ ID NO: 58; or
  g) an α chain variable region comprising the amino acid sequence set forth in SEQ ID NO: 67, and a β chain variable region comprising the amino acid sequence set forth in SEQ ID NO: 68.

In certain embodiments, the extracellular domain comprises an α chain variable region comprising the amino acid sequence set forth in SEQ ID NO: 47 and a β chain variable region comprising the amino acid sequence set forth in SEQ ID NO: 48.

In certain embodiments, the TCR comprises an extracellular domain comprising an α chain comprising an amino acid sequence selected from the group consisting of: SEQ ID NOS: 9, 19, 29, 39, 49, 59 and 69; and a β chain comprising an amino acid sequence selected from the group consisting of SEQ ID NOS: 10, 20, 30, 40, 50, 60 and 70. In certain embodiments, the extracellular domain comprises an α chain comprising the amino acid sequence set forth in SEQ ID NO: 49 and a β chain comprising the amino acid sequence set forth in SEQ ID NO: 50.

In certain embodiments, the extracellular domain binds to the same epitope on a human mutant PIK3CA peptide as a reference TCR or a functional fragment thereof, wherein the reference TCR or a functional fragment thereof comprises:

a) an α chain variable region CDR1 comprising the amino acid sequence set forth in SEQ ID NO: 1; an α chain variable region CDR2 comprising the amino acid sequence set forth in SEQ ID NO: 2; an α chain variable region CDR3 comprising the amino acid sequence set forth in SEQ ID NO: 3; a β chain variable region CDR1 comprising the amino acid sequence set forth in SEQ ID NO: 4; a β chain variable region CDR2 comprising the amino acid sequence set forth in SEQ ID NO: 5 and a β chain variable region CDR3 comprising the amino acid sequence set forth in SEQ ID NO: 6;

b) an α chain variable region CDR1 comprising the amino acid sequence set forth in SEQ ID NO: 11; an α chain variable region CDR2 comprising the amino acid sequence set forth in SEQ ID NO: 12; an α chain variable region CDR3 comprising the amino acid sequence set forth in SEQ ID NO: 13; a β chain variable region CDR1 comprising the amino acid sequence set forth in SEQ ID NO: 14; a β chain variable region CDR2 comprising the amino acid sequence set forth in SEQ ID NO: 15 and a β chain variable region CDR3 comprising the amino acid sequence set forth in SEQ ID NO: 16;

c) an α chain variable region CDR1 comprising the amino acid sequence set forth in SEQ ID NO: 21; an α chain variable region CDR2 comprising the amino acid sequence set forth in SEQ ID NO: 22; an α chain variable region CDR3 comprising the amino acid sequence set forth in SEQ ID NO: 23; a β chain variable region CDR1 comprising the amino acid sequence set forth in SEQ ID NO: 24; a β chain variable region CDR2 comprising the amino acid sequence set forth in SEQ ID NO: 25 and a β chain variable region CDR3 comprising the amino acid sequence set forth in SEQ ID NO: 26;

d) an α chain variable region CDR1 comprising the amino acid sequence set forth in SEQ ID NO: 31; an α chain variable region CDR2 comprising the amino acid sequence set forth in SEQ ID NO: 32; an α chain variable region CDR3 comprising the amino acid sequence set forth in SEQ ID NO: 33; a β chain variable region CDR1 comprising the amino acid sequence set forth in SEQ ID NO: 34; a β chain variable region CDR2 comprising the amino acid sequence set forth in SEQ ID NO: 35 and a β chain variable region CDR3 comprising the amino acid sequence set forth in SEQ ID NO: 36;

e) an α chain variable region CDR1 comprising the amino acid sequence set forth in SEQ ID NO: 41; an α chain variable region CDR2 comprising the amino acid sequence set forth in SEQ ID NO: 42; an α chain variable region CDR3 comprising the amino acid sequence set forth in SEQ ID NO: 43; a β chain variable region CDR1 comprising the amino acid sequence set forth in SEQ ID NO: 44; a β chain variable region CDR2 comprising the amino acid sequence set forth in SEQ ID NO: 45 and a β chain variable region CDR3 comprising the amino acid sequence set forth in SEQ ID NO: 46;

f) an α chain variable region CDR1 comprising the amino acid sequence set forth in SEQ ID NO: 51; an α chain variable region CDR2 comprising the amino acid sequence set forth in SEQ ID NO: 52; an α chain variable region CDR3 comprising the amino acid sequence set forth in SEQ ID NO: 53; a β chain variable region CDR1 comprising the amino acid sequence set forth in SEQ ID NO: 54; a β chain variable region CDR2 comprising the amino acid sequence set forth in SEQ ID NO: 55 and a β chain variable region CDR3 comprising the amino acid sequence set forth in SEQ ID NO: 56; or g) an α chain variable region CDR1 comprising the amino acid sequence set forth in SEQ ID NO: 61; an α chain variable region CDR2 comprising the amino acid sequence set forth in SEQ ID NO: 62; an α chain variable region CDR3 comprising the amino acid sequence set forth in SEQ ID NO: 63; a β chain variable region CDR1 comprising the amino acid sequence set forth in SEQ ID NO: 64; a β chain variable region CDR2 comprising the amino acid sequence set forth in SEQ ID NO: 65 and a β chain variable region CDR3 comprising the amino acid sequence set forth in SEQ ID NO: 66.

In certain embodiments, the reference TCR or a functional fragment thereof comprises an α chain variable region CDR1 comprising the amino acid sequence set forth in SEQ ID NO: 41; an α chain variable region CDR2 comprising the amino acid sequence set forth in SEQ ID NO: 42; an α chain variable region CDR3 comprising the amino acid sequence set forth in SEQ ID NO: 43; a β chain variable region CDR1 comprising the amino acid sequence set forth in SEQ ID NO: 44; a β chain variable region CDR2 comprising the amino acid sequence set forth in SEQ ID NO: 45 and a β chain variable region CDR3 comprising the amino acid sequence set forth in SEQ ID NO: 46.

In certain embodiments, the TCR is recombinantly expressed, or expressed from a vector. In certain embodiments, the TCR does not target a wildtype PIK3CA peptide.

In certain embodiments, the TCR comprises a modified α-chain constant region and/or a modified β-chain constant region. In certain embodiments, the modified α-chain constant region comprises an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous or identical to the amino acid sequence set forth in SEQ ID NO: 80 or 81. In certain embodiments, the modified α-chain constant region comprises an amino acid sequence set forth in SEQ ID NO: 80. In certain embodiments, the modified β-chain constant region comprises an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous or identical to the amino acid sequence set forth in SEQ ID NO: 82 or 83. In certain embodiments, the modified β-chain constant region comprises an amino acid sequence set forth in SEQ ID NO: 82.

The presently disclosed subject matter further provides an isolated immunoresponsive cell comprising the TCR disclosed herein. In certain embodiments, the immunoresponsive cell is transduced with the TCR. In certain embodiments, the TCR is constitutively expressed on the surface of the immunoresponsive cell. In certain embodiments, the immunoresponsive cell is selected from the group consisting of a T cell, a Natural Killer (NK) cell, a human embryonic stem cell, a lymphoid progenitor cell, a T cell-precursor cell, and a pluripotent stem cell from which lymphoid cells may be differentiated. In certain embodiments, the immunoresponsive cell is a T cell. In certain embodiments, the T cell is selected from the group consisting of a cytotoxic T lymphocyte (CTL), a regulatory T cell, and central memory T cells.

The presently disclosed subject matter further provides a composition comprising the immunoresponsive cell disclosed herein. In certain embodiments, the composition is a pharmaceutical composition comprising a pharmaceutically acceptable carrier.

The presently disclosed subject matter further provides an isolated nucleic acid molecule encoding the T cell receptor (TCR) disclosed herein. The presently disclosed subject matter further provides a method for producing an immunoresponsive cell that binds to a human mutant PIK3CA peptide, comprising introducing into the immunoresponsive cell a nucleic acid sequence that encodes the TCR disclosed herein.

The presently disclosed subject matter further provides a vector comprising the isolated nucleic acid molecule disclosed herein. In certain embodiments, the vector is a γ-retroviral vector.

The presently disclosed subject matter further provides a host cell comprising the nucleic acid molecule disclosed herein. In certain embodiments, the host cell is a T cell.

The presently disclosed subject matter further provides methods of treating and/or preventing a malignancy in a subject. In certain embodiments, the method comprises administering to the subject an effective amount of the immunoresponsive cell disclosed herein. In certain embodiments, the malignancy is selected from the group consisting of any PIK3CA-mutated cancers. In certain embodiments, the malignancy is selected from the group consisting of breast cancer, endometrial cancer, cervical cancer, anal cancer, bladder cancer, colorectal cancer, head and neck squamous cell carcinoma, nonmelanoma skin cancer and salivary gland cancer. In certain embodiments, the malignancy is breast cancer. In certain embodiments, the method reduces or eradicates the tumor burden in the subject. In certain embodiments, the subject is a human.

The presently disclosed subject matter further provides kits for treating and/or preventing a malignancy. In certain embodiments, the kit comprises the immunoresponsive cell disclosed herein, the isolated nucleic acid molecule disclosed herein, or the vector disclosed herein. In certain embodiments, the kit further comprises written instructions for using the immunoresponsive cell for treating a subject having a malignancy.

BRIEF DESCRIPTION OF THE FIGURES

The following Detailed Description, given by way of example but not intended to limit the invention to specific embodiments described, may be understood in conjunction with the accompanying drawings.

FIG. 2 depicts location of hotspot mutations in PIK3CA in breast cancer subtypes.

FIG. 7 discloses "SGSG" as SEQ ID NO: 85.

FIG. 8 depicts stimulation and screening constructs for mutant PIK3CA. FIG. 8 discloses SEQ ID NOS 71-79, respectively, in order of appearance.

FIG. 13 depicts that sequencing correctly identified, paired, and quantified known TCRs within a bulk PBMC population. FIG. 13 discloses the "CDR3: Alpha" sequences as SEQ ID NOS 86-95 and the "CDR3: Beta" sequences as SEQ ID NOS 96-121, all respectively, in order of appearance.

FIG. 14 depicts confirmation of RC8 reactivity. Autologous APCs transfected with RNA encoding either WT or the R/L substitutions at position 1047 in the PIK3CA gene were incubated with T cells from Well C8 (referred to as RC8). Delta CT values determined by upregulation of IFN-g transcript indicate mutation-specific recognition of both R and L hotspot mutations and no WT recognition. The table in the lower panel lists the CDR3 sequences (SEQ ID NOS 3, 6, 16, 6, 3, 13, 16, 26, 122, 13, 123-124, 23 and 26, respectively, in order of appearance) and frequencies of the top 10 clonotypes in RC8 derived by the platform.

FIG. 17 depicts sequences of top clonotypes (RC8-1, RC8-2, RC8-3, LB11-1, LB11-2, LB11-3 and LB11-4) of the unique TCRs constructed into expression vectors, where the alpha chain and the beta chain of each TCR were connected by a furin-2A peptide. Based on previously described techniques, the human constant regions of the alpha and beta chains were replaced with mouse constant regions to prevent mispairing with endogenous TCR. FIG. 17 discloses SEQ ID NOS 6, 3, 125, 16, 13, 126, 26, 23, 127, 36, 33, 128, 46, 43, 129, 56, 53, 130, 66, 63 and 131, respectively, in order of appearance.

FIG. 18 is a summary of the characteristics of the PIK3CA mutation-specific TCRs.

FIG. 19 discloses SEQ ID NOS 36, 46, 33, 36, 43, 46, 56, 53, 56, 43, 33, 53, 63 and 66, respectively, in order of appearance.

FIG. 23 discloses SEQ ID NOS 36, 46, 33, 36, 43, 46, 56, 53, 56, 43, 33, 53, 63 and 66, respectively, in order of appearance.

DETAILED DESCRIPTION OF THE INVENTION

Figure 1:
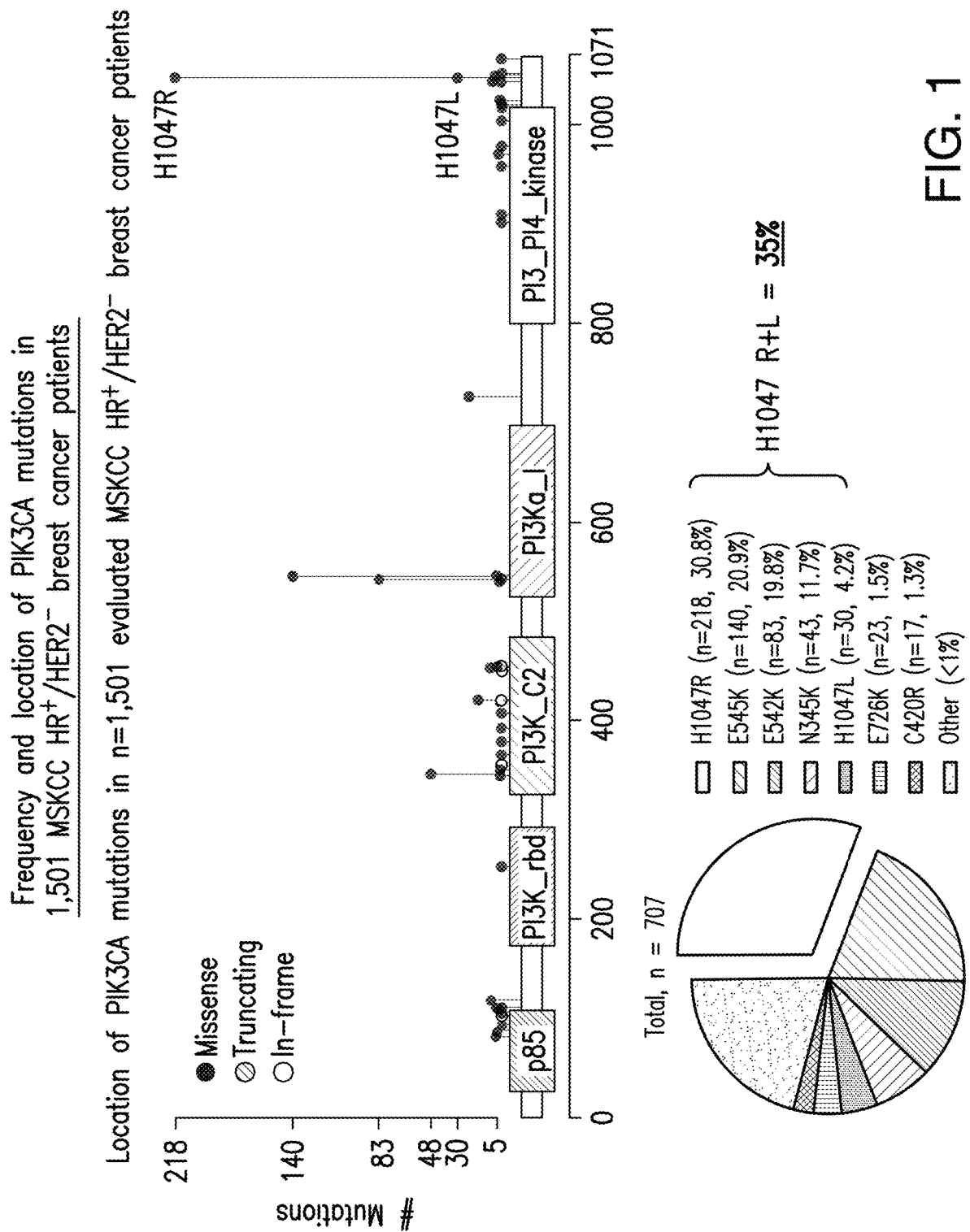
FIG. 1 depicts frequency and location of PIK3CA mutations in 1,501 MSKCC HR+/HER2− breast cancer patients.

The presently disclosed subject matter provides TCRs targeting PIK3CA (e.g., human PIK3CA) comprising a mutation.

The presently disclosed subject matter also provides immunoresponsive cells (e.g., a T cell (e.g., a cytotoxic T lymphocyte (CTL), a regulatory T cell, a central memory T cell, etc.), a Natural Killer (NK) cell, a human embryonic stem cell, a lymphoid progenitor cell, a T cell-precursor cell, and a pluripotent stem cell from which lymphoid cells may be differentiated) comprising the PIK3CA-targeted TCRs, and methods of using such immunoresponsive cells for treating a tumor, e.g., breast cancer.

I. Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "cell population" refers to a group of at least two cells expressing similar or different phenotypes. In non-limiting examples, a cell population can include at least about 10, at least about 100, at least about 200, at least about 300, at least about 400, at least about 500, at least about 600, at least about 700, at least about 800, at least about 900, at least about 1000 cells expressing similar or different phenotypes.

As used herein, the term "vector" refers to any genetic element, such as a plasmid, phage, transposon, cosmid, chromosome, virus, virion, etc., which is capable of replication when associated with the proper control elements and which can transfer gene sequences into cells. Thus, the term includes cloning and expression vehicles, as well as viral vectors and plasmid vectors.

As used herein, the term "expression vector" refers to a recombinant nucleic acid sequence, e.g., a recombinant DNA molecule, containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, "CDRs" are defined as the complementarity determining region amino acid sequences of a TCR, which are the hypervariable regions of TCR α-chain and β-chain. Generally, a TCR comprises at least three CDRs in the α-chain variable region and at least three CDRs in the β-chain variable region. CDRs provide the majority of contact residues for the binding of the TCR to the antigen or epitope. In certain embodiments, the CDRs regions are delineated using the Kabat system (Kabat, E. A., et al. (1991) Sequences of Proteins of Immunological Interest, Fifth Edition, U.S. Department of Health and Human Services, NIH Publication No. 91-3242). In certain embodiments, the CDRs are delineated using the Chothia numbering system (Chothia et al., J Mol Biol. (1987) 196:901-17). In certain embodiments, the CDRs are delineated using the AbM numbering system (Abhinandan et al., Mol. Immunol. 2008, 45, 3832-3839). In certain embodiments, the CDRs regions are delineated using the IMGT numbering system (accessible at www.imgt.org/IMGTScientificChart/Numbering/IMGTIGVLsuperfamily.html, www.imgt.org/IMGTindex/numbering.php).

Nucleic acid molecules useful in the presently disclosed subject matter include any nucleic acid molecule that encodes a polypeptide or a fragment thereof. In certain embodiments, nucleic acid molecules useful in the presently disclosed subject matter include nucleic acid molecules that encode a TCR or a target-binding portion thereof. Such nucleic acid molecules need not be 100% identical with an endogenous nucleic acid sequence, but will typically exhibit substantial identity. Polynucleotides having "substantial homology" or "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and about 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In certain embodiments, hybridization will occur at 30° C. in 750 mM NaCl, 75 mM trisodium citrate, and 1% SDS. In certain embodiments, hybridization will occur at 37° C. in 500 mM NaCl, 50 mM trisodium citrate, 1% SDS, 35% formamide, and 100 μg/ml denatured salmon sperm DNA (ssDNA). In certain embodiments, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In certain embodiments, wash steps will occur at 25° C. in 30 mM NaCl, 3 mM trisodium citrate, and 0.1% SDS. In certain embodiments, wash steps will occur at 42° C. in 15 mM NaCl, 1.5 mM trisodium citrate, and 0.1% SDS. In certain embodiments, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Rogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

The terms "substantially homologous" or "substantially identical" mean a polypeptide or nucleic acid molecule that exhibits at least 50% homology or identity to a reference amino acid sequence (for example, any one of the amino acid sequences described herein) or nucleic acid sequence (for example, any one of the nucleic acid sequences described herein). For example, such a sequence is at least about 60%, about 65%, about 70%, about 75%, about 80%, about 85%, about 90%, about 95% or even about 99% homologous or identical at the amino acid level or nucleic acid to the sequence used for comparison.

Sequence homology or sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. In an exemplary approach to determining the degree of identity, a BLAST program may be used, with a probability score between $e^{-3}$ and $e^{-100}$ indicating a closely related sequence.

As used herein, the term "analog" refers to a structurally related polypeptide or nucleic acid molecule having the function of a reference polypeptide or nucleic acid molecule.

As used herein, the term "ligand" refers to a molecule that binds to a receptor. In particular, the ligand binds a receptor on another cell, allowing for cell-to-cell recognition and/or interaction.

As used herein, the term "disease" refers to any condition or disorder that damages or interferes with the normal function of a cell, tissue, or organ. Examples of diseases include neoplasm or pathogen infection of cell.

An "effective amount" (or "therapeutically effective amount") is an amount sufficient to affect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease (e.g., a neoplasm), or otherwise reduce the pathological consequences of the disease (e.g., a neoplasm). The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the immunoresponsive cells administered.

As used herein, the term "neoplasm" refers to a disease characterized by the pathological proliferation of a cell or tissue and its subsequent migration to or invasion of other tissues or organs. Neoplasm growth is typically uncontrolled and progressive, and occurs under conditions that would not elicit, or would cause cessation of, multiplication of normal cells. Neoplasms can affect a variety of cell types, tissues, or organs, including but not limited to an organ selected from the group consisting of bladder, colon, bone, brain, breast, cartilage, glia, esophagus, fallopian tube, gallbladder, heart, intestines, kidney, liver, lung, lymph node, nervous tissue, ovaries, pleura, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasms include cancers, such as sarcomas, carcinomas, or plasmacytomas (malignant tumor of the plasma cells).

As used herein, the term "heterologous nucleic acid molecule or polypeptide" refers to a nucleic acid molecule (e.g., a cDNA, DNA or RNA molecule) or polypeptide that is not normally present in a cell or sample obtained from a cell. This nucleic acid may be from another organism, or it may be, for example, an mRNA molecule that is not normally expressed in a cell or sample.

As used herein, the term "immunoresponsive cell" refers to a cell that functions in an immune response or a progenitor, or progeny thereof.

As used herein, the term "modulate" refers positively or negatively alter. Exemplary modulations include an about 1%, about 2%, about 5%, about 10%, about 25%, about 50%, about 75%, or about 100% change.

As used herein, the term "increase" refers to alter positively by at least about 5%, including, but not limited to, alter positively by about 5%, by about 10%, by about 25%, by about 30%, by about 50%, by about 75%, or by about 100%.

As used herein, the term "reduce" refers to alter negatively by at least about 5% including, but not limited to, alter negatively by about 5%, by about 10%, by about 25%, by about 30%, by about 50%, by about 75%, or by about 100%.

As used herein, the term "isolated cell" refers to a cell that is separated from the molecular and/or cellular components that naturally accompany the cell.

As used herein, the term "isolated," "purified," or "biologically pure" refers to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or polypeptide of the presently disclosed subject matter is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

As used herein, the term "secreted" is meant a polypeptide that is released from a cell via the secretory pathway through the endoplasmic reticulum, Golgi apparatus, and as a vesicle that transiently fuses at the cell plasma membrane, releasing the proteins outside of the cell.

As used herein, the term "specifically binds" or "specifically binds to" or "specifically target" is meant a polypeptide or fragment thereof that recognizes and binds a biological molecule of interest (e.g., a polypeptide), but which does not substantially recognize and bind other molecules in a sample, for example, a biological sample, which includes or expresses a human mutant PIK3CA peptide.

As used herein, the term "treating" or "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

As used herein, the term "subject" refers to any animal (e.g., a mammal), including, but not limited to, humans, non-human primates, rodents, and the like (e.g., which is to be the recipient of a particular treatment, or from whom cells are harvested).

II. PIK3CA

Phosphatidylinositol-4,5-bisphosphate 3-kinase catalytic subunit alpha (PIK3CA; Gene ID: 5290; also known as MCM, CWS5, MCAP, PI3K, CLOVE, MCMTC, PI3K-alpha and p110-alpha), is a gene encoding a catalytic subunit of phosphatidylinositol 3 kinase, which uses ATP to phosphorylate PtdIns, PtdIns4P and PtdIns (4,5) P2. PIK3CA has been found to be oncogenic and has been implicated in breast cancer and cervical cancer.

III. T-Cell Receptor (TCR)

A TCR is a disulfide-linked heterodimeric protein consisting of two variable chains expressed as part of a complex with the invariant CD3 chain molecules. A TCR is found on the surface of T cells, and is responsible for recognizing antigens as peptides bound to major histocompatibility complex (MHC) molecules. In certain embodiments, a TCR comprises an α chain and a β chain (encoded by TRA and TRB, respectively). In certain embodiments, a TCR comprises a γ chain and a & chain (encoded by TRG and TRD, respectively).

Each chain of a TCR comprises two extracellular domains: a variable region and a constant region. The constant region is proximal to the cell membrane, followed by a transmembrane domain and a short cytoplasmic tail (i.e., an intracellular domain). The variable region binds to the peptide/MHC complex. The variable region of both chains each has three complementarity determining regions (CDRs).

In certain embodiments, a TCR can form a receptor complex with three dimeric signaling modules CD38/8, CD3γ/& and CD247 YS or In. When a TCR complex engages with its antigen and MHC (peptide/MHC), the T cell expressing the TCR complex is activated.

In certain embodiments, the presently disclosed subject matter provides a recombinant TCR.

In certain embodiments, the TCR is a non-naturally occurring TCR. In certain embodiments, the TCR differs from any naturally occurring TCR by at least one amino acid residue. In certain embodiments, the TCR differs from any naturally occurring TCR by at least 2, 3, 4, 5, 6, 7, 8, 9, 10, 11, 12, 13, 14, 15, 20, 25, 30, 40, 50, 60, 70, 80, 90, 100 or more amino acid residues. In certain embodiments, the TCR is modified from a naturally occurring TCR by at least one amino acid residue. In certain embodiments, the TCR is modified from a naturally occurring TCR by at least 2, 3, 4, 5, 6, 7, 8, 9, 10, 11, 12, 13, 14, 15, 20, 25, 30, 40, 50, 60, 70, 80, 90, 100 or more amino acid residues.

In certain embodiments, the TCR specifically targets a PIK3CA peptide, wherein the PIK3CA peptide comprises a mutation. In certain embodiments, the mutation is selected from the group consisting of H104R, E545K, E542K, N345K, H1047L, E726K, C420R and any combination thereof. In certain embodiments, the mutation is H1047R or H1047L. In certain embodiments, the TCR does not targets a wildtype PIK3CA peptide.

In certain embodiments, the TCR specifically targets a PIK3CA peptide listed in FIG. 8. In certain embodiments, the PIK3CA peptide comprises or has the amino acid sequence set forth in SEQ ID NO: 71, SEQ ID NO: 72, SEQ ID NO: 73, SEQ ID NO: 74, SEQ ID NO: 75, SEQ ID NO: 76, or SEQ ID NO: 77, which are provided below.

[SEQ ID NO: 71]
HAGLSNRLARDNELRENDKEQLKAISTRDPLSEITEQEKDFLWSHRHYCV

TIPEILPKLLLSVKW

[SEQ ID NO: 72]
HAGLSNRLARDNELRENDKEQLKAISTRDPLSKITEQEKDFLWSHRHYCV

TIPEILPKLLLSVKW

[SEQ ID NO: 73]
LSNRLARDNELRENDKEQLKAISTRDPLSEITEQEKDFLWSHRHYCVTIP

EILPKLLLSVKWNSR

[SEQ ID NO: 74]
LSNRLARDNELRENDKEQLKAISTRDPLSEITKQEKDFLWSHRHYCVTIP

EILPKLLLSVKWNSR

[SEQ ID NO: 75]
KTLALDKTEQEALEYFMKQMNDAHHGGWTTKMDWIFHTIKQHALN

[SEQ ID NO: 76]
KTLALDKTEQEALEYFMKQMNDARHGGWTTKMDWIFHTIKQHALN

[SEQ ID NO: 77]
KTLALDKTEQEALEYFMKQMNDALHGGWTTKMDWIFHTIKQHALN

In certain embodiments, the TCR specifically targets a PIK3CA peptide associated with a HLA class I complex, e.g., HLA-A, HLA-B and HLA-C. In certain embodiments, the TCR specifically targets a PIK3CA peptide associated with a HLA class II complex, e.g., HLA-DP, HLA-DM, HLA-DO, HLA-DQ and HLA-DR.

TCR Clonetypes

In certain embodiments, the TCR comprises an α chain comprising the amino acid sequence set forth in SEQ ID NO: 9, SEQ ID NO: 19, SEQ ID NO: 29, SEQ ID NO: 39, SEQ ID NO: 49, SEQ ID NO: 59, or SEQ ID NO: 69. In certain embodiments, the TCR comprises a β chain comprising the amino acid sequence set forth in SEQ ID NO: 10, SEQ ID NO: 20, SEQ ID NO: 30, SEQ ID NO: 40, SEQ ID NO: 50, SEQ ID NO: 60, or SEQ ID NO: 70.

In certain embodiments, the extracellular domain of the TCR comprises an α chain variable region comprising the amino acid sequence set forth in SEQ ID NO: 7, SEQ ID NO: 17, SEQ ID NO: 27, SEQ ID NO: 37, SEQ ID NO: 47, SEQ ID NO: 57, or SEQ ID NO: 67. In certain embodiments, the extracellular domain of the TCR comprises a β chain variable region comprising the amino acid sequence set forth in SEQ ID NO: 8, SEQ ID NO: 18, SEQ ID NO: 28, SEQ ID NO: 38, SEQ ID NO: 48, SEQ ID NO: 58, or SEQ ID NO: 68. The sequences of SEQ ID NOS: 1-70 are described in the following Tables 1-7.

In certain embodiments, the TCR is a human TCR and specifically binds to a mutant PIK3CA peptide (e.g., a human mutant PIK3CA peptide), which is designated as RC8-1.

In certain embodiments, the TCR is a human TCR, which comprises an α chain comprising the amino acid sequence set forth in SEQ ID NO: 9 and/or a β chain comprising the amino acid sequence set forth in SEQ ID NO: 10. SEQ ID NOS: 9 and 10 are provided in Table 1.

In certain embodiments, the extracellular domain of the TCR comprises an α chain variable region and a β chain variable region or CDRs selected from Table 1. In certain embodiments, the extracellular domain comprises an α chain variable region comprising an amino acid sequence that is at least about 80% (e.g., at least about 85%, at least about 90%, or at least about 95%) homologous or identical to the amino acid sequence set forth in SEQ ID NO: 7, as shown in Table 1. For example, the extracellular domain comprises an α chain variable region comprising an amino acid sequence that is about 80%, 81%, 82%, 83%, 84%, 85%, 86%, 87%, 88%, 89%, 90%, 91%, 92%, 93%, 94%, 95%, 96%, 97%, 98%, or 99% homologous or identical to the amino acid sequence set forth in SEQ ID NO: 7. In certain embodiments, the extracellular domain comprises an α chain variable region comprising the amino acid sequence set forth in SEQ ID NO:7. In certain embodiments, the extracellular domain comprises a β chain variable region comprising an amino acid sequence that is at least about 80% (e.g., at least about 85%, at least about 90%, or at least about 95%) homologous or identical to the amino acid sequence set forth in SEQ ID NO: 8, as shown in Table 1. For example, the extracellular domain comprises a β chain variable region comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous or identical to the amino acid sequence set forth in SEQ ID NO: 8. In certain embodiments, the extracellular domain comprises a β chain variable region comprising the amino acid sequence set forth in SEQ ID NO:8. In certain embodiments, the extracellular domain comprises an α chain variable region comprising an amino acid sequence that is at least about 80% (e.g., at least about 85%, at least about 90%, or at least about 95%) homologous or identical to the amino acid sequence set forth in SEQ ID NO: 7, and a β chain variable region comprising an amino acid sequence that is at least about 80% (e.g., at least about 85%, at least about 90%, or at least about 95%) homologous or identical to the amino acid sequence set forth in SEQ ID NO: 8. In certain embodiments, the extracellular domain comprises an α chain variable region comprising the amino acid sequence set forth in SEQ ID NO:7 and a β chain variable region comprising the amino acid sequence set forth in SEQ ID NO:8. In certain embodiments, the extracellular domain comprises an α chain variable region CDR1 comprising the amino acid sequence set forth in SEQ ID NO:1 or a conservative modification thereof, an α chain variable region CDR2 comprising the amino acid sequence set forth in SEQ ID NO:2 or a conservative modification thereof, and an α chain variable region CDR3 comprising the amino acid sequence set forth in SEQ ID NO:3 or a conservative modification of SEQ ID NO: 3, as shown in Table 1. In certain embodiments, the extracellular domain comprises an α chain variable region CDR1 comprising the amino acid sequence set forth in SEQ ID NO:1, an α chain variable region CDR2 comprising the amino acid sequence set forth in SEQ ID NO:2, and an α chain variable region CDR3 comprising the amino acid sequence set forth in SEQ ID NO:3. In certain embodiments, the extracellular domain comprises a β chain variable region CDR1 comprising the amino acid sequence set forth in SEQ ID NO:4 or a conservative modification thereof, a β chain variable region CDR2 comprising the amino acid sequence set forth in SEQ ID NO: 5 or a conservative modification thereof, and a β chain variable region CDR3 comprising the amino acid sequence set forth in SEQ ID NO: 6 or a conservative modification thereof, as shown in Table 1. In certain embodiments, the extracellular domain comprises a β chain variable region CDR1 comprising the amino acid sequence set forth in SEQ ID NO:4, a β chain variable region CDR2 comprising the amino acid sequence set forth in SEQ ID NO: 5, and a β chain variable region CDR3 comprising the amino acid sequence set forth in SEQ ID NO: 6. In certain embodiments, the extracellular domain comprises an α chain variable region CDR1 comprising the amino acid sequence set forth in SEQ ID NO: 1 or a conservative modification thereof, an α chain variable region CDR2 comprising the amino acid sequence set forth in SEQ ID NO: 2 or a conservative modification thereof, an α chain variable region CDR3 comprising the amino acid sequence set forth in SEQ ID NO: 3, a conservative modification of SEQ ID NO: 3, a β chain variable region CDR1 comprising the amino acid sequence set forth in SEQ ID NO: 4 or a conservative modification thereof, a β chain variable region CDR2 comprising the amino acid sequence set forth in SEQ ID NO: 5 or a conservative modification thereof, and a β chain variable region CDR3 comprising the amino acid sequence set forth in SEQ ID NO: 6 or a conservative modification thereof. In certain embodiments, the extracellular domain comprises an α chain variable region CDR1 comprising the amino acid sequence set forth in SEQ ID NO: 1, an α chain variable region CDR2 comprising the amino acid sequence set forth in SEQ ID NO: 2, an α chain variable region CDR3 comprising the amino acid sequence set forth in SEQ ID NO: 3, a β chain variable region CDR1 comprising the amino acid sequence set forth in SEQ ID NO: 4, a β chain variable region CDR2 comprising the amino acid sequence set forth in SEQ ID NO: 5, and a β chain variable region CDR3 comprising the amino acid sequence set forth in SEQ ID NO: 6.

In certain embodiments, the TCR is a human TCR and specifically binds to a mutant PIK3CA peptide (e.g., a human mutant PIK3CA peptide), which is designated as "RC8-2".

In certain embodiments, the TCR is a human TCR, which comprises an α chain comprising the amino acid sequence set forth in SEQ ID NO: 19 and/or a β chain comprising the amino acid sequence set forth in SEQ ID NO: 20. SEQ ID NOS: 19 and 20 are provided in Table 2.

In certain embodiments, the extracellular domain of the TCR comprises an α chain variable region and a β chain variable region or CDRs selected from Table 2. In certain embodiments, the extracellular domain comprises an α chain variable region comprising an amino acid sequence that is at least about 80% (e.g., at least about 85%, at least about 90%, or at least about 95%) homologous or identical to the amino acid sequence set forth in SEQ ID NO: 17, as shown in Table 2. For example, the extracellular domain comprises an α chain variable region comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous or identical to the amino acid sequence set forth in SEQ ID NO: 17. In certain embodiments, the extracellular domain comprises an α chain variable region comprising the amino acid sequence set forth in SEQ ID NO: 17. In certain embodiments, the extracellular domain comprises a β chain variable region comprising an amino acid sequence that is at least about 80% (e.g., at least about 85%, at least about 90%, or at least about 95%) homologous or identical to SEQ ID NO: 18, as

TABLE 1

| | RC8-1 | | |
|---|---|---|---|
| Antigen | PIK3CA H1047R/L | | |
| CDRs | 1 | 2 | 3 |
| α-chain | DSAIYN [SEQ ID NO: 1] | IQSSQRE [SEQ ID NO: 2] | CAVKGSDDYKLSF [SEQ ID NO: 3] |
| β-chain | KGHSH [SEQ ID NO: 4] | KGHSH [SEQ ID NO: 5] | CASSPVNLAGVSRADTQYF [SEQ ID NO: 6] |
| α-chain variable | METLLGLLILWLQLQWVSSKQEVTQIPAALSVPEGENLVLNCSFTDSA IYNLQWFRQDPGKGLTSLLLIQSSQREQTSGRLNASLDKSSGRSTLYIA ASQPGDSATYLCAVKGSDDYKLSFGAGTTVTVRA [SEQ ID NO: 7] | | |
| Full α-chain | METLLGLLILWLQLQWVSSKQEVTQIPAALSVPEGENLVLNCSFTDSA IYNLQWFRQDPGKGLTSLLLIQSSQREQTSGRL NASLDKSSGRSTLYIAASQPGDSATYLCAVKGSDDYKLSFGAGTTVT VRANIQNPEPAVYQLKDPRSQDSTLCLFTDFDSQINVP KTMESGTFITDKCVLDMKAMDSKSNGAIAWSNQTSFTCQDIFKETNA TYPSSDVPCDATLTEKSFETDMNLNFQNLLVIVLRILLL KVAGFNLLMTLRLWSS [SEQ ID NO: 9] | | |
| β-chain variable | MDTRVLCCAVICLLGAGLSNAGVMQNPRHLVRRGQEARLRCSPMK GHSHVYWYRQLPEEGLKFMVYLQKENIIDESGMPKERFSAEFPKEGP SILRIQQVVRGDSAAYFCASSPVNLAGVSRADTQYFGPGTRLTVL [SEQ ID NO: 8] | | |
| Full β-chain | MDTRVLCCAVICLLGAGLSNAGVMQNPRHLVRRGQEARLRCSPMK GHSHVYWYRQLPEEGLKFMVYLQKENIIDESGMPKE RFSAEFPKEGPSILRIQQVVRGDSAAYFCASSPVNLAGVSRADTQYFG PGTRLTVLEDLRNVTPPKVSLFEPSKAEIANKQKATLV CLARGFFPDHVELSWWVNGKEVHSGVCTDPQAYKESNYSYCLSSRL RVSATFWHNPRNHFRCQVQFHGLSEEDKWPEGSPK PVTQNISAEAWGRADCGITSASYQQGVLSATILYEILLGKATLYAVLV STLVVMAMVKRKNS [SEQ ID NO: 10] | | | shown in Table 2. For example, the extracellular domain comprises a β chain variable region comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous or identical to the amino acid sequence set forth in SEQ ID NO: 18. In certain embodiments, the extracellular domain comprises a β chain variable region comprising the amino acid sequence set forth in SEQ ID NO: 18. In certain embodiments, the extracellular domain comprises an α chain variable region comprising an amino acid sequence that is at least about 80% (e.g., at least about 85%, at least about 90%, or at least about 95%) homologous or identical to the amino acid sequence set forth in SEQ ID NO: 17, and a β chain variable region comprising an amino acid sequence that is at least about 80% (e.g., at least about 85%, at least about 90%, or at least about 95%) homologous or identical to the amino acid sequence set forth in SEQ ID NO: 18. In certain embodiments, the extracellular domain comprises an α chain variable region comprising the amino acid sequence set forth in SEQ ID NO: 17 and a β chain variable region comprising the amino acid sequence set forth in SEQ ID NO: 18. In certain embodiments, the extracellular domain comprises an α chain variable region CDR1 comprising the amino acid sequence set forth in SEQ ID NO: 11 or a conservative modification thereof, an α chain variable region CDR2 comprising the amino acid sequence set forth in SEQ ID NO: 12 or a conservative modification thereof, and an α chain variable region CDR3 comprising the amino acid sequence set forth in SEQ ID NO: 13 or a conservative modification thereof, as shown in Table 2. In certain embodiments, the extracellular domain comprises an α chain variable region CDR1 comprising the amino acid sequence set forth in SEQ ID NO: 11, an α chain variable region CDR2 comprising the amino acid sequence set forth in SEQ ID NO: 12, and an α chain variable region CDR3 comprising the amino acid sequence set forth in SEQ ID NO: 13. In certain embodiments, the extracellular domain comprises a β chain variable region CDR1 comprising the amino acid sequence set forth in SEQ ID NO: 14 or a conservative modification thereof, a β chain variable region CDR2 comprising the amino acid sequence set forth in SEQ ID NO: 15 or a conservative modification thereof, and a β chain variable region CDR3 comprising the amino acid sequence set forth in SEQ ID NO: 16 or a conservative modification thereof, as shown in Table 2. In certain embodiments, the extracellular domain comprises a β chain variable region CDR1 comprising the amino acid sequence set forth in SEQ ID NO: 14, a β chain variable region CDR2 comprising the amino acid sequence set forth in SEQ ID NO: 15, and a β chain variable region CDR3 comprising the amino acid sequence set forth in SEQ ID NO: 16. In certain embodiments, the extracellular domain comprises an α chain variable region CDR 1 comprising the amino acid sequence set forth in SEQ ID NO: 11 or a conservative modification thereof, an α chain variable region CDR2 comprising the amino acid sequence set forth in SEQ ID NO: 12 or a conservative modification thereof, an α chain variable region CDR3 comprising the amino acid sequence set forth in SEQ ID NO: 13 or a conservative modification thereof, a β chain variable region CDR1 comprising the amino acid sequence set forth in SEQ ID NO: 14 or a conservative modification thereof, a β chain variable region CDR2 comprising the amino acid sequence set forth in SEQ ID NO: 15 or a conservative modification thereof, and a β chain variable region CDR3 comprising the amino acid sequence set forth in SEQ ID NO: 16 or a conservative modification thereof. In certain embodiments, the extracellular domain comprises an α chain variable region CDR1 comprising the amino acid sequence set forth in SEQ ID NO: 11, an α chain variable region CDR2 comprising the amino acid sequence set forth in SEQ ID NO: 12, an α chain variable region CDR3 comprising the amino acid sequence set forth in SEQ ID NO: 13, a β chain variable region CDR1 comprising the amino acid sequence set forth in SEQ ID NO: 14, a β chain variable region CDR2 comprising the amino acid sequence set forth in SEQ ID NO: 15, and a β chain variable region CDR3 comprising the amino acid sequence set forth in SEQ ID NO: 16.

TABLE 2

| | RC8-2 | | |
|---|---|---|---|
| Antigen | | PIK3CA H1047R/L | |
| CDRs | 1 | 2 | 3 |
| α-chain | TSGFNG [SEQ ID NO: 11] | NVLDGL [SEQ ID NO: 12] | CAVTSWGKLQF [SEQ ID NO: 13] |
| β-chain | SGHTA [SEQ ID NO: 14] | FQGNSA [SEQ ID NO: 15] | CASSPRGYQPQHF [SEQ ID NO: 16] |
| α-chain variable | MWGVFLLYVSMKMGGTTGQNIDQPTEMTATEGAIVQINCTYQTSGFN GLFWYQQHAGEAPTFLSYNVLDGLEEKGRFSSFLSRSKGYSYLLLKEL QMKDSASYLCAVTSWGKLQFKLQFGAGTQVVVTP[SEQ ID NO: 17] | | |
| Full α-chain | MWGVFLLYVSMKMGGTTGQNIDQPTEMTATEGAIVQINCTYQTSGFN GLFWYQQHAGEAPTFLSYNVLDGLEEKGRFSSFLSRSK GYSYLLLKELQMKDSASYLCAVTSWGKLQFKLQFGAGTQVVVTPNIQ NPEPAVYQLKDPRSQDSTLCLFTDFDSQINVPKTMES GTFITDKCVLDMKAMDSKSNGAIAWSNQTSFTCQDIFKETNATYPSSD VPCDATLTEKSFETDMNLNFQNLLVIVLRILLLKVAGFN LLMTLRLWSS [SEQ ID NO: 19] | | |
| β-chain variable | MGTRLLFWVAFCLLGAYHTGAGVSQSPSNKVTEKGKDVELRCDPISGH TALYWYRQRLGQGLEFLIYFQGNSAPDKSGLPSDRFSAERTGESVSTLTI QRTQQEDSAVYLCASSPRGYQPQHFGDGTRLSIL [SEQ ID NO: 18] | | |

TABLE 2-continued

| RC8-2 | | | |
|---|---|---|---|
| Antigen | PIK3CA H1047R/L | | |
| CDRs | 1 | 2 | 3 |
| Full β-chain | MGTRLLFWVAFCLLGAYHTGAGVSQSPSNKVTEKGKDVELRCDPISGH TALYWYRQRLGQGLEFLIYFQGNSAPDKSGLPSDR FSAERTGESVSTLTIQRTQQEDSAVYLCASSPRGYQPQHFGDGTRLSILE DLRNVTPPKVSLFEPSKAEIANKQKATLVCLARGFF PDHVELSWWVNGKEVHSGVCTDPQAYKESNYSYCLSSRLRVSATFWH NPRNHFRCQVQFHGLSEEDKWPEGSPKPVTQNIS AEAWGRADCGITSASYQQGVLSATILYEILLGKATLYAVLVSTLVVMA MVKRKNS [SEQ ID NO: 20] | | |

In certain embodiments, the TCR is a human TCR and specifically binds to a mutant PIK3CA peptide polypeptide (e.g., a human mutant PIK3CA peptide polypeptide), which is designated as RC8-3.

In certain embodiments, the TCR is a human TCR, which comprises an α chain comprising the amino acid sequence set forth in SEQ ID NO: 29 and/or a β chain comprising the amino acid sequence set forth in SEQ ID NO: 30. SEQ ID NOS: 29 and 30 are provided in Table 3.

In certain embodiments, the extracellular domain of the TCR comprises an α chain variable region and a β chain variable region or CDRs selected from Table 3. In certain embodiments, the extracellular domain comprises an α chain variable region comprising an amino acid sequence that is at least about 80% (e.g., at least about 85%, at least about 90%, or at least about 95%) homologous or identical to the amino acid sequence set forth in SEQ ID NO: 27, as shown in Table 3. For example, the extracellular domain comprises an α chain variable region comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous or identical to the amino acid sequence set forth in SEQ ID NO: 27. In certain embodiments, the extracellular domain comprises an α chain variable region comprising the amino acid sequence set forth in SEQ ID NO: 27. In certain embodiments, the extracellular domain comprises a β chain variable region comprising an amino acid sequence that is at least about 80% (e.g., at least about 85%, at least about 90%, or at least about 95%) homologous or identical to the amino acid sequence set forth in SEQ ID NO: 28, as shown in Table 2. For example, the extracellular domain comprises a β chain variable region comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous or identical to the amino acid sequence set forth in SEQ ID NO: 28. In certain embodiments, the extracellular domain comprises a β chain variable region comprising the amino acid sequence set forth in SEQ ID NO: 28. In certain embodiments, the extracellular domain comprises an α chain variable region comprising an amino acid sequence that is at least about 80% (e.g., at least about 85%, at least about 90%, or at least about 95%) homologous to SEQ ID NO: 27, and a β chain variable region comprising an amino acid sequence that is at least about 80% (e.g., at least about 85%, at least about 90%, or at least about 95%) homologous or identical to the amino acid sequence set forth in SEQ ID NO: 28. In certain embodiments, the extracellular domain comprises an α chain variable region comprising the amino acid sequence set forth in SEQ ID NO: 27 and a β chain variable region comprising the amino acid sequence set forth in SEQ ID NO: 28. In certain embodiments, the extracellular domain comprises an α chain variable region CDR1 comprising the amino acid sequence set forth in SEQ ID NO: 21 or a conservative modification thereof, an α chain variable region CDR2 comprising the amino acid sequence set forth in SEQ ID NO: 22 or a conservative modification thereof, and an α chain variable region CDR3 comprising the amino acid sequence set forth in SEQ ID NO: 23 or a conservative modification thereof, as shown in Table 3. In certain embodiments, the extracellular domain comprises an α chain variable region CDR1 comprising the amino acid sequence set forth in SEQ ID NO: 21, an α chain variable region CDR2 comprising the amino acid sequence set forth in SEQ ID NO: 22, and an α chain variable region CDR3 comprising the amino acid sequence set forth in SEQ ID NO: 23. In certain embodiments, the extracellular domain comprises a β chain variable region CDR 1 comprising the amino acid sequence set forth in SEQ ID NO: 24 or a conservative modification thereof, a β chain variable region CDR2 comprising the amino acid sequence set forth in SEQ ID NO: 25 or a conservative modification thereof, and a β chain variable region CDR3 comprising the amino acid sequence set forth in SEQ ID NO: 26 or a conservative modification thereof, as shown in Table 3. In certain embodiments, the extracellular domain comprises a β chain variable region CDR1 comprising the amino acid sequence set forth in SEQ ID NO: 24, a β chain variable region CDR2 comprising the amino acid sequence set forth in SEQ ID NO: 25, and a β chain variable region CDR3 comprising the amino acid sequence set forth in SEQ ID NO: 26. In certain embodiments, the extracellular domain comprises an α chain variable region CDR1 comprising the amino acid sequence set forth in SEQ ID NO: 21 or a conservative modification thereof, an α chain variable region CDR2 comprising the amino acid sequence set forth in SEQ ID NO: 22 or a conservative modification thereof, an α chain variable region CDR3 comprising the amino acid sequence set forth in SEQ ID NO: 23 or a conservative modification thereof, a β chain variable region CDR1 comprising the amino acid sequence set forth in SEQ ID NO: 24 or a conservative modification thereof, a β chain variable region CDR2 comprising the amino acid sequence set forth in SEQ ID NO: 25 or a conservative modification thereof, and a β chain variable region CDR3 comprising the amino acid sequence set forth in SEQ ID NO: 26 or a conservative modification thereof. In certain embodiments, the extracellular domain comprises an α chain variable region CDR1 comprising the amino acid sequence set forth in SEQ ID NO: 21, an α chain variable region CDR2 comprising the amino acid sequence set forth in SEQ ID NO: 22, an α chain variable region CDR3 comprising the amino acid sequence set forth in SEQ ID NO: 23, a β chain variable region CDR1 comprising the amino acid sequence set forth in SEQ ID NO: 24, a β chain variable region CDR2 comprising the amino acid sequence set forth in SEQ ID NO: 25, and a β chain variable region CDR3 comprising the amino acid sequence set forth in SEQ ID NO: 26.

about 88%, about 89%, about 90%, about 91%, about 92%, about 93%, about 94%, about 95%, about 96%, about 97%, about 98%, or about 99% homologous or identical to the amino acid sequence set forth in SEQ ID NO: 37. In certain embodiments, the extracellular domain comprises an α chain variable region comprising the amino acid sequence set forth in SEQ ID NO: 37. In certain embodiments, the extracellular domain comprises a β chain variable region comprising an amino acid sequence that is at least about 80% (e.g., at least about 85%, at least about 90%, or at least about 95%) homologous or identical to the amino acid sequence set forth in SEQ ID NO: 38, as shown in Table 4.

TABLE 3

| | RC8-3 | | |
|---|---|---|---|
| Antigen | | PIK3CA H1047R/L | |
| CDRs | 1 | 2 | 3 |
| α-chain | TSDQSYG [SEQ ID NO: 21] | QGSYDEQN [SEQ ID NO: 22] | CAMREVLDNTDKLIF [SEQ ID NO: 23] |
| β-chain | KGHSH [SEQ ID NO: 24] | LQKENI [SEQ ID NO: 25] | CASSPPEAGLDTEAFF [SEQ ID NO: 26] |
| α-chain variable | MSLSSLLKVVTASLWLGPGIAQKITQTQPGMFVQEKEAVTLDCTYDT SDQSYGLFWYKQPSSGEMIFLIYQGSYDEQNATEGRYSLNFQKARKS ANLVISASQLGDSAMYFCAMREVLDNTDKLIFGTGTRLQVFP [SEQ ID NO: 27] | | |
| Full α-chain | MSLSSLLKVVTASLWLGPGIAQKITQTQPGMFVQEKEAVTLDCTYDT SDQSYGLFWYKQPSSGEMIFLIYQGSYDEQNATEGRYSLNFQKARKS ANLVISASQLGDSAMYFCAMREVLDNTDKLIFGTGTRLQVFPNIQNPE PAVYQLKDPRSQDSTLCLFTDFDSQINVPKTMESGTFITDKCVLDMK AMDSKSNGAIAWSNQTSFTCQDIFKETNATYPSSDVPCDATLTEKSFE TDMNLNFQNLLVIVLRILLLKVAGFNLLMTLRLWSS [SEQ ID NO: 29] | | |
| β-chain variable | MDTRVLCCAVICLLGAGLSNAGVMQNPRHLVRRRGQEARLRCSPMK GHSHVYWYRQLPEEGLKFMVYLQKENIIDESGMPKERFSAEFPKEGP SILRIQQVVRGDSAAYFCASSPPEAGLDTEAFFGQGTRLTVV [SEQ ID NO: 28] | | |
| Full β-chain | MDTRVLCCAVICLLGAGLSNAGVMQNPRHLVRRRGQEARLRCSPMK GHSHVYWYRQLPEEGLKFMVYLQKENIIDESGMPKERFSAEFPKEGP SILRIQQVVRGDSAAYFCASSPPEAGLDTEAFFGQGTRLTVVEDLRNV TPPKVSLFEPSKAEIANKQKATLVCLARGFFPDHVELSWWVNGKEVH SGVCTDPQAYKESNYSYCLSSRLRVSATFWHNPRNHFRCQVQFHGLS EEDKWPEGSPKPVTQNISAEAWGRADCGITSASYQQGVLSATILYEIL LGKATLYAVLVSTLVVMAMVKRKNS [SEQ ID NO: 30] | | |

In certain embodiments, the TCR is a human TCR and specifically binds to a mutant PIK3CA peptide polypeptide (e.g., a human mutant PIK3CA peptide polypeptide), which is designated as LB11-1.

In certain embodiments, the TCR is a human TCR, which comprises an α chain comprising the amino acid sequence set forth in SEQ ID NO: 39 and a β chain comprising the amino acid sequence set forth in SEQ ID NO: 40. SEQ ID NOS: 39 and 40 are provided in Table 4.

In certain embodiments, the extracellular domain of the TCR comprises an α chain variable region and a β chain variable region or CDRs selected from Table 4. In certain embodiments, the extracellular domain comprises an α chain variable region comprising an amino acid sequence that is at least about 80% (e.g., at least about 85%, at least about 90%, or at least about 95%) homologous or identical to the amino acid sequence set forth in SEQ ID NO: 37, as shown in Table 2. For example, the extracellular domain comprises an α chain variable region comprising an amino acid sequence that is about 80%, about 81%, about 82%, about 83%, about 84%, about 85%, about 86%, about 87%, For example, the extracellular domain comprises a β chain variable region comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous or identical to the amino acid sequence set forth in SEQ ID NO: 38. In certain embodiments, the extracellular domain comprises a β chain variable region comprising the amino acid sequence set forth in SEQ ID NO: 38. In certain embodiments, the extracellular domain comprises an α chain variable region comprising an amino acid sequence that is at least about 80% (e.g., at least about 85%, at least about 90%, or at least about 95%) homologous or identical to the amino acid sequence set forth in SEQ ID NO: 37, and a β chain variable region comprising an amino acid sequence that is at least about 80% (e.g., at least about 85%, at least about 90%, or at least about 95%) homologous or identical to the amino acid sequence set forth in SEQ ID NO: 38. In certain embodiments, the extracellular domain comprises an α chain variable region comprising the amino acid sequence set forth in SEQ ID NO: 37 and a β chain variable region comprising the amino acid sequence set forth in SEQ ID NO: 38. In certain embodiments, the extracellular domain comprises an α chain variable region CDR1 comprising the amino acid sequence set forth in SEQ ID NO: 31 or a conservative modification thereof, an α chain variable region CDR2 comprising the amino acid sequence set forth in SEQ ID NO: 32 or a conservative modification thereof, and an α chain variable region CDR3 comprising the amino acid sequence set forth in SEQ ID NO: 33 or a conservative modification thereof, as shown in Table 4. In certain embodiments, the extracellular domain comprises an α chain variable region CDR1 comprising the amino acid sequence set forth in SEQ ID NO: 31, an α chain variable region CDR2 comprising the amino acid sequence set forth in SEQ ID NO: 32, and an α chain variable region CDR3 comprising the amino acid sequence set forth in SEQ ID NO: 33. In certain embodiments, the extracellular domain comprises a β chain variable region CDR1 comprising the amino acid sequence set forth in SEQ ID NO: 34 or a conservative modification thereof, a β chain variable region CDR2 comprising the amino acid sequence set forth in SEQ ID NO: 35 or a conservative modification thereof, and a β chain variable region CDR3 comprising the amino acid sequence set forth in SEQ ID NO: 36 or a conservative modification thereof, as shown in Table 4. In certain embodiments, the extracellular domain comprises a β chain variable region CDR1 comprising the amino acid sequence set forth in SEQ ID NO: 34, a β chain variable region CDR2 comprising the amino acid sequence set forth in SEQ ID NO: 35, and a β chain variable region CDR3 comprising the amino acid sequence set forth in SEQ ID NO: 36. In certain embodiments, the extracellular domain comprises an α chain variable region CDR1 comprising the amino acid sequence set forth in SEQ ID NO: 31 or a conservative modification thereof, an α chain variable region CDR2 comprising the amino acid sequence set forth in SEQ ID NO: 32 or a conservative modification thereof, an α chain variable region CDR3 comprising the amino acid sequence set forth in SEQ ID NO: 33 or a conservative modification thereof, a β chain variable region CDR1 comprising the amino acid sequence set forth in SEQ ID NO: 34 or a conservative modification thereof, a β chain variable region CDR2 comprising the amino acid sequence set forth in SEQ ID NO: 35 or a conservative modification thereof, and a β chain variable region CDR3 comprising the amino acid sequence set forth in SEQ ID NO: 36 or a conservative modification thereof. In certain embodiments, the extracellular domain comprises an α chain variable region CDR1 comprising the amino acid sequence set forth in SEQ ID NO: 31, an α chain variable region CDR2 comprising the amino acid sequence set forth in SEQ ID NO: 32, an α chain variable region CDR3 comprising the amino acid sequence set forth in SEQ ID NO: 33, a β chain variable region CDR1 comprising the amino acid sequence set forth in SEQ ID NO: 34, a β chain variable region CDR2 comprising the amino acid sequence set forth in SEQ ID NO: 35, and a β chain variable region CDR3 comprising the amino acid sequence set forth in SEQ ID NO: 36.

TABLE 4

| | LB11-1 | | |
|---|---|---|---|
| Antigen | PIK3CA H1047L | | |
| CDRs | 1 | 2 | 3 |
| α-chain | NSAFQY [SEQ ID NO: 31] | TYSSGN [SEQ ID NO: 32] | CAMNSGGYQKVTF [SEQ ID NO: 33] |
| β-chain | DFQATT [SEQ ID NO: 34] | SNEGSKA [SEQ ID NO: 35] | CSAREQGPLEEQYF [SEQ ID NO: 36] |
| α-chain variable | MMKSLRVLLVILWLQLSWVWSQQKEVEQDPGPLSVPEGAIVSLNCT YSNSAFQYFMWYRQYSRKGPELLMYTYSSGNKEDGRFTAQVDKSSK YISLFIRDSQPSDSATYLCAMNSGGYQKVTFGIGTKLQVIP [SEQ ID NO: 37] | | |
| Full α-chain | MMKSLRVLLVILWLQLSWVWSQQKEVEQDPGPLSVPEGAIVSLNCT YSNSAFQYFMWYRQYSRKGPELLMYTYSSGNKEDGRFTAQVDKSSK YISLFIRDSQPSDSATYLCAMNSGGYQKVTFGIGTKLQVIPNIQNPEPA VYQLKDPRSQDSTLCLFTDFDSQINVPKTMESGTFITDKCVLDMKAM DSKSNGAIAWSNQTSFTCQDIFKETNATYPSSDVPCDATLTEKSFE TDMNLNFQNLLVIVLRILLLKVAGFNLLMTLRLWSS [SEQ ID NO: 39] | | |
| β-chain variable | MLLLLLLLGPAGSGLGAVVSQHPSRVICKSGTSVKIECRSLDFQATTM FWYRQFPKQSLMLMATSNEGSKATYEQGVEKDKFLINHASLTLSTLT VTSAHPEDSSFYICSACSAREQGPLEEQYFGPGTRLTVT [SEQ ID NO: 38] | | |
| Full β-chain | MLLLLLLLGPAGSGLGAVVSQHPSRVICKSGTSVKIECRSLDFQATTM FWYRQFPKQSLMLMATSNEGSKATYEQGVEKDKFLINHASLTLSTLT VTSAHPEDSSFYICSACSAREQGPLEEQYFGPGTRLTVTEDLRNVTPP KVSLFEPSKAEIANKQKATLVCLARGFFPDHVELSWWVNGKEVHSG VCTDPQAYKESNYSYCLSSRLRVSATFWHNPRNHFRCQVQFHGLSEE DKWPEGSPKPVTQNISAEAWGRADCGITSASYQQGVLSATILYEILLG KATLYAVLVSTLVVMAMVKRKNS [SEQ ID NO: 40] | | |

In certain embodiments, the TCR is a human TCR and specifically binds to a mutant PIK3CA peptide polypeptide (e.g., a human mutant PIK3CA peptide polypeptide), which is designated as LB11-2.

In certain embodiments, the TCR is a human TCR, which comprises an α chain comprising the amino acid sequence set forth in SEQ ID NO: 49 and a β chain comprising the amino acid sequence set forth in SEQ ID NO: 50. SEQ ID NOS: 49 and 50 are provided in Table 5.

In certain embodiments, the extracellular domain of the TCR comprises an α chain variable region and a β chain variable region or CDRs selected from Table 5. In certain embodiments, the extracellular domain comprises an α chain variable region comprising an amino acid sequence that is at least about 80% (e.g., at least about 85%, at least about 90%, or at least about 95%) homologous or identical to the amino acid sequence set forth in SEQ ID NO: 47, as shown in Table 5. For example, the extracellular domain comprises an α chain variable region comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous or identical to the amino acid sequence set forth in SEQ ID NO: 47. In certain embodiments the extracellular domain comprises an α chain variable region comprising the amino acid sequence set forth in SEQ ID NO: 47. In certain embodiments, the extracellular domain comprises a β chain variable region comprising an amino acid sequence that is at least about 80% (e.g., at least about 85%, at least about 90%, or at least about 95%) homologous or identical to the amino acid sequence set forth in SEQ ID NO: 48, as shown in Table 5. For example, the extracellular domain comprises a β chain variable region comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous or identical to the amino acid sequence set forth in SEQ ID NO: 48. In certain embodiments, the extracellular domain comprises a β chain variable region comprising the amino acid sequence set forth in SEQ ID NO: 48. In certain embodiments, the extracellular domain comprises an α chain variable region comprising an amino acid sequence that is at least about 80% (e.g., at least about 85%, at least about 90%, or at least about 95%) homologous or identical to the amino acid sequence set forth in SEQ ID NO: 47, and a β chain variable region comprising an amino acid sequence that is at least about 80% (e.g., at least about 85%, at least about 90%, or at least about 95%) homologous or identical to the amino acid sequence set forth in SEQ ID NO: 48. In certain embodiments, the extracellular domain comprises an α chain variable region comprising the amino acid sequence set forth in SEQ ID NO: 47 and a β chain variable region comprising the amino acid sequence set forth in SEQ ID NO: 48. In certain embodiments, the extracellular domain comprises an α chain variable region CDR1 comprising the amino acid sequence set forth in SEQ ID NO: 41 or a conservative modification thereof, an α chain variable region CDR2 comprising the amino acid sequence set forth in SEQ ID NO: 42 or a conservative modification thereof, and an α chain variable region CDR3 comprising the amino acid sequence set forth in SEQ ID NO: 43 or a conservative modification thereof, as shown in Table 5. In certain embodiments, the extracellular domain comprises an α chain variable region CDR1 comprising the amino acid sequence set forth in SEQ ID NO: 41, an α chain variable region CDR2 comprising the amino acid sequence set forth in SEQ ID NO: 42, and an α chain variable region CDR3 comprising the amino acid sequence set forth in SEQ ID NO: 43. In certain embodiments, the extracellular domain comprises a β chain variable region CDR1 comprising the amino acid sequence set forth in SEQ ID NO: 44 or a conservative modification thereof, a β chain variable region CDR2 comprising the amino acid sequence set forth in SEQ ID NO: 45 or a conservative modification thereof, and a β chain variable region CDR3 comprising the amino acid sequence set forth in SEQ ID NO: 46 or a conservative modification thereof, as shown in Table 5. In certain embodiments, the extracellular domain comprises a β chain variable region CDR1 comprising the amino acid sequence set forth in SEQ ID NO: 44, a β chain variable region CDR2 comprising the amino acid sequence set forth in SEQ ID NO: 45, and a β chain variable region CDR3 comprising the amino acid sequence set forth in SEQ ID NO: 46. In certain embodiments, the extracellular domain comprises an α chain variable region CDR1 comprising the amino acid sequence set forth in SEQ ID NO: 41 or a conservative modification thereof, an α chain variable region CDR2 comprising the amino acid sequence set forth in SEQ ID NO: 42 or a conservative modification thereof, an α chain variable region CDR3 comprising the amino acid sequence set forth in SEQ ID NO: 43 or a conservative modification thereof, a β chain variable region CDR1 comprising the amino acid sequence set forth in SEQ ID NO: 44 or a conservative modification thereof, a β chain variable region CDR2 comprising the amino acid sequence set forth in SEQ ID NO: 45 or a conservative modification thereof, and a β chain variable region CDR3 comprising the amino acid sequence set forth in SEQ ID NO: 46 or a conservative modification thereof, as shown in Table 5. In certain embodiments, the extracellular domain comprises an α chain variable region CDR1 comprising the amino acid sequence set forth in SEQ ID NO: 41, an α chain variable region CDR2 comprising the amino acid sequence set forth in SEQ ID NO: 42, an α chain variable region CDR3 comprising the amino acid sequence set forth in SEQ ID NO: 43, a β chain variable region CDR1 comprising the amino acid sequence set forth in SEQ ID NO: 44, a β chain variable region CDR2 comprising the amino acid sequence set forth in SEQ ID NO: 45 or a conservative modification thereof, and a β chain variable region CDR3 comprising the amino acid sequence set forth in SEQ ID NO: 46.

TABLE 5

| | LB11-2 | | |
|---|---|---|---|
| Antigen | | PIK3CA H1047L | |
| CDRs | 1 | 2 | 3 |
| α-chain | TISGNEY [SEQ ID NO: 41] | GLKNN [SEQ ID NO: 42] | CIVRVAGSARQLTF [SEQ ID NO: 43] |
| β-chain | SGHDT [SEQ ID NO: 44] | YYEEEE [SEQ ID NO: 45] | CASSFGTATYEQYF [SEQ ID NO: 46] |

TABLE 5-continued

| LB11-2 | | | |
|---|---|---|---|
| Antigen | PIK3CA H1047L | | |
| CDRs | 1 | 2 | 3 |

α-chain variable MRLVARVTVFLTFGTIIDAKTTQPPSMDCAEGRAANLPCNHSTISGNE
YVYWYRQIHSQGPQYIIHGLKNNETNEMASLIITEDRKSSTLILPHATLR
DTAVYYCIVRVAGSARQLTFGSGTQLTVLP [SEQ ID NO: 47]

Full α-chain MRLVARVTVFLTFGTIIDAKTTQPPSMDCAEGRAANLPCNHSTISGNE
YVYWYRQIHSQGPQYIIHGLKNNETNEMASLIITEDRKSSTLILPHATLR
DTAVYYCIVRVAGSARQLTFGSGTQLTVLPNIQNPEPAVYQLKDPRSQ
DSTLCLFTDFDSQINVPKTMESGTFITDKCVLDMKAMDSKSNGAIAWS
NQTSFTCQDIFKETNATYPSSDVPCDATLTEKSFETDMNLNFQNLLVIV
LRILLLKVAGFNLLMTLRLWSS
[SEQ ID NO: 49]

β-chain variable MGPGLLCWALLCLLGAGLVDAGVTQSPTHLIKTRGQQVTLRCSPKSG
HDTVSWYQQALGQGPQFIFQYYEEEERQRGNFPDRFSGHQFPNYSSEL
NVNALLLGDSALYLCASSFGTATYEQYFGPGTRLTVT [SEQ ID NO: 48]

Full β-chain MGPGLLCWALLCLLGAGLVDAGVTQSPTHLIKTRGQQVTLRCSPKSG
HDTVSWYQQALGQGPQFIFQYYEEEERQRGNFPDRFSGHQFPNYSSEL
NVNALLLGDSALYLCASSFGTATYEQYFGPGTRLTVTEDLRNVTPPKV
SLFEPSKAEIANKQKATLVCLARGFFPDHVELSWWVNGKEVHSGVCT
DPQAYKESNYSYCLSSRLRVSATFWHNPRNHFRCQVQFHGLSEEDKW
PEGSPKPVTQNISAEAWGRADCGITSASYQQGVLSATILYEILLGKATL
YAVLVSTLVVMAMVKRKNS [SEQ ID NO: 50]

In certain embodiments, the TCR is a human TCR and specifically binds to a mutant PIK3CA peptide polypeptide (e.g., a human mutant PIK3CA peptide polypeptide), which is designated as LB11-3.

In certain embodiments, the TCR is a human TCR, which comprises an α chain comprising the amino acid sequence set forth in SEQ ID NO: 59 and a β chain comprising the amino acid sequence set forth in SEQ ID NO: 60. SEQ ID NOS: 59 and 60 are provided in Table 6.

In certain embodiments, the extracellular domain of the TCR comprises an α chain variable region and a β chain variable region or CDRs selected from Table 6. In certain embodiments, the extracellular domain comprises an α chain variable region comprising an amino acid sequence that is at least about 80% (e.g., at least about 85%, at least about 90%, or at least about 95%) homologous or identical to the amino acid sequence set forth in SEQ ID NO: 57, as shown in Table 6. For example, the extracellular domain comprises an α chain variable region comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous or identical to the amino acid sequence set forth in SEQ ID NO: 57. In certain embodiments, the extracellular domain comprises an α chain variable region comprising the amino acid sequence set forth in SEQ ID NO: 57. In certain embodiments, the extracellular domain comprises a β chain variable region comprising an amino acid sequence that is at least about 80% (e.g., at least about 85%, at least about 90%, or at least about 95%) homologous or identical to the amino acid sequence set forth in SEQ ID NO: 58, as shown in Table 6. For example, the extracellular domain comprises a β chain variable region comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous or identical to the amino acid sequence set forth in SEQ ID NO: 58. In certain embodiments, the extracellular domain comprises a β chain variable region comprising the amino acid sequence set forth in SEQ ID NO: 58. In certain embodiments, the extracellular domain comprises an α chain variable region comprising an amino acid sequence that is at least about 80% (e.g., at least about 85%, at least about 90%, or at least about 95%) homologous or identical to the amino acid sequence set forth in SEQ ID NO: 57, and a β chain variable region comprising an amino acid sequence that is at least about 80% (e.g., at least about 85%, at least about 90%, or at least about 95%) homologous to SEQ ID NO: 58. In certain embodiments, the extracellular domain comprises an α chain variable region comprising the amino acid sequence set forth in SEQ ID NO: 57 and a β chain variable region comprising the amino acid sequence set forth in SEQ ID NO: 58. In certain embodiments, the extracellular domain comprises an α chain variable region CDR1 comprising the amino acid sequence set forth in SEQ ID NO: 51 or a conservative modification thereof, an α chain variable region CDR2 comprising the amino acid sequence set forth in SEQ ID NO: 52 or a conservative modification thereof, and an α chain variable region CDR3 comprising the amino acid sequence set forth in SEQ ID NO: 53 or a conservative modification thereof, as shown in Table 6. In certain embodiments, the extracellular domain comprises an α chain variable region CDR1 comprising the amino acid sequence set forth in SEQ ID NO: 51, an α chain variable region CDR2 comprising the amino acid sequence set forth in SEQ ID NO: 52, and an α chain variable region CDR3 comprising the amino acid sequence set forth in SEQ ID NO: 53. In certain embodiments, the extracellular domain comprises a β chain variable region CDR1 comprising the amino acid sequence set forth in SEQ ID NO: 54 or a conservative modification thereof, a β chain variable region CDR2 comprising the amino acid sequence set forth in SEQ ID NO: 55 or a conservative modification thereof, and a β chain variable region CDR3 comprising the amino acid sequence set forth in SEQ ID NO: 56 or a conservative modification thereof, as shown in Table 6. In certain embodiments, the extracellular domain comprises a β chain variable region CDR1 comprising the amino acid sequence set forth in SEQ ID NO: 54, a β chain variable region CDR2 comprising the amino acid sequence set forth in SEQ ID NO: 55, and a β chain variable region CDR3 comprising the amino acid sequence set forth in SEQ ID NO: 56. In certain embodiments, the extracellular domain comprises an α chain variable region CDR1 comprising the amino acid sequence set forth in SEQ ID NO: 51 or a conservative modification thereof, an α chain variable region CDR2 comprising the amino acid sequence set forth in SEQ ID NO: 52 or a conservative modification thereof, an α chain variable region CDR3 comprising the amino acid sequence set forth in SEQ ID NO: 53 or a conservative modification thereof, a β chain variable region CDR1 comprising the amino acid sequence set forth in SEQ ID NO: 54 or a conservative modification thereof, a β chain variable region CDR2 comprising the amino acid sequence set forth in SEQ ID NO: 55 or a conservative modification thereof, and a β chain variable region CDR3 comprising the amino acid sequence set forth in SEQ ID NO: 56 or a conservative modification thereof. In certain embodiments, the extracellular domain comprises an α chain variable region CDR1 comprising the amino acid sequence set forth in SEQ ID NO: 51, an α chain variable region CDR2 comprising the amino acid sequence set forth in SEQ ID NO: 52, an α chain variable region CDR3 comprising the amino acid sequence set forth in SEQ ID NO: 53, a β chain variable region CDR1 comprising the amino acid sequence set forth in SEQ ID NO: 54, a β chain variable region CDR2 comprising the amino acid sequence set forth in SEQ ID NO: 55, and a β chain variable region CDR3 comprising the amino acid sequence set forth in SEQ ID NO: 56.

In certain embodiments, the TCR is a human TCR and specifically binds to a mutant PIK3CA peptide polypeptide (e.g., a human mutant PIK3CA peptide polypeptide), which is designated as LB11-4.

In certain embodiments, the TCR is a human TCR, which comprises an α chain comprising the amino acid sequence set forth in SEQ ID NO: 69 and a β chain comprising the amino acid sequence set forth in SEQ ID NO: 70. SEQ ID NOS: 69 and 70 are provided in Table 7.

In certain embodiments, the extracellular domain of the TCR comprises an α chain variable region and a β chain variable region or CDRs selected from Table 7. In certain embodiments, the extracellular domain comprises an α chain variable region comprising an amino acid sequence that is at least about 80% (e.g., at least about 85%, at least about 90%, or at least about 95%) homologous or identical to the amino acid sequence set forth in SEQ ID NO: 67, as shown in Table 7. For example, the extracellular domain comprises an α chain variable region comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous or identical to the amino acid sequence set forth in SEQ ID NO: 67. In certain embodiments, the extracellular domain comprises an α chain variable region comprising the amino acid sequence set forth in SEQ ID NO: 67. In certain embodiments, the extracellular domain comprises a β chain variable region comprising an amino acid sequence that is at least about 80% (e.g., at least about 85%, at least about 90%, or at least about 95%) homologous or identical to the amino acid sequence set forth in SEQ ID NO: 68, as shown in Table 7. For example, the extracellular domain comprises a β chain

TABLE 6

| | LB11-3 | | |
|---|---|---|---|
| Antigen | | PIK3CA H1047L | |
| CDRs | 1 | 2 | 3 |
| α-chain | DSASNY [SEQ ID NO: 51] | IRSNVGE [SEQ ID NO: 52] | CAASIPGTASKLTF [SEQ ID NO: 53] |
| β-chain | MNHEY [SEQ ID NO: 54] | SMNVEV [SEQ ID NO: 55] | CASSPYRQGSYGYTF [SEQ ID NO: 56] |
| α-chain variable | MTSIRAVFIFLWLQLDLVNGENVEQHPSTLSVQEGDSAVIKCTYSDSAS NYFPWYKQELGKGPQLIIDIRSNVGEKKDQRIAVTLNKTAKHFSLHITET QPEDSAVYFCAASIPGTASKLTFGTGTRLQVTL [SEQ ID NO: 57] | | |
| Full α-chain | MTSIRAVFIFLWLQLDLVNGENVEQHPSTLSVQEGDSAVIKCTYSDSAS NYFPWYKQELGKGPQLIIDIRSNVGEKKDQRIAVTLNKTAKHFSLHITET QPEDSAVYFCAASIPGTASKLTFGTGTRLQVTLNIQNPEPAVYQLKDPR SQDSTLCLFTDFDSQINVPKTMESGTFITDKCVLDMKAMDSKSNGAIA WSNQTSFTCQDIFKETNATYPSSDVPCDATLTEKSFETDMNLNFQNLLV IVLRILLLKVAGFNLL MTLRLWSS [SEQ ID NO: 59] | | |
| β-chain variable | MGPQLLGYVVLCLLGAGPLEAQVTQNPRYLITVTGKKLTVTCSQNMN HEYMSWYRQDPGLGLRQIYYSMNVEVTDKGDVPEGYKVSRKEKRNFP LILESPSPNQTSLYFCASSPYRQGSYGYTFGSGTRLTVV [SEQ ID NO: 58] | | |
| Full β-chain | MGPQLLGYVVLCLLGAGPLEAQVTQNPRYLITVTGKKLTVTCSQNMN HEYMSWYRQDPGLGLRQIYYSMNVEVTDKGDVPEGYKVSRKEKRNFP LILESPSPNQTSLYFCASSPYRQGSYGYTFGSGTRLTVVEDLRNVTPPKV SLFEPSKAEIANKQKATLVCLARGFFPDHVELSWWVNGKEVHSGVCTD PQAYKESNYSYCLSSRLRVSATFWHNPRNHFRCQVQFHGLSEEDKWPE GSPKPVTQNISAEAWGRADCGITSASYQQGVLSATILYEILLGKATLYA VLVSTLVVMAMVKRKNS [SEQ ID NO: 60] | | | variable region comprising an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous or identical to the amino acid sequence set forth in the amino acid sequence set forth in SEQ ID NO: 68. In certain embodiments, the extracellular domain comprises a β chain variable region comprising the amino acid sequence set forth in SEQ ID NO: 68. In certain embodiments, the extracellular domain comprises an α chain variable region comprising an amino acid sequence that is at least about 80% (e.g., at least about 85%, at least about 90%, or at least about 95%) homologous or identical to the amino acid sequence set forth in SEQ ID NO: 67, and a β chain variable region comprising an amino acid sequence that is at least about 80% (e.g., at least about 85%, at least about 90%, or at least about 95%) homologous or identical to the amino acid sequence set forth in SEQ ID NO: 68. In certain embodiments, the extracellular domain comprises an α chain variable region comprising the amino acid sequence set forth in SEQ ID NO: 67 and a β chain variable region comprising the amino acid sequence set forth in SEQ ID NO: 68. In certain embodiments, the extracellular domain comprises an α chain variable region CDR1 comprising the amino acid sequence set forth in SEQ ID NO: 61 or a conservative modification thereof, an α chain variable region CDR2 comprising the amino acid sequence set forth in SEQ ID NO: 62 or a conservative modification thereof, and an α chain variable region CDR3 comprising the amino acid sequence set forth in SEQ ID NO: 63 or a conservative modification thereof, as shown in Table 7. In certain embodiments, the extracellular domain comprises an α chain variable region CDR1 comprising the amino acid sequence set forth in SEQ ID NO: 61, an α chain variable region CDR2 comprising the amino acid sequence set forth in SEQ ID NO: 62, and an α chain variable region CDR3 comprising the amino acid sequence set forth in SEQ ID NO: 63. In certain embodiments, the extracellular domain comprises a β chain variable region CDR1 comprising the amino acid sequence set forth in SEQ ID NO: 64 or a conservative modification thereof, a β chain variable region CDR2 comprising the amino acid sequence set forth in SEQ ID NO: 65 or a conservative modification thereof, and a β chain variable region CDR3 comprising the amino acid sequence set forth in SEQ ID NO: 66 or a conservative modification thereof, as shown in Table 7. In certain embodiments, the extracellular domain comprises a β chain variable region CDR1 comprising the amino acid sequence set forth in SEQ ID NO: 64, a β chain variable region CDR2 comprising the amino acid sequence set forth in SEQ ID NO: 65, and a β chain variable region CDR3 comprising the amino acid sequence set forth in SEQ ID NO: 66. In certain embodiments, the extracellular domain comprises an α chain variable region CDR1 comprising the amino acid sequence set forth in SEQ ID NO: 61 or a conservative modification thereof, an α chain variable region CDR2 comprising the amino acid sequence set forth in SEQ ID NO: 62 or a conservative modification thereof, an α chain variable region CDR3 comprising the amino acid sequence set forth in SEQ ID NO: 63 or a conservative modification thereof, a β chain variable region CDR1 comprising the amino acid sequence set forth in SEQ ID NO: 64 or a conservative modification thereof, a β chain variable region CDR2 comprising the amino acid sequence set forth in SEQ ID NO: 65 or a conservative modification thereof, and a β chain variable region CDR3 comprising the amino acid sequence set forth in SEQ ID NO: 66 or a conservative modification thereof. In certain embodiments, the extracellular domain comprises an α chain variable region CDR1 comprising the amino acid sequence set forth in SEQ ID NO: 61, an α chain variable region CDR2 comprising the amino acid sequence set forth in SEQ ID NO: 62, an α chain variable region CDR3 comprising the amino acid sequence set forth in SEQ ID NO: 63, a β chain variable region CDR1 comprising the amino acid sequence set forth in SEQ ID NO: 64, a β chain variable region CDR2 comprising the amino acid sequence set forth in SEQ ID NO: 65, and a β chain variable region CDR3 comprising the amino acid sequence set forth in SEQ ID NO: 66.

TABLE 7

| | LB11-4 | | |
|---|---|---|---|
| Antigen | | PIK3CA H1047L | |
| CDRs | 1 | 2 | 3 |
| α-chain | NTAFDY [SEQ ID NO: 61] | IRPDVSE [SEQ ID NO: 62] | CAASTGNFNKFYF [SEQ ID NO: 63] |
| β-chain | SGHNS [SEQ ID NO: 64] | FNNNVP [SEQ ID NO: 65] | CASNRQGTVTEAFF [SEQ ID NO: 66] |
| α-chain variable | MDKILGASFLVLWLQLCWVSGQQKEKSDQQQVKQSPQSLIVQKGGISII NCAYENTAFDYFPWYQQFPGKGPALLIAIRPDVSEKKEGRFTISFNKSA KQFSLHIMDSQPGDSATYFCAASTGNFNKFYFGSGTKLNVKP [SEQ ID NO: 67] | | |
| Full α-chain | MDKILGASFLVLWLQLCWVSGQQKEKSDQQQVKQSPQSLIVQKGGISII NCAYENTAFDYFPWYQQFPGKGPALLIAIRPDVSEKKEGRFTISFNKSA KQFSLHIMDSQPGDSATYFCAASTGNFNKFYFGSGTKLNVKPNIQNPEP AVYQLKDPRSQDSTLCLFTDFDSQINVPKTMESGTFITDKCVLDMKAM DSKSNGAIAWSNQTSFTCQDIFKETNATYPSSDVPCDATLTEKSFETDM NLNFQNLLVIVLRILLLKVAGFNLLMTLRLWSS [SEQ ID NO: 69] | | |
| β-chain variable | MDSWTFCCVSLCILVAKHTDAGVIQSPRHEVTEMGQEVTLRCKPISGH NSLFWYRQTMMRGLELLIYFNNNVPIDDSGMPEDRFSAKMPNASFSTL KIQPSEPRDSAVYFCASNRQGTVTEAFFGQGTRLTVV [SEQ ID NO: 68] | | |

TABLE 7-continued

LB11-4

| Antigen | | PIK3CA H1047L | |
|---|---|---|---|
| CDRs | 1 | 2 | 3 |

| Full β-chain | MDSWTFCCVSLCILVAKHTDAGVIQSPRHEVTEMGQEVTLRCKPISGH<br>NSLFWYRQTMMRGLELLIYFNNNVPIDDSGMPEDRFSAKMPNASFSTL<br>KIQPSEPRDSAVYFCASNRQGTVTEAFFGQGTRLTVVEDLRNVTPPKVS<br>LFEPSKAEIANKQKATLVCLARGFFPDHVELSWWVNGKEVHSGVCTDP<br>QAYKESNYSYCLSSRLRVSATFWHNPRNHFRCQVQFHGLSEEDKWPEG<br>SPKPVTQNISAEAWGRADCGITSASYQQGVLSATILYEILLGKATLYAV<br>LVSTLVVMAMVKRKNS [SEQ ID NO: 70] |
|---|---|

In certain embodiments, the CDRs regions described above are delineated using the IMGT numbering system (accessible at www.imgt.org/IMGTScientificChart/Numbering/IMGTIGVLsuperfamily.html, www.imgt.org/IMGTindex/numbering.php).

As used herein, the term "a conservative sequence modification" refers to an amino acid modification that does not significantly affect or alter the binding characteristics of the presently disclosed TCR comprising the amino acid sequence. Conservative modifications can include amino acid substitutions, additions and deletions. Amino acids can be classified into groups according to their physicochemical properties such as charge and polarity. Conservative amino acid substitutions are ones in which the amino acid residue is replaced with an amino acid within the same group. For example, amino acids can be classified by charge: positively-charged amino acids include lysine, arginine, histidine, negatively-charged amino acids include aspartic acid, glutamic acid, neutral charge amino acids include alanine, asparagine, cysteine, glutamine, glycine, isoleucine, leucine, methionine, phenylalanine, proline, serine, threonine, tryptophan, tyrosine, and valine. In addition, amino acids can be classified by polarity: polar amino acids include arginine (basic polar), asparagine, aspartic acid (acidic polar), glutamic acid (acidic polar), glutamine, histidine (basic polar), lysine (basic polar), serine, threonine, and tyrosine; nonpolar amino acids include alanine, cysteine, glycine, isoleucine, leucine, methionine, phenylalanine, proline, tryptophan, and valine. Thus, one or more amino acid residues within a CDR region can be replaced with other amino acid residues from the same group and the altered TCR can be tested for retained function (i.e., the functions set forth in (c) through (1) above) using the functional assays described herein. In certain embodiments, no more than one, no more than two, no more than three, no more than four, no more than five residues within a specified sequence or a CDR region are altered.

In certain embodiments, the α chain variable region and/or the β chain variable region amino acid sequences have at least about 80%, at least about 85%, at least about 90%, or at least about 95% (e.g., about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%) homology or identity to the specified sequences (e.g., SEQ ID NOs: 7, 8, 17, 18, 27, 28, 37, 38, 47, 48, 57, 58, 67 and 68) contain substitutions (e.g., conservative substitutions), insertions, or deletions relative to the specified sequence(s), but retain the ability to bind to a mutant PIK3CA peptide (e.g., a human mutant PIK3CA peptide).

In certain embodiments, the extracellular domain specifically binds to a mutant PIK3CA peptide (e.g., a human mutant PIK3CA peptide) and not the corresponding wild-type peptide sequence.

In certain embodiments, a total of 1 to 10 amino acids are substituted, inserted and/or deleted in SEQ ID NOs: 7, 8, 17, 18, 27, 28, 37, 38, 47, 48, 57, 58, 67 or 68. In certain embodiments, substitutions, insertions, or deletions occur in regions outside the CDRs of the extracellular domain. In certain embodiments, the extracellular domain comprises an α chain variable region and/or a β chain variable region sequence selected from the group consisting of SEQ ID NOs: 7, 8, 17, 18, 27, 28, 37, 38, 47, 48, 57, 58, 67 and 68, including post-translational modifications of that sequence (SEQ ID NO: 7, 8, 17, 18, 27, 28, 37, 38, 47, 48, 57, 58, 67 or 68).

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm.

The percent homology between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent homology between two amino acid sequences can be determined using the Needleman and Wunsch (J. Mol. Biol. 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the amino acids sequences of the presently disclosed subject matter can further be used as a "query sequence" to perform a search against public databases to, for example, identify related sequences. Such searches can be performed using the XBLAST program (version 2.0) of Altschul, et al. (1990) J. Mol. Biol. 215: 403-10. BLAST protein searches can be performed with the XBLAST program, score=50, wordlength=3 to obtain amino acid sequences homologous to the specified sequences disclosed herein. To obtain gapped alignments for comparison purposes, Gapped BLAST can be utilized as described in Altschul et al., (1997) Nucleic Acids Res. 25

(17): 3389-3402. When utilizing BLAST and Gapped BLAST programs, the default parameters of the respective programs (e.g., XBLAST and NBLAST) can be used.

In certain embodiments, the extracellular domain binds to the same epitope on a mutant PIK3CA peptide (e.g., a human mutant PIK3CA peptide) as the reference TCR. For example, the extracellular domain of a presently disclosed TCR binds to the same epitope on a mutant PIK3CA peptide (e.g., a human mutant PIK3CA peptide) as a reference TCR or a functional fragment thereof comprising the an α chain variable region CDR1, CDR2, and CDR3 sequences and the a β chain variable region CDR1, CDR2, and CDR3 sequences of, for example, any one of the presently disclosed TCRs (e.g., RC8-1, RC8-2, RC8-3, LB11-1, LB11-2, LB11-3 and LB11-4). In certain embodiments, the extracellular domain of a presently disclosed TCR binds to the same epitope on a mutant PIK3CA peptide (e.g., a human mutant PIK3CA peptide) as a reference TCR or a functional fragment thereof comprising the an α chain variable region and a β chain variable region sequences of, for example, any one of the presently disclosed TCRs (e.g., RC8-1, RC8-2, RC8-3, LB11-1, LB11-2, LB11-3 and LB11-4).

It is well known in the art that the CDR3 domain, independently from the CDR1 and/or CDR2 domain(s), alone can determine the binding specificity of a TCR or a functional fragment thereof, for a cognate antigen and that multiple TCRs can predictably be generated having the same binding specificity based on a common CDR3 sequence.

In certain embodiments, the extracellular domain comprises an α chain variable region CDR3 comprising the amino acid sequence set forth in SEQ ID NOS: 3, 13, 23, 33, 43, 53, 63 or a conservative modification thereof, and a β chain variable region CDR3 comprising the amino acid sequence set forth in SEQ ID NOS: 6, 16, 26, 36, 46, 56, 66 or a conservative modification thereof.

In certain embodiments, the extracellular domain comprises an α chain variable region CDR3 comprising the amino acid sequence set forth in SEQ ID NO: 3 or a conservative modification thereof; and a β chain variable region CDR3 comprising the amino acid sequence set forth in SEQ ID NO: 6 or a conservative modification thereof.

In certain embodiments, the extracellular domain comprises an α chain variable region CDR3 comprising the amino acid sequence set forth in SEQ ID NO: 13 or a conservative modification thereof; and a β chain variable region CDR3 comprising the amino acid sequence set forth in SEQ ID NO: 16 or a conservative modification thereof.

In certain embodiments, the extracellular domain comprises an α chain variable region CDR3 comprising the amino acid sequence set forth in SEQ ID NO: 23 or a conservative modification thereof; and a β chain variable region CDR3 comprising the amino acid sequence set forth in SEQ ID NO: 26 or a conservative modification thereof.

In certain embodiments, the extracellular domain comprises an α chain variable region CDR3 comprising the amino acid sequence set forth in SEQ ID NO: 33 or a conservative modification thereof; and a β chain variable region CDR3 comprising the amino acid sequence set forth in SEQ ID NO: 36 or a conservative modification thereof.

In certain embodiments, the extracellular domain comprises an α chain variable region CDR3 comprising the amino acid sequence set forth in SEQ ID NO: 43 or a conservative modification thereof; and a β chain variable region CDR3 comprising the amino acid sequence set forth in SEQ ID NO: 46 or a conservative modification thereof.

In certain embodiments, the extracellular domain comprises an α chain variable region CDR3 comprising the amino acid sequence set forth in SEQ ID NO: 53 or a conservative modification thereof; and a β chain variable region CDR3 comprising the amino acid sequence set forth in SEQ ID NO: 56 or a conservative modification thereof.

In certain embodiments, the extracellular domain comprises an α chain variable region CDR3 comprising the amino acid sequence set forth in SEQ ID NO: 63 or a conservative modification thereof; and a β chain variable region CDR3 comprising the amino acid sequence set forth in SEQ ID NO: 66 or a conservative modification thereof.

The extracellular domain can further comprise an α chain variable region CDR2 comprising the amino acid sequence set forth in SEQ ID NOS: 2, 12, 22, 32, 42, 52, 62 or a conservative modification thereof; and a β chain variable region CDR2 comprising the amino acid sequence set forth in SEQ ID NOS: 5, 15, 25, 35, 45, 55, 65 or a conservative modification thereof.

In certain embodiments, the extracellular domain comprises an α chain variable region CDR2 comprising the amino acid sequence set forth in SEQ ID NO: 2 or a conservative modification thereof; and a β chain variable region CDR2 comprising the amino acid sequence set forth in SEQ ID NO: 5 or a conservative modification thereof.

In certain embodiments, the extracellular domain comprises an α chain variable region CDR2 comprising the amino acid sequence set forth in SEQ ID NO: 12 or a conservative modification thereof; and a β chain variable region CDR2 comprising the amino acid sequence set forth in SEQ ID NO: 15 or a conservative modification thereof.

In certain embodiments, the extracellular domain comprises an α chain variable region CDR2 comprising the amino acid sequence set forth in SEQ ID NO: 22 or a conservative modification thereof; and a β chain variable region CDR2 comprising the amino acid sequence set forth in SEQ ID NO: 25 or a conservative modification thereof.

In certain embodiments, the extracellular domain comprises an α chain variable region CDR2 comprising the amino acid sequence set forth in SEQ ID NO: 32 or a conservative modification thereof; and a β chain variable region CDR2 comprising the amino acid sequence set forth in SEQ ID NO: 35 or a conservative modification thereof.

In certain embodiments, the extracellular domain comprises an α chain variable region CDR2 comprising the amino acid sequence set forth in SEQ ID NO: 42 or a conservative modification thereof; and a β chain variable region CDR2 comprising the amino acid sequence set forth in SEQ ID NO: 45 or a conservative modification thereof.

In certain embodiments, the extracellular domain comprises an α chain variable region CDR2 comprising the amino acid sequence set forth in SEQ ID NO: 52 or a conservative modification thereof; and a β chain variable region CDR2 comprising the amino acid sequence set forth in SEQ ID NO: 55 or a conservative modification thereof.

In certain embodiments, the extracellular domain comprises an α chain variable region CDR2 comprising the amino acid sequence set forth in SEQ ID NO: 62 or a conservative modification thereof; and a β chain variable region CDR2 comprising the amino acid sequence set forth in SEQ ID NO: 65 or a conservative modification thereof.

The extracellular domain can further comprise an α chain variable region CDR1 comprising the amino acid sequence set forth in SEQ ID NOS: 1, 11, 21, 31, 41, 51, 61 or a conservative modification thereof; and a β chain variable region CDR1 comprising the amino acid sequence set forth in SEQ ID NOS: 4, 14, 24, 34, 44, 54, 64 or a conservative modification thereof.

In certain embodiments, the extracellular domain comprises an α chain variable region CDR1 comprising the amino acid sequence set forth in SEQ ID NO: 1 or a conservative modification thereof; and a β chain variable region CDR1 comprising the amino acid sequence set forth in SEQ ID NO: 4 or a conservative modification thereof.

In certain embodiments, the extracellular domain comprises an α chain variable region CDR1 comprising the amino acid sequence set forth in SEQ ID NO: 11 or a conservative modification thereof; and a β chain variable region CDR1 comprising the amino acid sequence set forth in SEQ ID NO: 14 or a conservative modification thereof.

In certain embodiments, the extracellular domain comprises an α chain variable region CDR1 comprising the amino acid sequence set forth in SEQ ID NO: 21 or a conservative modification thereof; and a β chain variable region CDR1 comprising the amino acid sequence set forth in SEQ ID NO: 24 or a conservative modification thereof.

In certain embodiments, the extracellular domain comprises an α chain variable region CDR1 comprising the amino acid sequence set forth in SEQ ID NO: 31 or a conservative modification thereof; and a β chain variable region CDR1 comprising the amino acid sequence set forth in SEQ ID NO: 34 or a conservative modification thereof.

In certain embodiments, the extracellular domain comprises an α chain variable region CDR1 comprising the amino acid sequence set forth in SEQ ID NO: 41 or a conservative modification thereof; and a β chain variable region CDR1 comprising the amino acid sequence set forth in SEQ ID NO: 44 or a conservative modification thereof.

In certain embodiments, the extracellular domain comprises an α chain variable region CDR1 comprising the amino acid sequence set forth in SEQ ID NO: 51 or a conservative modification thereof; and a β chain variable region CDR1 comprising the amino acid sequence set forth in SEQ ID NO: 54 or a conservative modification thereof.

In certain embodiments, the extracellular domain comprises an α chain variable region CDR1 comprising the amino acid sequence set forth in SEQ ID NO: 61 or a conservative modification thereof; and a β chain variable region CDR1 comprising the amino acid sequence set forth in SEQ ID NO: 64 or a conservative modification thereof.

In some embodiments, the TCR of the presently disclosed subject matter can further comprise an inducible promoter, for expressing nucleic acid sequences in human cells. Promoters for use in expressing TCR genes can be a constitutive promoter, such as ubiquitin C (UbiC) promoter.

The presently disclosed subject matter also provides an isolated nucleic acid molecule encoding the mutant PIK3CA-targeted TCR described herein or a functional portion thereof. In certain embodiments, the isolated nucleic acid molecule encodes both an α chain and a β chain of a TCR. In certain embodiments, the α chain and the β chain are separated by a self-cleavage peptide, e.g., a 2A-peptide. In certain embodiments, the α chain and the β chain are separated by a furin-2A-peptide, e.g., a peptide set forth in SEQ ID NO: 84.

RAKRSGSGATNFSLLKQAGDVEENPGP [SEQ ID NO: 84]

In certain embodiments, the isolated nucleic acid molecule encodes a functional portion/fragment of a presently disclosed mutant PIK3CA-targeted TCR. As used herein, the term "functional portion" or "functional fragment" refers to any portion, part or fragment of a presently disclosed mutant PIK3CA-targeted TCR, which portion, part or fragment retains the biological activity of the mutant PIK3CA-targeted TCR (the parent TCR). For example, functional portions encompass the portions, parts or fragments of a presently disclosed mutant PIK3CA-targeted TCR that retains the ability to recognize a target cell, to treat a disease, e.g., breast cancer, to a similar, same, or even a higher extent as the parent TCR. In certain embodiments, an isolated nucleic acid molecule encoding a functional portion of a presently disclosed mutant PIK3CA-targeted TCR can encode a protein comprising, e.g., about 10%, about 20%, about 25%, about 30%, about 35%, about 40%, about 45%, about 50%, about 55%, about 60%, about 65%, about 70%, about 75%, about 80%, about 85%, about 90%, and about 95%, or more of the parent TCR.

TCRs with Modifications within CDRs

In certain embodiments, a presently disclosed TCR (or a functional fragment thereof) comprises an α chain variable region comprising CDR1, CDR2 and CDR3 sequences and a β chain variable region comprising CDR1, CDR2 and CDR3 sequences, wherein one or more of these CDR sequences comprise specified amino acid sequences based on the TCRs (or a functional fragments thereof) described herein (see Tables 1-7), or modifications thereof, and wherein the TCRs (or a functional fragments thereof) retain the desired functional properties of the mutant PIK3CA peptide-specific TCRs (or a functional fragments thereof) of the presently disclosed subject matter.

In certain embodiments, a presently disclosed TCR (or a functional fragment thereof) comprises an α chain constant region and a β chain constant region, wherein at least one of the constant regions comprises specified amino acid sequences based on the TCRs (or a functional fragments thereof) described herein (see Tables 1-7), or modifications thereof, and wherein the TCR (or a functional fragment thereof) retains the desired functional properties of the mutant PIK3CA peptide-specific TCRs (or a functional fragments thereof) of the presently disclosed subject matter.

In certain embodiments, such modifications do not significantly affect or alter the binding characteristics of the TCR containing the amino acid sequence. Non-limiting examples of such modifications include amino acid substitutions, additions and deletions. Modifications can be introduced into the presently disclosed TCR or a functional fragment thereof by standard techniques known in the art, such as site-directed mutagenesis and PCR-mediated mutagenesis.

The modifications can be conservative modifications, non-conservative modifications, or mixtures of conservative and non-conservative modifications. As discussed above, conservative amino acid substitutions are ones in which the amino acid residue is replaced with an amino acid residue having a similar side chain. Families of amino acid residues having similar side chains have been defined in the art. Exemplary conservative amino acid substitutions are shown in Table 8. In certain embodiments, amino acid substitutions may be introduced into a TCR of interest and the products screened for a desired activity, e.g., retained/improved antigen binding, decreased immunogenicity, or improved ADCC or CDC.

TABLE 8

| Original Residue | Exemplary conservative amino acid Substitutions |
| --- | --- |
| Ala (A) | Val; Leu; Ile |
| Arg (R) | Lys; Gln; Asn |
| Asn (N) | Gln; His; Asp, Lys; Arg |
| Asp (D) | Glu; Asn |

TABLE 8-continued

| Original Residue | Exemplary conservative amino acid Substitutions |
|---|---|
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe |
| Leu (L) | Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala |

Amino acids may be grouped according to common side-chain properties:
hydrophobic: Norleucine, Met, Ala, Val, Leu, Ile;
neutral hydrophilic: Cys, Ser, Thr, Asn, Gln;
acidic: Asp, Glu;
basic: His, Lys, Arg;
residues that influence chain orientation: Gly, Pro;
aromatic: Trp, Tyr, Phe.

In certain embodiments, one or more amino acid residues within a CDR region can be replaced with other amino acid residues from the same group and the altered TCR can be tested for retained function using the functional assays described herein.

Non-conservative substitutions entail exchanging a member of one of these classes for another class.

In certain embodiments, no more than one, no more than two, no more than three, no more than four, no more than five residues within a specified sequence or a CDR region are altered.

In certain embodiments, one or more amino acid residues within a constant region of a TCR can be modified to enhance stability and/or cell surface expression of the TCR. In certain embodiments, no more than one, no more than two, no more than three, no more than four, no more than five residues within a specified sequence or a constant region are altered. In certain embodiments, the modification includes but is not limited to, murinization, cysteine modification and transmembrane modification (see Cohen et al. Enhanced antitumor activity of murine-human hybrid T-cell receptor (TCR) in human lymphocytes is associated with improved pairing and TCR/CD3 stability, *Cancer Res.* 2006; 66 (17): 8878-8886; Cohen et al. Enhanced antitumor activity of T cells engineered to express T-cell receptors with a second disulfide bond, *Cancer Res.* 2007; 67 (8): 3898-3903; Kuball et al. Facilitating matched pairing and expression of TCR chains introduced into human T cells, *Blood* 2007; 109 (6): 2331-2338; Haga-Friedman et al. Incorporation of transmembrane hydrophobic mutations in the TCR enhance its surface expression and T cell functional avidity, *Journal of immunology* 2012; 188 (11): 5538-5546, the contents of each of which are incorporated by reference in their entireties).

In certain embodiments, a TCR disclosed herein comprises a modified TCR α-chain constant region that comprises an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous or identical to the amino acid sequence set forth in SEQ ID NO: 80 or 81. In certain embodiments, the modified TCR α-chain constant region comprises an amino acid sequence set forth in SEQ ID NO: 80. In certain embodiments, the modified TCR α-chain constant region comprises an amino acid sequence set forth in SEQ ID NO: 81.

In certain embodiments, a TCR disclosed herein comprises a modified TCR β-chain constant region that comprises an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% homologous or identical to the amino acid sequence set forth in SEQ ID NO: 82 or 83. In certain embodiments, the modified TCR β-chain constant region comprises an amino acid sequence set forth in SEQ ID NO: 82. In certain embodiments, the modified TCR β-chain constant region comprises an amino acid sequence set forth in SEQ ID NO: 83.

```
Human α-chain constant region:
                                      [SEQ ID NO: 80]
NIQNPDPAVYQLRDSKSSDKSVCLFTDFDSQTNVSQSKDSDVYITDKTVL

DMRSMDFKSNSAVAWSNKSDFACANAFNNSIIPEDTFFPSPESSCDVKLV

EKSFETDTNLNFQNLSVIGFRILLLKVAGFNLLMTLRLWSS

Mouse α-chain constant region:
(cysteine-modification and LVL modification in
transmembrane domain underlined)
                                      [SEQ ID NO: 81]
NIQNPEPAVYQLKDPRSQDSTLCLFTDFDSQINVPKTMESGTFITDKCVL

DMKAMDSKSNGAIAWSNQTSFTCQDIFKETNATYPSSDVPCDATLTEKSF

ETDMNLNFQNLLVIVLRILLLKVAGFNLLMTLRLWSS

Human β-chain constant region:
                                      [SEQ ID NO: 82]
EDLNKVFPPEVAVFEPSEAEISHTQKATLVCLATGFFPDHVELSWWVNGK

EVHSGVSTDPQPLKEQPALNDSRYCLSSRLRVSATFWQNPRNHFRCQVQF

YGLSENDEWTQDRAKPVTQIVSAEAWGRADCGFTSVSYQQGVLSATILYE

ILLGKATLYAVLVSALVLMAMVKRKDF

Mouse β-chain constant region:
(cysteine-modification underlined)
                                      [SEQ ID NO: 83]
EDLRNVTPPKVSLFEPSKAEIANKQKATLVCLARGFFPDHVELSWWVNGK

EVHSGVCTDPQAYKESNYSYCLSSRLRVSATFWHNPRNHFRCQVQFHGLS

EEDKWPEGSPKPVTQNISAEAWGRADCGITSASYQQGVLSATILYEILLG

KATLYAVLVSTLVVMAMVKRKNS
```

V. Immunoresponsive Cells

The presently disclosed subject matter provides cells comprising a TCR targeting a mutant PIK3CA peptide. Such cells are administered to a human subject in need thereof for treating and/or preventing a malignancy, e.g., breast cancer The presently disclosed subject matter provides immunoresponsive cells comprising a TCR that specifically binds to a mutant PIK3CA peptide (e.g., a human mutant PIK3CA peptide) as described above.

The immunoresponsive cells can be transduced with a presently disclosed TCR such that the cells express the TCR. The presently disclosed subject matter also provides methods of using such cells for the treatment of a malignancy, e.g., breast cancer.

The immunoresponsive cells of the presently disclosed subject matter can be cells of the lymphoid lineage. The lymphoid lineage, comprising B, T and natural killer (NK) cells, provides for the production of TCRs, regulation of the cellular immune system, detection of foreign agents in the blood, detection of cells foreign to the host, and the like. Non-limiting examples of immunoresponsive cells of the lymphoid lineage include T cells, Natural Killer (NK) cells, embryonic stem cells, and pluripotent stem cells (e.g., those from which lymphoid cells may be differentiated). T cells can be lymphocytes that mature in the thymus and are chiefly responsible for cell-mediated immunity. T cells are involved in the adaptive immune system. The T cells of the presently disclosed subject matter can be any type of T cells, including, but not limited to, T helper cells, cytotoxic T cells, memory T cells (including central memory T cells, stem-cell-like memory T cells (or stem-like memory T cells), and two types of effector memory T cells: e.g., $T_{EM}$ cells and $T_{EMRA}$ cells, Regulatory T cells (also known as suppressor T cells), Natural killer T cells, Mucosal associated invariant T cells, and γδ T cells. Cytotoxic T cells (CTL or killer T cells) are a subset of T lymphocytes capable of inducing the death of infected somatic or tumor cells. In certain embodiments, the TCR-expressing T cells express Foxp3 to achieve and maintain a T regulatory phenotype.

Natural killer (NK) cells can be lymphocytes that are part of cell-mediated immunity and act during the innate immune response. NK cells do not require prior activation in order to perform their cytotoxic effect on target cells.

The immunoresponsive cells of the presently disclosed subject matter can express a TCR that specifically binds to a mutant PIK3CA peptide (e.g., a human mutant PIK3CA peptide), for the treatment of cancer, e.g., breast cancer. Such immunoresponsive cells can be administered to a subject (e.g., a human subject) in need thereof for the treatment of cancer, e.g., breast cancer. In certain embodiments, the immunoresponsive cell is a T cell. The T cell can be a CD4$^+$ T cell or a CD8$^+$ T cell. In certain embodiments, the T cell is a CD4$^+$ T cell. In certain embodiments, the T cell is a CD8$^+$ T cell.

A presently disclosed immunoresponsive cell can further include at least one recombinant or exogenous co-stimulatory ligand. For example, a presently disclosed immunoresponsive cell can be further transduced with at least one co-stimulatory ligand, such that the immunoresponsive cell co-expresses or is induced to co-express the PIK3CA-targeted TCR and the at least one co-stimulatory ligand. The interaction between the PIK3CA-targeted TCR and at least one co-stimulatory ligand provides a non-antigen-specific signal important for full activation of an immunoresponsive cell (e.g., T cell). Co-stimulatory ligands include, but are not limited to, members of the tumor necrosis factor (TNF) superfamily, and immunoglobulin (Ig) superfamily ligands. TNF is a cytokine involved in systemic inflammation and stimulates the acute phase reaction. Its primary role is in the regulation of immune cells. Members of TNF superfamily share a number of common features. The majority of TNF superfamily members are synthesized as type II transmembrane proteins (extracellular C-terminus) containing a short cytoplasmic segment and a relatively long extracellular region. TNF superfamily members include, without limitation, nerve growth factor (NGF), CD40L (CD40L)/CD154, CD137L/4-1BBL, TNF-α, CD134L/OX40L/CD252, CD27L/CD70, Fas ligand (FasL), CD30L/CD153, tumor necrosis factor beta (TNFβ)/lymphotoxin-alpha (LTα), lymphotoxin-beta (LTβ), CD257/B cell-activating factor (BAFF)/Blys/THANK/Tall-1, glucocorticoid-induced TNF Receptor ligand (GITRL), and TNF-related apoptosis-inducing ligand (TRAIL), LIGHT (TNFSF14). The immunoglobulin (Ig) superfamily is a large group of cell surface and soluble proteins that are involved in the recognition, binding, or adhesion processes of cells. These proteins share structural features with immunoglobulins—they possess an immunoglobulin domain (fold). Immunoglobulin superfamily ligands include, but are not limited to, CD80 and CD86, both ligands for CD28, PD-L1/(B7-H1) that ligands for PD-1. In certain embodiments, the at least one co-stimulatory ligand is selected from the group consisting of 4-1BBL, CD80, CD86, CD70, OX40L, CD48, TNFRSF14, PD-L1, and combinations thereof. In certain embodiments, the immunoresponsive cell comprises one recombinant co-stimulatory ligand that is 4-1BBL. In certain embodiments, the immunoresponsive cell comprises two recombinant co-stimulatory ligands that are 4-1BBL and CD80.

Furthermore, a presently disclosed immunoresponsive cell can further comprise at least one exogenous cytokine. For example, a presently disclosed immunoresponsive cell can be further transduced with at least one cytokine, such that the immunoresponsive cell secretes the at least one cytokine as well as expresses the mutant PIK3CA-targeted TCR. In certain embodiments, the at least one cytokine is selected from the group consisting of IL-2, IL-3, IL-6, IL-7, IL-11, IL-12, IL-15, IL-17, and IL-21. In certain embodiments, the cytokine is IL-12.

The mutant PIK3CA peptide-specific or mutant PIK3CA-targeted human lymphocytes that can be used in peripheral donor lymphocytes, e.g., those disclosed in Sadelain, M., et al. 2003 *Nat Rev Cancer* 3:35-45 (disclosing peripheral donor lymphocytes genetically modified to express TCRs), in Morgan, R. A., et al. 2006 *Science* 314:126-129 (disclosing peripheral donor lymphocytes genetically modified to express a full-length tumor antigen-recognizing T cell receptor complex comprising the a and B heterodimer), in Panelli, M. C., et al. 2000 *J Immunol* 164:495-504; Panelli, M. C., et al. 2000 *J Immunol* 164:4382-4392 (disclosing lymphocyte cultures derived from tumor infiltrating lymphocytes (TILs) in tumor biopsies), and in Dupont, J., et al. 2005 *Cancer Res* 65:5417-5427; Papanicolaou, G. A., et al. 2003 *Blood* 102:2498-2505 (disclosing selectively in vitro-expanded antigen-specific peripheral blood leukocytes employing artificial antigen-presenting cells (AAPCs) or pulsed dendritic cells). The immunoresponsive cells (e.g., T cells) can be autologous, non-autologous (e.g., allogeneic), or derived in vitro from engineered progenitor or stem cells.

The unpurified source of CTLs may be any known in the art, such as the bone marrow, fetal, neonate or adult or other hematopoietic cell source, e.g., fetal liver, peripheral blood or umbilical cord blood. Various techniques can be employed to separate the cells. For instance, negative selection methods can remove non-CTLs initially.

A large proportion of terminally differentiated cells can be initially removed by a relatively crude separation. For example, magnetic bead separations can be used initially to remove large numbers of irrelevant cells. Preferably, at least about 80%, usually at least about 70% of the total hematopoietic cells will be removed prior to cell isolation.

Procedures for separation include, but are not limited to, density gradient centrifugation; resetting; coupling to particles that modify cell density; magnetic separation with TCR-coated magnetic beads; affinity chromatography; cytotoxic agents joined to or used in conjunction with a mAb, including, but not limited to, complement and cytotoxins; and panning with TCR attached to a solid matrix, e.g. plate, chip, elutriation or any other convenient technique.

Techniques for separation and analysis include, but are not limited to, flow cytometry, which can have varying degrees of sophistication, e.g., a plurality of color channels, low angle and obtuse light scattering detecting channels, impedance channels.

The cells can be selected against dead cells, by employing dyes associated with dead cells such as propidium iodide (PI). Preferably, the cells are collected in a medium comprising 2% fetal calf serum (FCS) or 0.2% bovine serum albumin (BSA) or any other suitable, preferably sterile, isotonic medium.

VI. Vectors

Genetic modification of immunoresponsive cells (e.g., T cells, NK cells) can be accomplished by transducing a substantially homogeneous cell composition with a recombinant DNA or RNA construct. The vector can be a retroviral vector (e.g., gamma retroviral), which is employed for the introduction of the DNA or RNA construct into the host cell genome. For example, a polynucleotide encoding the mutant PIK3CA-targeted TCR can be cloned into a retroviral vector and expression can be driven from its endogenous promoter, from the retroviral long terminal repeat, or from an alternative internal promoter.

Non-viral vectors or RNA may be used as well. Random chromosomal integration, or targeted integration (e.g., using a nuclease, transcription activator-like effector nucleases (TALENs), Zinc-finger nucleases (ZFNs), and/or clustered regularly interspaced short palindromic repeats (CRISPRs), or transgene expression (e.g., using a natural or chemically modified RNA) can be used.

For initial genetic modification of the cells to provide mutant PIK3CA-targeted TCR expressing cells, a retroviral vector is generally employed for transduction, however any other suitable viral vector or non-viral delivery system can be used. For subsequent genetic modification of the cells to provide cells comprising an antigen presenting complex comprising at least two co-stimulatory ligands, retroviral gene transfer (transduction) likewise proves effective. Combinations of retroviral vector and an appropriate packaging line are also suitable, where the capsid proteins will be functional for infecting human cells. Various amphotropic virus-producing cell lines are known, including, but not limited to, PA12 (Miller, et al. (1985) *Mol. Cell. Biol.* 5:431-437); PA317 (Miller, et al. (1986) *Mol. Cell. Biol.* 6:2895-2902); and CRIP (Danos, et al. (1988) *Proc. Natl. Acad. Sci. USA* 85:6460-6464). Non-amphotropic particles are suitable too, e.g., particles pseudotyped with VSVG, RD114 or GALV envelope and any other known in the art.

Possible methods of transduction also include direct co-culture of the cells with producer cells, e.g., by the method of Bregni, et al. (1992) *Blood* 80:1418-1422, or culturing with viral supernatant alone or concentrated vector stocks with or without appropriate growth factors and polycations, e.g., by the method of Xu, et al. (1994) *Exp. Hemat.* 22:223-230; and Hughes, et al. (1992) *J. Clin. Invest.* 89:1817.

Transducing viral vectors can be used to express a co-stimulatory ligand and/or secrets a cytokine (e.g., 4-1BBL and/or IL-12) in an immunoresponsive cell. Preferably, the chosen vector exhibits high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272: 263 267, 1996; and Miyoshi et al., Proc. Natl. Acad. Sci. U.S.A. 94:10319, 1997). Other viral vectors that can be used include, for example, adenoviral, lentiviral, and adeno-associated viral vectors, vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107: 77S-83S, 1995). Retroviral vectors are particularly well developed and have been used in clinical settings (Rosenberg et al., N. Engl. J. Med 323:370, 1990; Anderson et al., U.S. Pat. No. 5,399,346).

In certain non-limiting embodiments, the vector expressing a presently disclosed mutant PIK3CA-targeted TCR is a retroviral vector, e.g., an oncoretroviral vector.

Non-viral approaches can also be employed for the expression of a protein in cell. For example, a nucleic acid molecule can be introduced into a cell by administering the nucleic acid in the presence of lipofection (Feigner et al., Proc. Nat'l. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases or targeted nucleases (e.g., Zinc finger nucleases, meganucleases, or TALE nucleases). Transient expression may be obtained by RNA electroporation.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element or intron (e.g., the elongation factor 1α enhancer/promoter/intron structure). For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

The resulting cells can be grown under conditions similar to those for unmodified cells, whereby the modified cells can be expanded and used for a variety of purposes.

VII. Genomic Integration into Immunoresponsive Cell

In certain embodiments, a TCR can be integrated into a selected locus of the genome of an immunoresponsive cell. Any targeted genome editing methods can be used to integrate the TCR in selected loci of the genome of an immunoresponsive cell. In certain embodiments, the expression of the TCR is driven by an endogenous promoter/enhancer within or near the locus. In certain embodiments, the expression of the TCR is driven by an exogenous promoter integrated into the locus. The locus where the TCR is integrated is selected based on the expression level of the genes within the locus, and timing of the gene expression of the genes within the locus. The expression level and timing can vary under different stages of cell differentiation and mitogen/cytokine microenvironment, which are among the factors to be considered when making the selection.

In certain embodiments, the CRISPR system is used to integrate the TCR in selected loci of the genome of an immunoresponsive cell. Clustered regularly-interspaced short palindromic repeats (CRISPR) system is a genome editing tool discovered in prokaryotic cells. When utilized for genome editing, the system includes Cas9 (a protein able to modify DNA utilizing crRNA as its guide), CRISPR RNA (crRNA, contains the RNA used by Cas9 to guide it to the correct section of host DNA along with a region that binds to tracrRNA (generally in a hairpin loop form) forming an active complex with Cas9), trans-activating crRNA (tracrRNA, binds to crRNA and forms an active complex with Cas9), and an optional section of DNA repair template (DNA that guides the cellular repair process allowing insertion of a specific DNA sequence). CRISPR/Cas9 often employs a plasmid to transfect the target cells. The crRNA needs to be designed for each application as this is the sequence that Cas9 uses to identify and directly bind to the target DNA in a cell. The repair template carrying TCR expression cassette need also be designed for each application, as it must overlap with the sequences on either side of the cut and code for the insertion sequence. Multiple crRNA's and the tracrRNA can be packaged together to form a single-guide RNA (sgRNA). This sgRNA can be joined together with the Cas9 gene and made into a plasmid in order to be transfected into cells. Methods of using the CRISPR system are described, for example, in WO 2014093661 A2, WO 2015123339 A1 and WO 2015089354 A1, which are incorporated by reference in their entireties.

In certain embodiments, zinc-finger nucleases are used to integrate the TCR in selected loci of the genome of an immunoresponsive cell. A zinc-finger nuclease (ZFN) is an artificial restriction enzyme, which is generated by combining a zinc finger DNA-binding domain with a DNA-cleavage domain. A zinc finger domain can be engineered to target specific DNA sequences which allows a zinc-finger nuclease to target desired sequences within genomes. The DNA-binding domains of individual ZFNs typically contain a plurality of individual zinc finger repeats and can each recognize a plurality of basepairs. The most common method to generate new zinc-finger domain is to combine smaller zinc-finger "modules" of known specificity. The most common cleavage domain in ZFNs is the non-specific cleavage domain from the type IIs restriction endonuclease FokI. Using the endogenous homologous recombination (HR) machinery and a homologous DNA template carrying TCR expression cassette, ZFNs can be used to insert the TCR expression cassette into genome. When the targeted sequence is cleaved by ZFNs, the HR machinery searches for homology between the damaged chromosome and the homologous DNA template, and then copies the sequence of the template between the two broken ends of the chromosome, whereby the homologous DNA template is integrated into the genome. Methods of using the ZFN system are described, for example, in WO 2009146179 A1, WO 2008060510 A2 and CN 102174576 A, which are incorporated by reference in their entireties.

In certain embodiments, the TALEN system is used to integrate the TCR in selected loci of the genome of an immunoresponsive cell. Transcription activator-like effector nucleases (TALEN) are restriction enzymes that can be engineered to cut specific sequences of DNA. TALEN system operates on almost the same principle as ZENs. They are generated by combining a transcription activator-like effectors DNA-binding domain with a DNA cleavage domain. Transcription activator-like effectors (TALEs) are composed of 33-34 amino acid repeating motifs with two variable positions that have a strong recognition for specific nucleotides. By assembling arrays of these TALEs, the TALE DNA-binding domain can be engineered to bind desired DNA sequence, and thereby guide the nuclease to cut at specific locations in genome. Methods of using the TALEN system are described, for example, in WO 2014134412 A1, WO 2013163628 A2 and WO 2014040370 A1, which are incorporated by reference in their entireties.

Methods for delivering the genome editing agents can vary depending on the need. In certain embodiments, the components of a selected genome editing method are delivered as DNA constructs in one or more plasmids. In certain embodiments, the components are delivered via viral vectors. Common delivery methods include but is not limited to, electroporation, microinjection, gene gun, impalefection, hydrostatic pressure, continuous infusion, sonication, magnetofection, adeno-associated viruses, envelope protein pseudotyping of viral vectors, replication-competent vectors cis and trans-acting elements, herpes simplex virus, and chemical vehicles (e.g., oligonucleotides, lipoplexes, polymersomes, polyplexes, dendrimers, inorganic Nanoparticles, and cell-penetrating peptides).

Modification can be made anywhere within the selected locus, or anywhere that can influence gene expression of the integrated TCR. In certain embodiments, the modification is introduced upstream of the transcriptional start site of the integrated TCR. In certain embodiments, the modification is introduced between the transcriptional start site and the protein coding region of the integrated TCR) In certain embodiments, the modification is introduced downstream of the protein coding region of the integrated TCR.

VIII. Polypeptides and Analogs and Polynucleotides

Also included in the presently disclosed subject matter are TCRs that specifically binds to a mutant PIK3CA peptide (e.g., a human mutant PIK3CA peptide) functional fragments thereof, and polynucleotides encoding thereof that are modified in ways that enhance their anti-tumor activity when expressed in an immunoresponsive cell. The presently disclosed subject matter provides methods for optimizing an amino acid sequence or a nucleic acid sequence by producing an alteration in the sequence. Such alterations may comprise certain mutations, deletions, insertions, or post-translational modifications. The presently disclosed subject matter further comprises analogs of any naturally-occurring polypeptide of the presently disclosed subject matter. Analogs can differ from a naturally-occurring polypeptide of the presently disclosed subject matter by amino acid sequence differences, by post-translational modifications, or by both. Analogs of the presently disclosed subject matter can generally exhibit at least about 85%, about 90%, about 91%, about 92%, about 93%, about 94%, about 95%, about 96%, about 97%, about 98%, about 99% or more identity or homology with all or part of a naturally-occurring amino, acid sequence of the presently disclosed subject matter. The length of sequence comparison is at least about 5, about 10, about 15, about 20, about 25, about 50, about 75, about 100 or more amino acid residues. Again, in an exemplary approach to determining the degree of identity, a BLAST program may be used, with a probability score between e-3 and e-100 indicating a closely related sequence. Modifications comprise in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the presently disclosed subject matter by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., beta ($\beta$) or gamma ($\gamma$) amino acids.

In addition to full-length polypeptides, the presently disclosed subject matter also provides fragments of any one of the polypeptides or peptide domains of the presently disclosed subject matter. A fragment can be at least about 5, about 10, about 13, or about 15 amino acids. In some embodiments, a fragment is at least about 20 contiguous amino acids, at least about 30 contiguous amino acids, or at least about 50 contiguous amino acids. In some embodiments, a fragment is at least about 60 to about 80, about 100, about 200, about 300 or more contiguous amino acids. Fragments of the presently disclosed subject matter can be generated by methods known to those of ordinary skill in the art or may result from normal protein processing (e.g., removal of amino acids from the nascent polypeptide that are not required for biological activity or removal of amino acids by alternative mRNA splicing or alternative protein processing events).

Non-protein analogs have a chemical structure designed to mimic the functional activity of a protein of the invention. Such analogs are administered according to methods of the presently disclosed subject matter. Such analogs may exceed the physiological activity of the original polypeptide. Methods of analog design are well known in the art, and synthesis of analogs can be carried out according to such methods by modifying the chemical structures such that the resultant analogs increase the anti-neoplastic activity of the original polypeptide when expressed in an immunoresponsive cell. These chemical modifications include, but are not limited to, substituting alternative R groups and varying the degree of saturation at specific carbon atoms of a reference polypeptide. The protein analogs can be relatively resistant to in vivo degradation, resulting in a more prolonged therapeutic effect upon administration. Assays for measuring functional activity include, but are not limited to, those described in the Examples below.

In accordance with the presently disclosed subject matter, the polynucleotides encoding an extracellular domain that specifically binds to a mutant PIK3CA peptide (e.g., a human mutant PIK3CA peptide) can be modified by codon optimization. Codon optimization can alter both naturally occurring and recombinant gene sequences to achieve the highest possible levels of productivity in any given expression system. Factors that are involved in different stages of protein expression include codon adaptability, mRNA structure, and various cis-elements in transcription and translation. Any suitable codon optimization methods or technologies that are known to ones skilled in the art can be used to modify the polynucleotides of the presently disclosed subject matter, including, but not limited to, OptimumGene™, Encor optimization, and Blue Heron.

X. Administration

The presently disclosed PIK3CA-targeted TCRs and immunoresponsive cells comprising thereof can be provided systemically or directly to a subject for treating or preventing a neoplasm. In certain embodiments, mutant PIK3CA-targeted TCRs and immunoresponsive cells comprising thereof are directly injected into an organ of interest (e.g., an organ affected by a neoplasm). Alternatively or additionally, the mutant PIK3CA-targeted TCRs and immunoresponsive cells comprising thereof are provided indirectly to the organ of interest, for example, by administration into the circulatory system (e.g., the tumor vasculature). Expansion and differentiation agents can be provided prior to, during or after administration of cells and compositions to increase production of T cells in vitro or in vivo.

Mutant PIK3CA-targeted TCRs and immunoresponsive cells comprising thereof of the presently disclosed subject matter can be administered in any physiologically acceptable vehicle, normally intravascularly, although they may also be introduced into bone or other convenient site where the cells may find an appropriate site for regeneration and differentiation (e.g., thymus). In certain embodiments, at least about $1 \times 10^5$ cells can be administered, eventually reaching about $1 \times 10^{10}$ or more. In certain embodiments, at least about $1 \times 10^6$ cells can be administered. A cell population comprising immunoresponsive cells comprising an mutant PIK3CA-targeted TCR can comprise a purified population of cells. Those skilled in the art can readily determine the percentage of immunoresponsive cells in a cell population using various well-known methods, such as fluorescence activated cell sorting (FACS). The ranges of purity in cell populations comprising genetically modified immunoresponsive cells comprising a mutant PIK3CA peptide-specific TCR can be from about 50% to about 55%, from about 55% to about 60%, from about 65% to about 70%, from about 70% to about 75%, from about 75% to about 80%, from about 80% to about 85%; from about 85% to about 90%, from about 90% to about 95%, or from about 95 to about 100%. Dosages can be readily adjusted by those skilled in the art (e.g., a decrease in purity may require an increase in dosage). The immunoresponsive cells can be introduced by injection, catheter, or the like. If desired, factors can also be included, including, but not limited to, interleukins, e.g. IL-2, IL-3, IL 6, IL-11, IL-7, IL-12, IL-15, IL-21, as well as the other interleukins, the colony stimulating factors, such as G-, M- and GM-CSF, interferons, e.g., y-interferon.

In certain embodiments, compositions of the presently disclosed subject matter comprise pharmaceutical compositions comprising immunoresponsive cells comprising a mutant PIK3CA-targeted TCR and a pharmaceutically acceptable carrier. Administration can be autologous or non-autologous. For example, immunoresponsive cells comprising a mutant PIK3CA-targeted TCR and compositions comprising thereof can be obtained from one subject, and administered to the same subject or a different, compatible subject. Peripheral blood derived T cells of the presently disclosed subject matter or their progeny (e.g., in vivo, ex vivo or in vitro derived) can be administered via localized injection, including catheter administration, systemic injection, localized injection, intravenous injection, or parenteral administration. When administering a pharmaceutical composition of the presently disclosed subject matter (e.g., a pharmaceutical composition comprising immunoresponsive cells comprising a mutant PIK3CA-targeted TCR), it can be formulated in a unit dosage injectable form (solution, suspension, emulsion).

In certain embodiments, compositions of the presently disclosed subject matter can further comprise a pharmaceutically acceptable carrier.

XI. Formulations

Immunoresponsive cells comprising a presently disclosed mutant PIK3CA-targeted TCR and compositions comprising thereof of the presently disclosed subject matter can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the compositions of the presently disclosed subject matter, e.g., a composition comprising immunoresponsive cells comprising a presently disclosed mutant PIK3CA-targeted TCR, in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, alum inurn monostearate and gelatin. According to the presently disclosed subject matter, however, any vehicle, diluent, or additive used would have to be compatible with the immunoresponsive cells comprising a generally mutant PIK3CA-targeted TCR of the presently disclosed subject matter.

The compositions can be isotonic, i.e., they can have the same osmotic pressure as blood and lacrimal fluid. The desired isotonicity of the compositions of the presently disclosed subject matter may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose can be used because it is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Those skilled in the art will recognize that the components of the compositions should be selected to be chemically inert and will not affect the viability or efficacy of the immunoresponsive cells as describe in the presently disclosed subject matter. This will present no problem to those skilled in chemical and pharmaceutical principles, or problems can be readily avoided by reference to standard texts or by simple experiments (not involving undue experimentation), from this disclosure and the documents cited herein.

One consideration concerning the therapeutic use of the immunoresponsive cells of the presently disclosed subject matter is the quantity of cells necessary to achieve an optimal effect. The quantity of cells to be administered will vary for the subject being treated. In certain embodiments, from about $10^4$ to about $10^{10}$, from about $10^5$ to about $10^9$, or from about $10^6$ to about $10^8$ immunoresponsive cells of the presently disclosed subject matter are administered to a subject. More effective cells may be administered in even smaller numbers. In some embodiments, at least about $1\times10^8$, about $2\times10^8$, about $3\times10^8$, about $4\times10^8$, and about $5\times10^8$ immunoresponsive cells of the presently disclosed subject matter are administered to a human subject. The precise determination of what would be considered an effective dose may be based on factors individual to each subject, including their size, age, sex, weight, and condition of the particular subject. Dosages can be readily ascertained by those skilled in the art from this disclosure and the knowledge in the art.

The skilled artisan can readily determine the amount of cells and optional additives, vehicles, and/or carrier in compositions and to be administered in methods of the presently disclosed subject matter. Typically, any additives (in addition to the active cell(s) and/or agent(s)) are present in an amount of from about 0.001% to about 50% by weight) solution in phosphate buffered saline, and the active ingredient is present in the order of micrograms to milligrams, such as from about 0.0001 wt % to about 5 wt %, from about 0.0001 wt % to about 1 wt %, from about 0.0001 wt % to about 0.05 wt %, from about 0.001 wt % to about 20 wt %, from about 0.01 wt % to about 10 wt %, or from about 0.05 wt % to about 5 wt %. For any composition to be administered to an animal or human, and for any particular method of administration, toxicity should be determined, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, XII. Methods of Treatment Provided herein are methods for treating a malignancy in a subject. The methods comprise administering the presently disclosed cells in an amount effective to achieve the desired effect, be it palliation of an existing condition or prevention of recurrence. For treatment, the amount administered is an amount effective in producing the desired effect. An effective amount can be provided in one or a series of administrations. An effective amount can be provided in a bolus or by continuous perfusion.

For adoptive immunotherapy using antigen-specific T cells, cell doses in the range of about $10^6$ to about $10^{10}$ (e.g., about $10^9$ or about $10^6$) are typically infused. Upon administration of the immunoresponsive cells into the subject and subsequent differentiation, the immunoresponsive cells are induced that are specifically directed against one specific antigen (e.g., mutant PIK3CA peptides). "Induction" of T cells can include inactivation of antigen-specific T cells such as by deletion or anergy. Inactivation is particularly useful to establish or reestablish tolerance such as in autoimmune disorders. The immunoresponsive cells of the presently disclosed subject matter can be administered by any methods known in the art, including, but not limited to, pleural administration, intravenous administration, subcutaneous administration, intranodal administration, intratumoral administration, intrathecal administration, intrapleural administration, intraperitoneal administration, and direct administration to the thymus. In certain embodiments, the immunoresponsive cells and the compositions comprising thereof are intravenously administered to the subject in need.

The presently disclosed subject matter provides various methods of using the immunoresponsive cells (e.g., T cells) comprising a mutant PIK3CA-targeted TCR. For example, the presently disclosed subject matter provides methods of reducing tumor burden in a subject. In certain non-limiting examples, the method of reducing tumor burden comprises administering an effective amount of the presently disclosed immunoresponsive cell to the subject, thereby inducing tumor cell death in the subject. The presently disclosed immunoresponsive cell can reduce the number of tumor cells, reduce tumor size, and/or eradicate the tumor in the subject.

The presently disclosed subject matter also provides methods of increasing or lengthening survival of a subject having a neoplasm. In certain non-limiting example, the method of increasing or lengthening survival of a subject having a neoplasm comprises administering an effective amount of the presently disclosed immunoresponsive cell to the subject, thereby increasing or lengthening survival of the subject.

Cancers whose growth may be inhibited using the immunoresponsive cells of the presently disclosed subject matter comprise cancers typically responsive to immunotherapy. Non-limiting examples of cancers for treatment include any PIK3CA mutated cancers, including and are not limited to, breast cancer, endometrial cancer, cervical cancer, anal cancer, bladder cancer, colorectal cancer, head and neck squamous cell carcinoma, nonmelanoma skin cancer and salivary gland cancer. In certain embodiments, the cancer is breast cancer.

Additionally, the presently disclosed subject matter provides methods of increasing immune-activating cytokine production in response to a cancer cell in a subject. In certain embodiments, the method comprises administering the presently disclosed immunoresponsive cell to the subject. The immune-activating cytokine can be granulocyte macrophage colony stimulating factor (GM-CSF), IFN-α, IFN-β, IFN-γ, TNF-α, IL-2, IL-3, IL-6, IL-11, IL-7, IL-12, IL-15, IL-21, interferon regulatory factor 7 (IRF7), and combinations thereof. In certain embodiments, the immunoresponsive cells including a mutant PIK3CA peptide-specific TCR of the presently disclosed subject matter increase the production of GM-CSF, IFN-γ, and/or TNF-α.

Suitable human subjects for therapy typically comprise two treatment groups that can be distinguished by clinical criteria. Subjects with "advanced disease" or "high tumor burden" are those who bear a clinically measurable tumor (e.g., breast cancer). A clinically measurable tumor is one that can be detected on the basis of tumor mass (e.g., by palpation, CAT scan, sonogram, mammogram or X-ray; positive biochemical or histopathologic markers on their own are insufficient to identify this population). A pharmaceutical composition embodied in the presently disclosed subject matter is administered to these subjects to elicit an anti-tumor response, with the objective of palliating their condition. Ideally, reduction in tumor mass occurs as a result, but any clinical improvement constitutes a benefit. Clinical improvement comprises decreased risk or rate of progression or reduction in pathological consequences of the tumor (e.g., breast cancer).

A second group of suitable subjects is known in the art as the "adjuvant group." These are individuals who have had a history of neoplasm (e.g., breast cancer), but have been responsive to another mode of therapy. The prior therapy can have included, but is not restricted to, surgical resection, radiotherapy, and traditional chemotherapy. As a result, these individuals have no clinically measurable tumor. However, they are suspected of being at risk for progression of the disease, either near the original tumor site, or by metastases. This group can be further subdivided into high-risk and low-risk individuals. The subdivision is made on the basis of features observed before or after the initial treatment. These features are known in the clinical arts, and are suitably defined for each different neoplasm. Features typical of high-risk subgroups are those in which the tumor (e.g., breast cancer) has invaded neighboring tissues, or who show involvement of lymph nodes. Another group has a genetic predisposition to neoplasm (e.g., breast cancer) but has not yet evidenced clinical signs of neoplasm (e.g., breast cancer). For instance, women testing positive for a genetic mutation associated with breast cancer, but still of child-bearing age, can wish to receive one or more of the TCRs described herein in treatment prophylactically to prevent the occurrence of neoplasm until it is suitable to perform preventive surgery.

The subjects can have an advanced form of disease (e.g., breast cancer), in which case the treatment objective can include mitigation or reversal of disease progression, and/or amelioration of side effects. The subjects can have a history of the condition, for which they have already been treated, in which case the therapeutic objective will typically include a decrease or delay in the risk of recurrence.

XIII. Kits

The presently disclosed subject matter provides kits for the treatment or prevention of a malignancy (e.g., breast cancer). In certain embodiments, the kit comprises a therapeutic or prophylactic composition containing an effective amount of an immunoresponsive cell comprising a mutant PIK3CA-targeted TCR in unit dosage form. In particular embodiments, the cells further expresses at least one co-stimulatory ligand.

If desired, the immunoresponsive cell can be provided together with instructions for administering the cell to a subject having or at risk of developing a malignancy (e.g., breast cancer). The instructions will generally include information about the use of the composition for the treatment or prevention of a malignancy (e.g., breast cancer). In other embodiments, the instructions include at least one of the following: description of the therapeutic agent; dosage schedule and administration for treatment or prevention of a malignancy (e.g., breast cancer) or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

EXAMPLES

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the compositions, and assay, screening, and therapeutic methods of the invention, and are not intended to limit the scope of what the inventors regard as their invention.

Example 1: Generation of Mutant PIK3CA-Targeted TCRs

Figure 3:
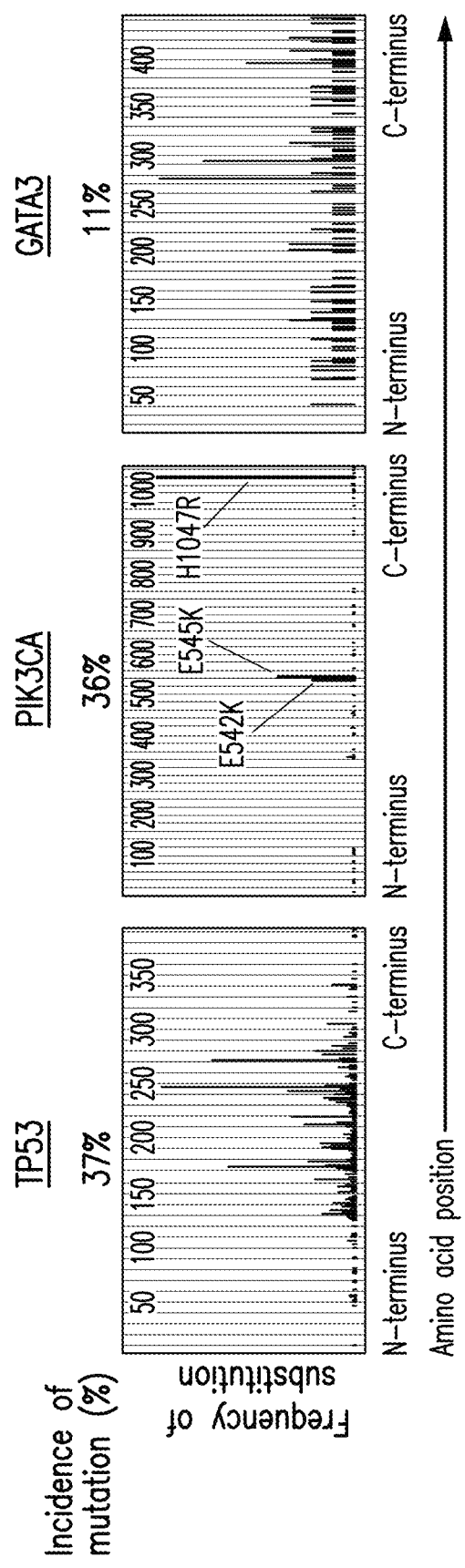
FIG. 3 depicts that PIK3CA had only a limited number of hotspot mutations conserved across patients in breast cancer.

Previous study demonstrated that a third of breast cancers have PIK3CA mutations. Millis et al., *JAMA Oncol.* 2016; 2 (12): 1565-1573. The mutations were more common in HR+ breast cancer (40-80%) and were sufficient to drive breast cancer in cells and animals. FIG. 1 shows the frequency and location of PIK3CA mutations in 1,501 MSKCC HR+/HER2− breast cancer patients, where H1047L/R mutation accounted of 35% of the cases. As shown in FIG. 2, the location of hotspot mutations in PIK3CA were similar across breast cancer subtypes. As shown in FIG. 3, PIK3CA has only a limited number of hotspot mutations conserved across patients in breast cancer. These features made targeting specific mutations of PIK3CA a promising strategy for targeting and eliminating breast cancer cells.

Figure 4:
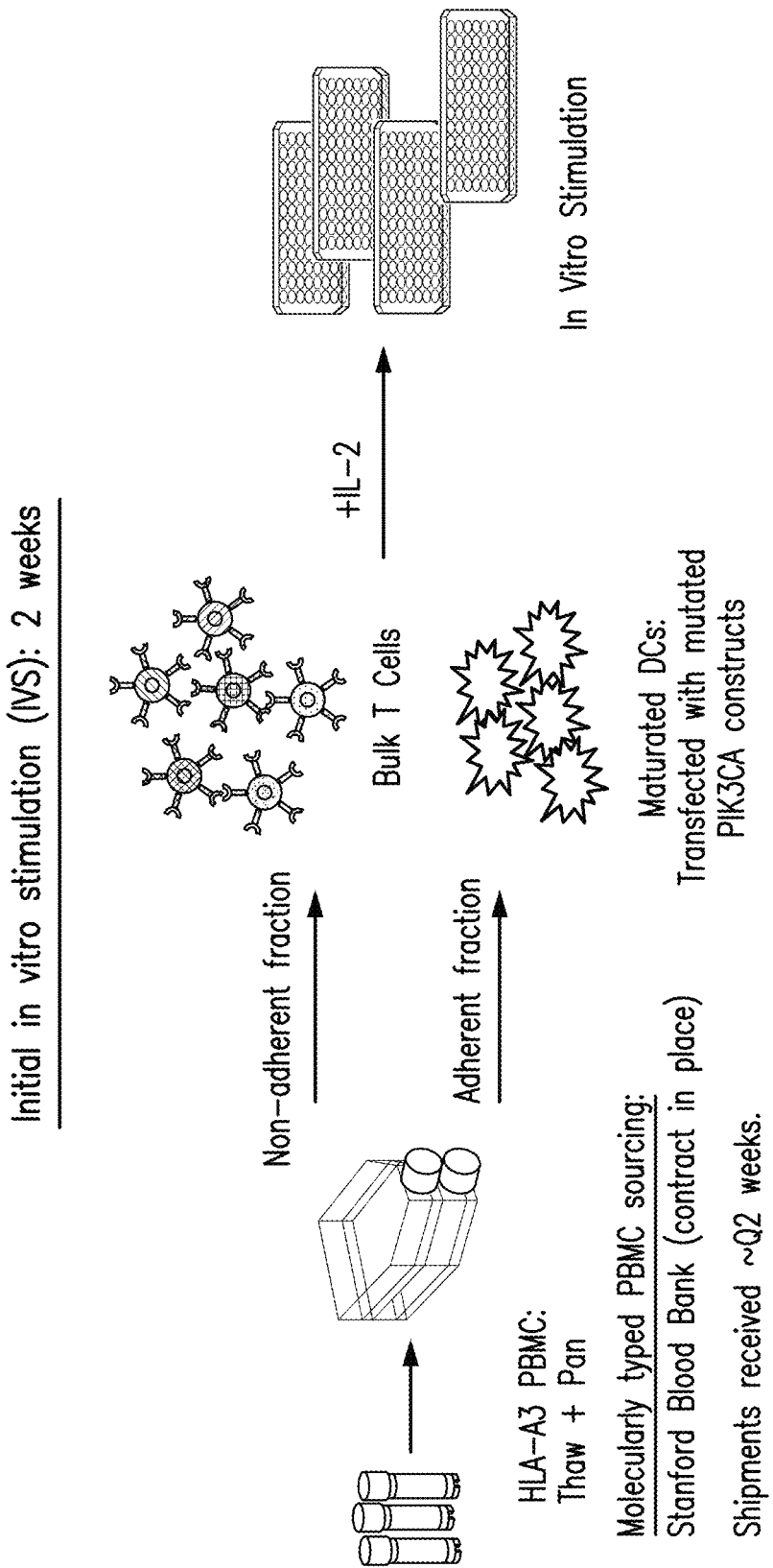
FIG. 4 depicts in vitro sensitization (IVS) of donor-derived cells. PBMCs from healthy donors stimulated with autologous mature antigen-presenting cells were transfected with mRNA encoding a 65 amino acid segment of the PIK3CA gene flanking common hotspot mutations. Cells received in vitro antigen stimulation two/three times over a period of two/three weeks in the presence of low-dose IL-2 (90 IU/mL).
Figure 5:
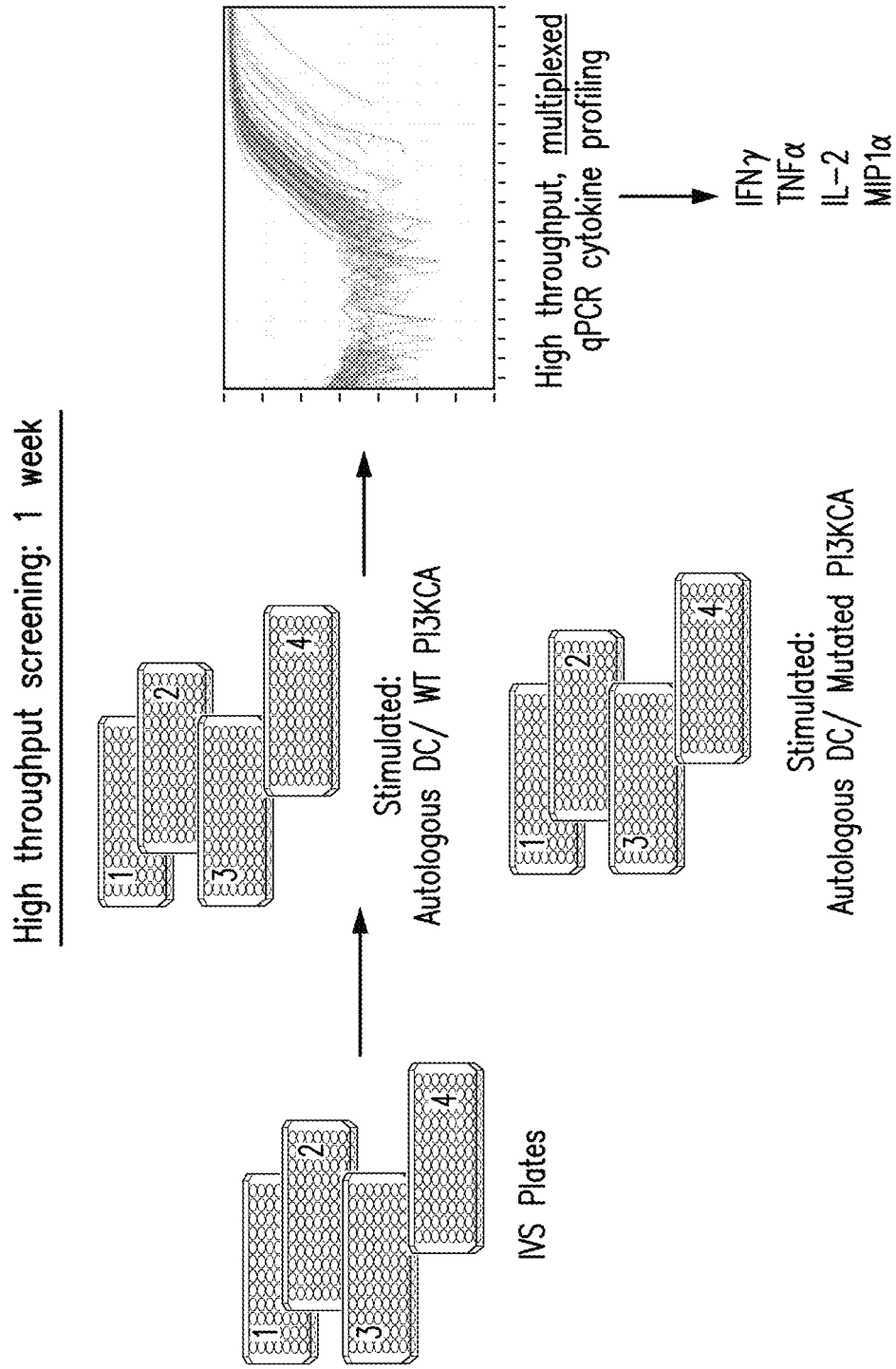
FIG. 5 depicts high throughput reactivity screen. Individual in vitro sensitized microwells were tested for mutation-specific reactivity by incubating with autologous APCs transfected with mRNA encoding either the wild-type (WT) or mutated PIK3CA. Mutation-specific recognition was determined by the preferential upregulation of mRNA transcript of acute inflammatory markers such as IFN-g and TNF-a by high throughput quantitative PCR.
Figure 6:
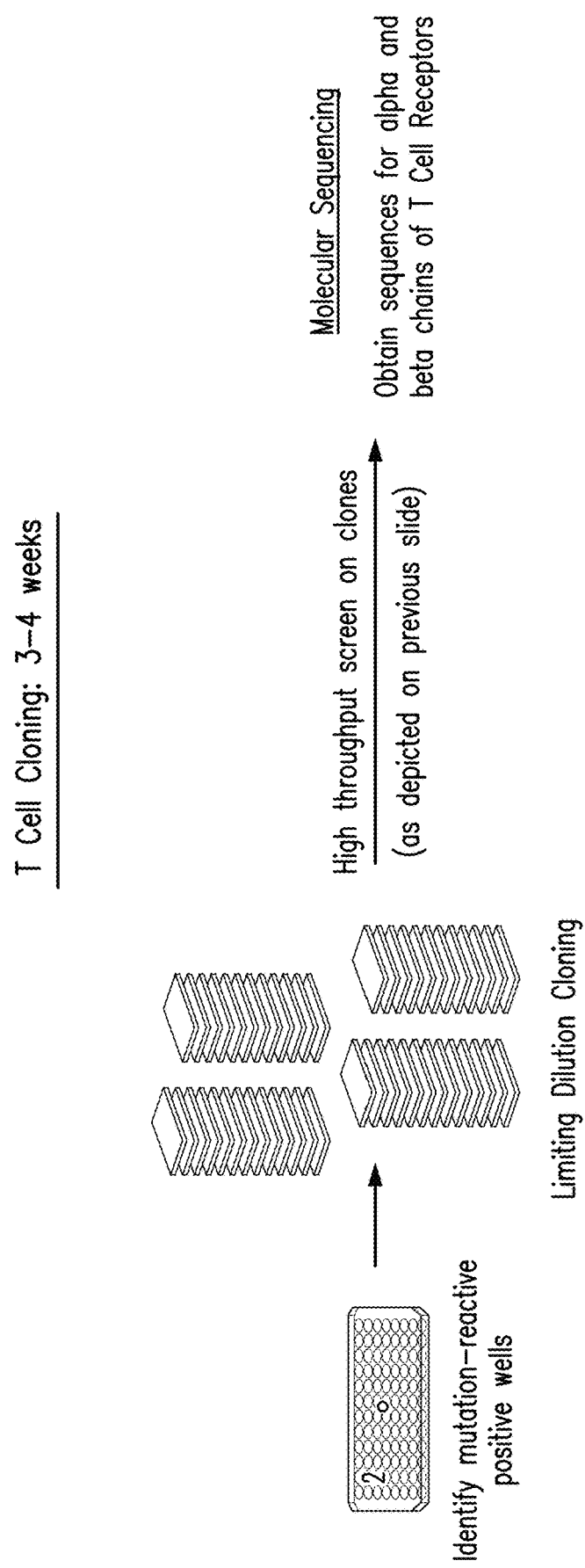
FIG. 6 depicts isolation of mutation-specific T cells. Positive microwells underwent limiting dilution cloning to derive T cell clones of a single specificity. Individual clones were screened for mutation-specific recognition using previously described methodology; molecular sequencing was performed on positive clones to derive the alpha and beta chain sequences of its T cell receptor.
Figure 7:
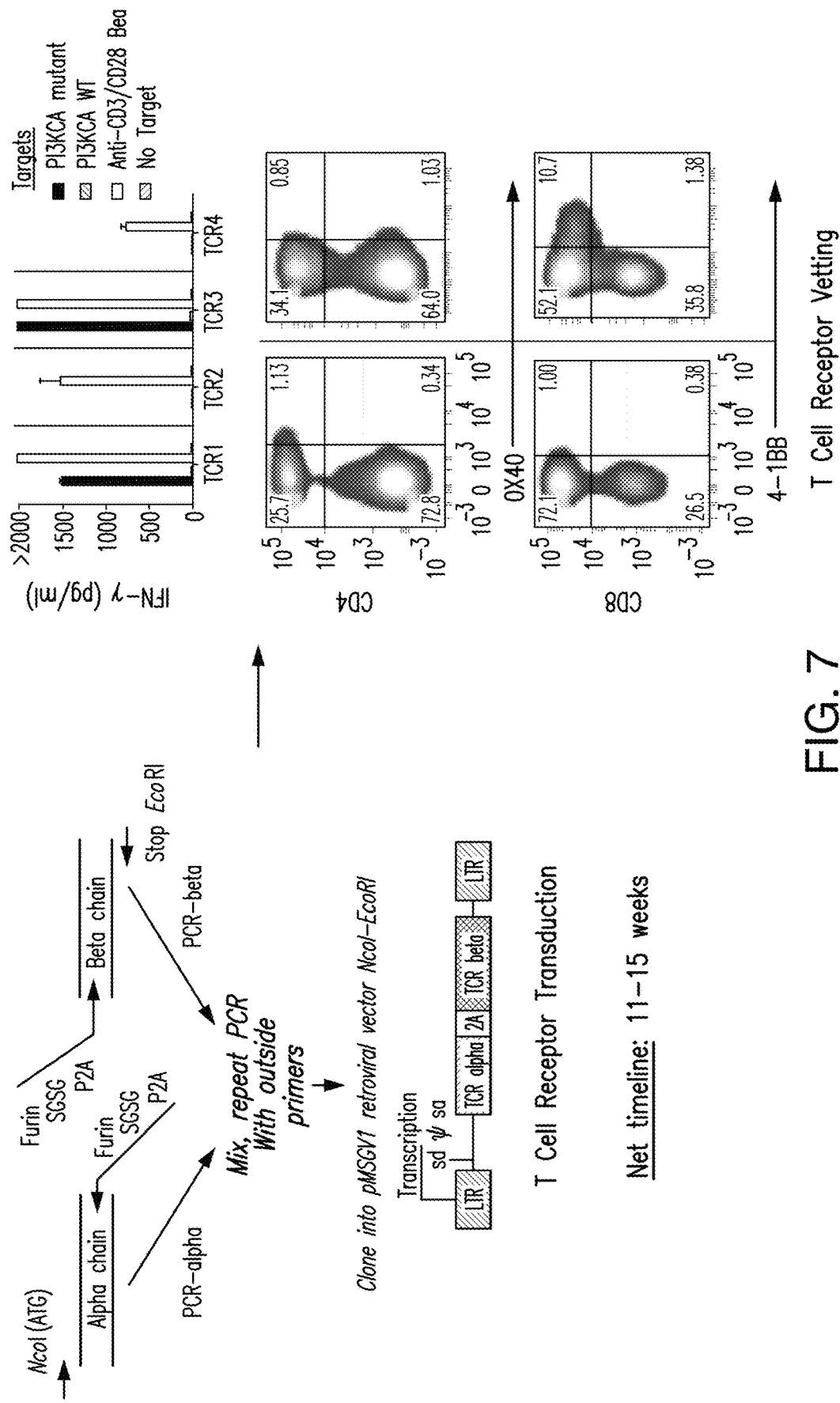
FIG. 7 depicts a demonstrative illustration of TCR reconstruction and conference of reactivity. The genetic sequences encoding the alpha and beta chains of the mutation-specific TCR were cloned into a retroviral vector and stably integrated into allogeneic PBMC. Conference of reactivity to mutation-specific transfectants and HLA-matched tumor cell line targets expressing the mutant antigen were determined by IFN-g secretion and upregulation of costimulatory molecules such as 4-1BB and OX40. A representative schema of this process is shown as an example.

To identify TCRs specifically targeting mutant PIK3CA, peripheral blood mononuclear cells (PBMCs) from healthy donors were stimulated with autologous mature antigen-presenting cells transfected with mRNA encoding a 65-amino acid segment of the PIK3CA gene flanking common hotspot mutations. The cells received in vitro antigen stimulation two/three times over a period of two/three weeks in the presence of low-dose IL-2 (90 IU/mL) (FIG. 4). High throughput reactivity screen was then performed, where individual in vitro sensitized microwells were tested for mutation-specific reactivity by incubating with autologous APCs transfected with mRNA encoding either the wild-type (WT) or mutated PIK3CA (FIG. 5). Mutation-specific recognition is determined by the preferential upregulation of mRNA transcript of acute inflammatory markers such as IFN-g and TNF-a by high throughput quantitative PCR (FIG. 5). Mutation-specific T cells were then isolated, where positive microwells underwent limiting dilution cloning to derive T cell clones of a single specificity, and individual clones were screened for mutation-specific recognition using previously described methodology. Molecular sequencing was then performed on positive clones to derive the alpha and beta chain sequences of its T cell receptor (FIG. 6). Further, mutant PIK3CA specific TCRs were reconstruction. The genetic sequences encoding the alpha and beta chains of the mutation-specific TCR were cloned into a retroviral vector and stably integrated into allogeneic PBMC (FIG. 7). Conference of reactivity to mutation-specific transfectants and HLA-matched tumor cell line targets comprising the mutant antigen were determined by IFN-g secretion and upregulation of costimulatory molecules such as 4-1BB and OX40. A representative schema of this process is shown in FIG. 7 as an example. Stimulation and screening constructs for mPIK3CA are shown in FIG. 8.

Figure 9:
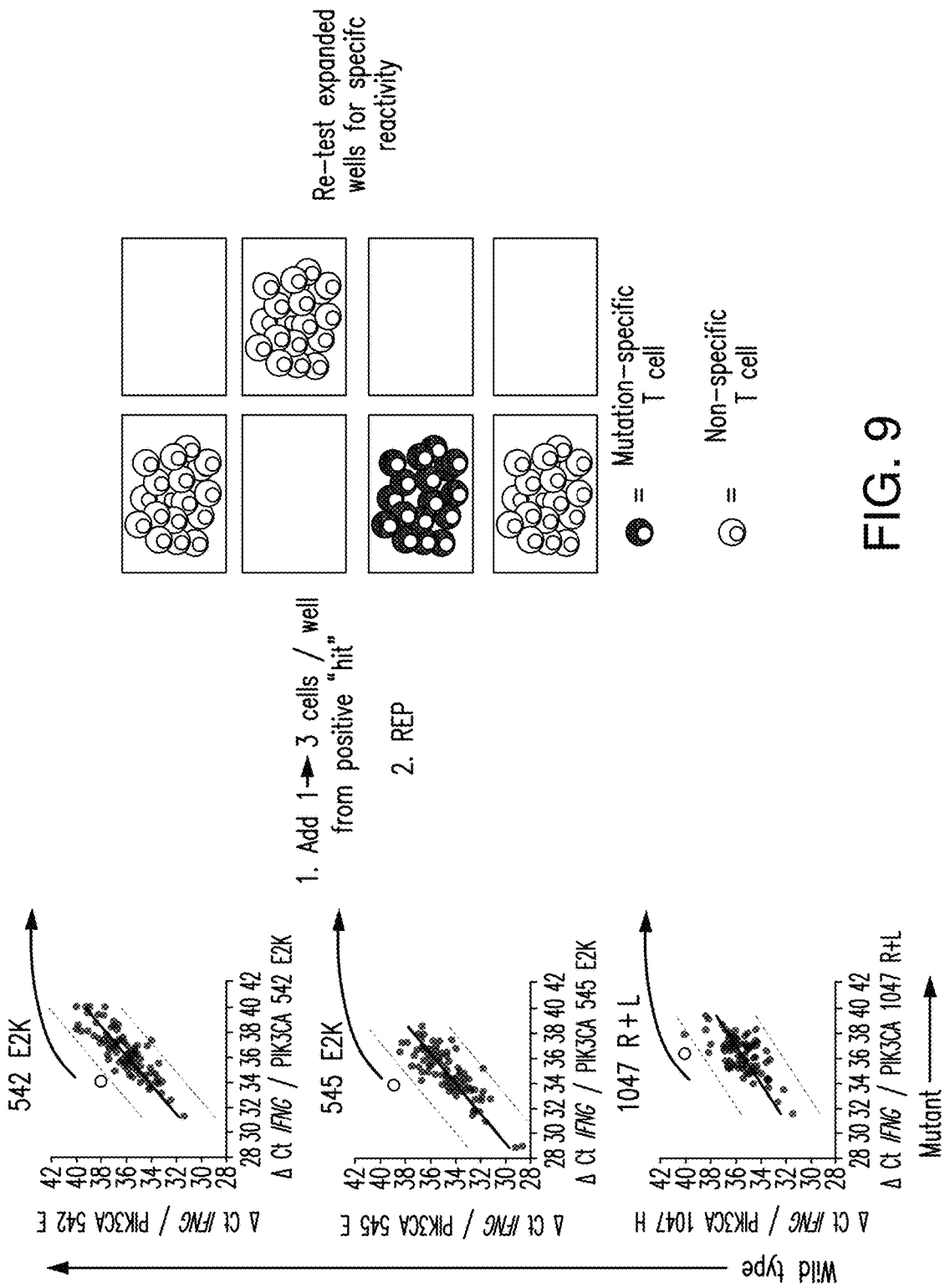
FIG. 9 depicts identification of mutation-reactive microwells following in vitro sensitization. Delta CT values from sister wells against mutated or WT PI3KCA are plotted on the X and Y axis respectively. Each dot represents an individual sensitized microwell. Mutation-specific recognition of the hotspot mutations, E542K in the top panel, E545K mutation in the middle panel and the H1047R/L in the bottom panel are shown. Dots indicated by the arrows representing wells that preferentially upregulate IFN-g transcript in response to mutated PIK3CA were selected to undergo limiting dilution cloning to derive mutation-specific T cell clones.

Mutation-reactive microwells were identified following in vitro sensitization. As shown in FIG. 9, delta CT values from sister wells against mutated or WT PI3KCA plotted on the X and Y axis respectively. Each dot represents an individual sensitized microwell. Mutation-specific recognition of the hotspot mutations, E542K in the top panel, E545K mutation in the middle panel and the H1047R/L in the bottom panel are also shown in FIG. 8, where outliner dots identified by the arrows indicating wells that preferentially upregulate IFN-g transcript in response to mutated PIK3CA were selected to undergo limiting dilution cloning to derive mutation-specific T cell clones. MHC Class I and Class II restricted tranfections controls, e.g., MART-1/A2: 01 (modified): ghsyttacelagigiltvilgvlll [SEQ ID NO: 78] and MAGE-A3 DPB04: ILGDPKKLLTQHFVQE NYLEYRQVP [SEQ ID NO: 79], were used.

Figure 10:
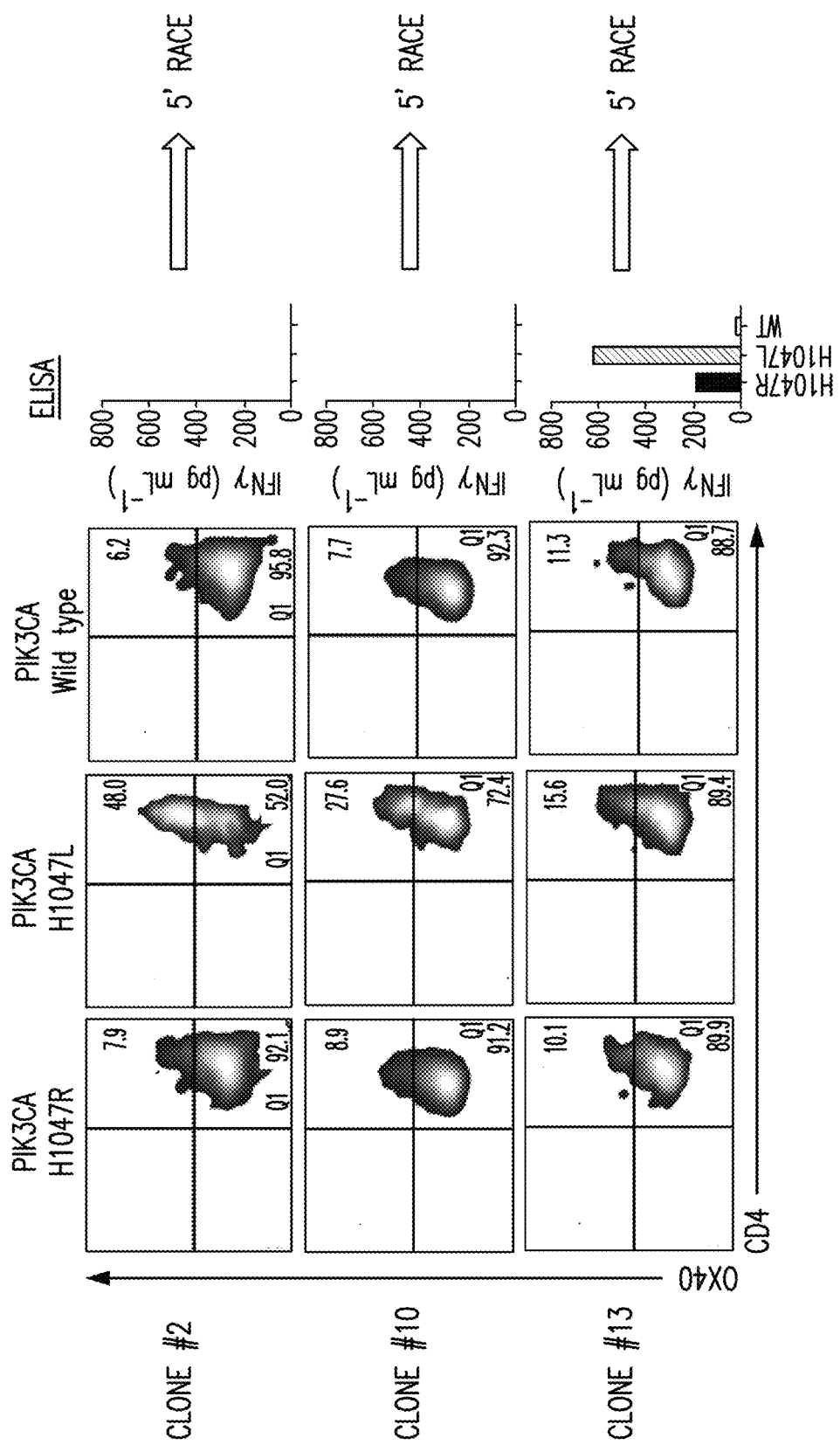
FIG. 10 depicts screening of clones derived from limiting dilution. Growth-positive wells following limiting dilution cloning were screened for PIK3CA mutation-specific recognition by measuring the preferential upregulation of the costimulatory molecule, OX40 (left panel) and/or the release of IFN-g (right panel) in response to the mutated antigen. Positive clones were selected to undergo molecular sequencing to derive the genetic code for the alpha and beta chains of their T cell receptor.

Clones derived from limiting dilution were further screened, where growth-positive wells following limiting dilution cloning were screened for PIK3CA mutation-specific recognition by measuring the preferential upregulation of the costimulatory molecule, OX40 (FIG. 10, left panel) and/or the release of IFN-g (FIG. 10, right panel) in response to the mutated antigen. Positive clones were selected to undergo molecular sequencing to derive the genetic code for the alpha and beta chains of their T cell receptor.

Figure 11:
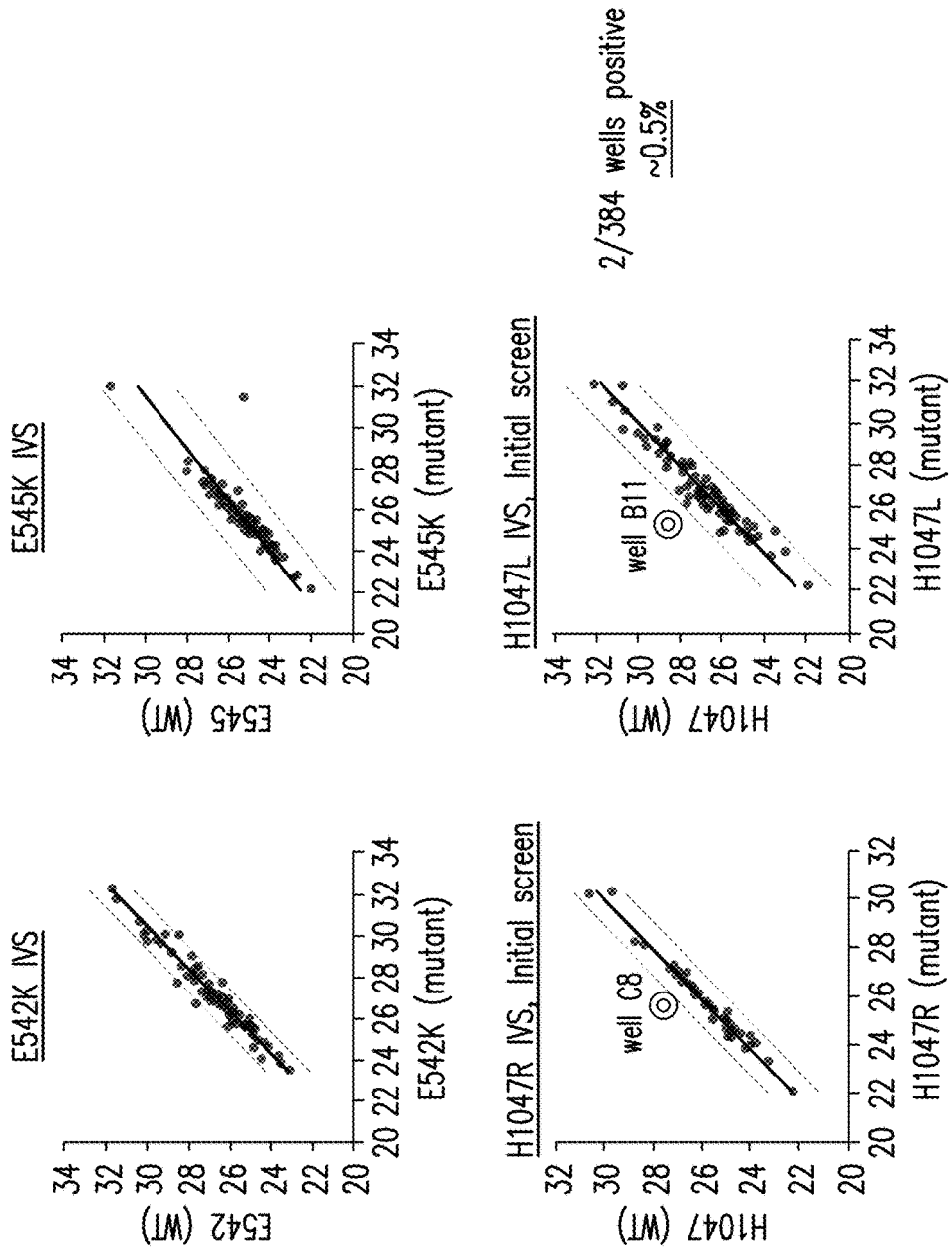
FIG. 11 depicts high throughput screen and identification of PI3KCA-mutation reactive wells of Donor 3 T cells. Delta CT values from paired microwells against mutant or WT PIK3CA are plotted on the X and Y axis, respectively. Each dot represents an individual sensitized microwell (n=384) sensitized against one of four PI3KCA hotspot mutations listed. Well C8 (bottom left) derived from a H1047R-sensitized IVS and Well B11 (bottom right) derived from a H1047L-sensitized IVS were mutation-specific, as determined by preferential upregulation of IFN-g mRNA to mutant antigen.

Similar screening was also performed with T cells derived from Donor 3 as show in FIG. 11. Delta CT values from paired microwells against mutant or WT PIK3CA were plotted on the X and Y axis respectively. Each dot represented an individual sensitized microwell (n=384) sensitized against one of four PI3KCA hotspot mutations listed. Well C8 (bottom left) derived from a H1047R-sensitized IVS and Well B11 (bottom right) derived from a H1047L-sensitized IVS were mutation-specific, as determined by preferential upregulation of IFN-g mRNA to mutant antigen.

Single-cell sequencing was incorporated into the discovery platform, the benefit of which includes, but are not limited to: a) potential to remove requirement to perform limited dilution cloning and save at least 2 weeks of time; b) ensuring maximal TCR diversity is captured by avoiding limited dilution cloning, which minimizes risk of losing TCRs associated with slow or poor growing T cells; c) increased discovery throughput by reduction in staff labor to tend to micro-wells and cloning and by making certain steps amenable to automation; and d) increased accuracy in identifying reactive TCRs (if paired with full RNA-seq, can design screens to incorporate assessment of both TCR frequency with function).

Figure 12:
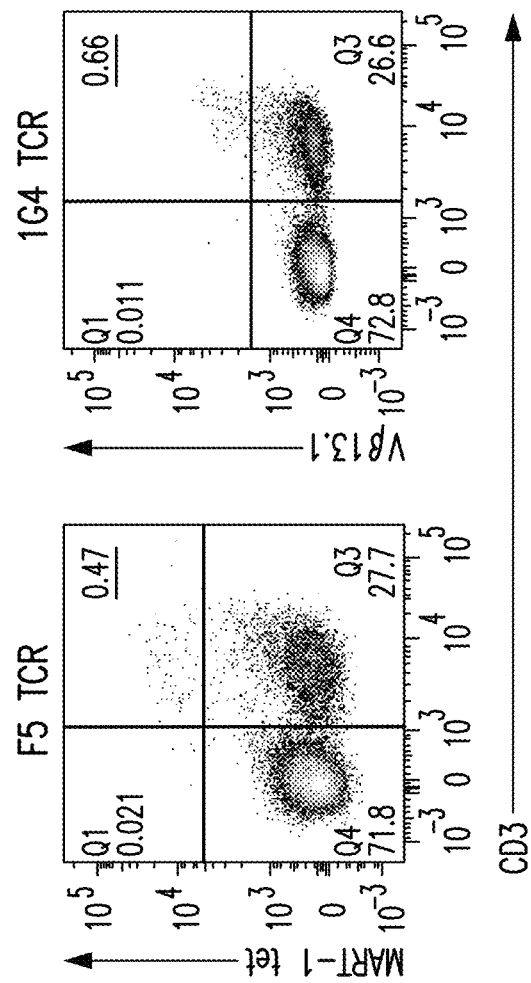
FIG. 12 depicts validation of single-cell sequencing platform to correctly retrieve and quantify paired TCRa/b gene sequences from bulk populations.

PBMCs were transduced with known TCRs (F5=MART-1, 1G4=NY-ESO-1). TCR transduced T cells were spiked at a known concentration into a bulk untransduced PBMC mixture. Single cell sequencing was used to assess whether the platform can: i) retrieve high quality and correctly paired TCR a/b sequences from the spiked samples, and ii) accurately quantify the frequency of the spiked samples (FIG. 12). FIG. 13 shows that sequencing correctly identified, paired, and quantified known TCRs within a bulk PBMC population.

FIG. 14 shows the confirmation of RC8 reactivity. Autologous APCs transfected with RNA encoding either WT or the R/L substitutions at position 1047 in the PIK3CA gene were incubated with T cells from Well C8 (referred to as RC8). Delta CT values determined by upregulation of IFN-g transcript indicated mutation-specific recognition of both R and L hotspot mutations and no WT recognition. The table in the lower panel of FIG. 14 lists the CDR3 sequences and frequencies of the top 10 clonotypes in RC8 derived by the platform.

Figure 15:
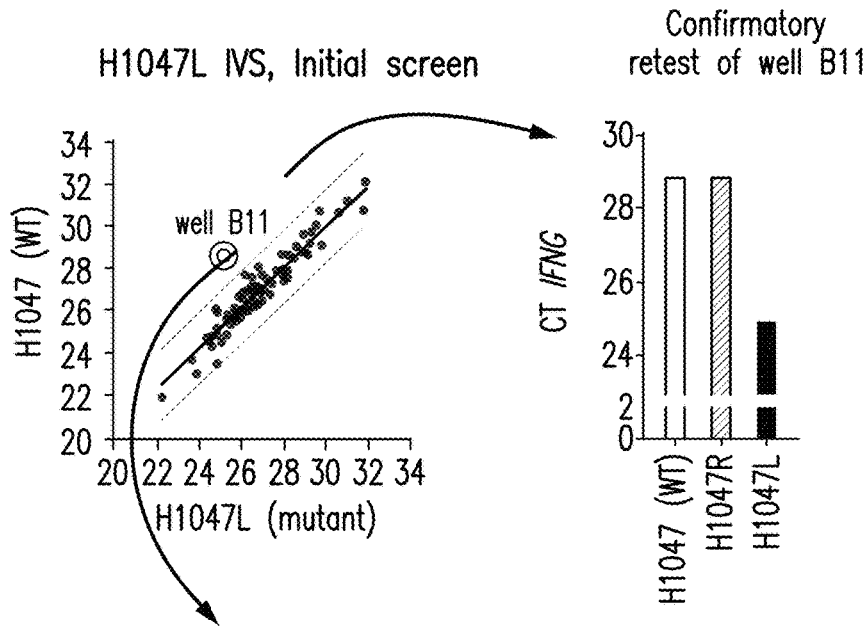
FIG. 15 depicts confirmation of LB11 reactivity: Autologous APCs transfected with RNA encoding either WT or the R/L substitutions at position 1047 in the PIK3CA gene were incubated with T cells from Well B11 (referred to as LB11). Delta CT values determined by upregulation of IFN-g transcript indicate specific recognition of H1047L alone and no H1047R or WT recognition. The table in the lower panel lists the CDR3 sequences (SEQ ID NOS 36, 46, 33, 36, 43, 46, 56, 53, 56, 43, 33, 53, 63 and 66, respectively, in order of appearance) and frequencies of the top 10 clonotypes in LB11 derived by the platform.

FIG. 15 shows the confirmation of LB11 reactivity: Autologous APCs transfected with RNA encoding either WT or the R/L substitutions at position 1047 in the PIK3CA gene were incubated with T cells from Well B11 (referred to as LB11). Delta CT values determined by upregulation of IFN-g transcript indicated specific recognition of H1047L alone and no H1047R or WT recognition. The table in the lower panel of FIG. 15 lists the CDR3 sequences and frequencies of the top 10 clonotypes in LB11 derived by the platform.

Figure 16:
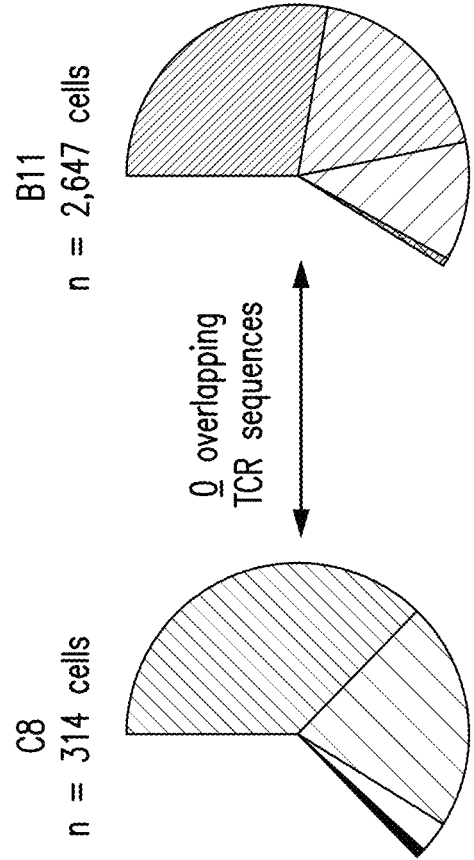
FIG. 16 depicts the pattern of PIK3CA hotspot neoantigen reactivity and TCR repertoire was entirely distinct in T cells from well C8 and B11.

TCR sequences were unique across the reactive wells. As shown in FIG. 16, pie charts represent the clonotypes detected in Well C8 (left) versus Well B11 (right) by sequencing. Wells were highly oligoclonal and all clonotypes detected were unique to the individual wells with no shared sequences.

Top clonotypes of the unique TCRs were constructed into expression vectors, where the alpha chain and the beta chain of each TCR were connected by a furin-2A peptide. Based on previously described techniques, the human constant regions of the alpha and beta chains were replaced with mouse constant regions to prevent mispairing with endogenous TCR. Sequences of these TCR constructs are shown in FIG. 17 and Tables 1-7. FIG. 18 summarizes the characteristics of the PIK3CA mutation-specific TCRs.

Figure 19:
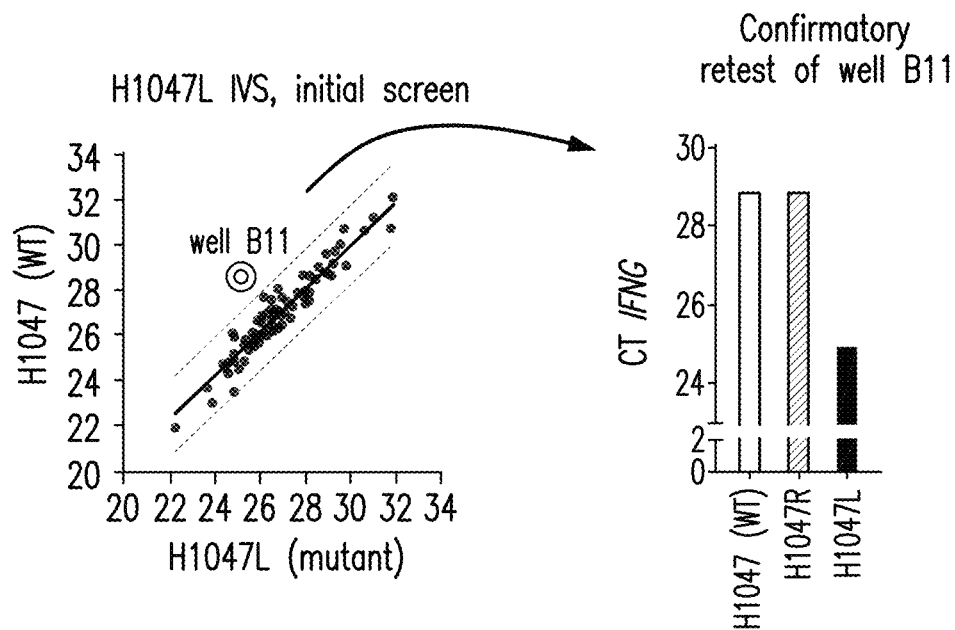
FIG. 19 depicts confirmation of LB11 reactivity. Autologous APCs transfected with RNA encoding either WT or the R/L substitutions at position 1047 in the PIK3CA gene were incubated with T cells from Well B11 (referred to as LB11). Delta CT values determined by upregulation of IFN-g transcript indicate specific recognition of H1047L alone and no H1047R or WT recognition. Table highlights the top 4 clonotypes derived from sequencing that were selected for TCR reconstruction and testing.

LB11 reactivity was confirmed as shown in FIG. 19. Autologous APCs transfected with RNA encoding either WT or the R/L substitutions at position 1047 in the PIK3CA gene were incubated with T cells from Well B11 (referred to as LB11). Delta CT values determined by upregulation of IFN-g transcript indicate specific recognition of H1047L alone and no H1047R or WT recognition. The top 4 clonotypes derived from sequencing were selected for TCR reconstruction and testing.

Figure 20:
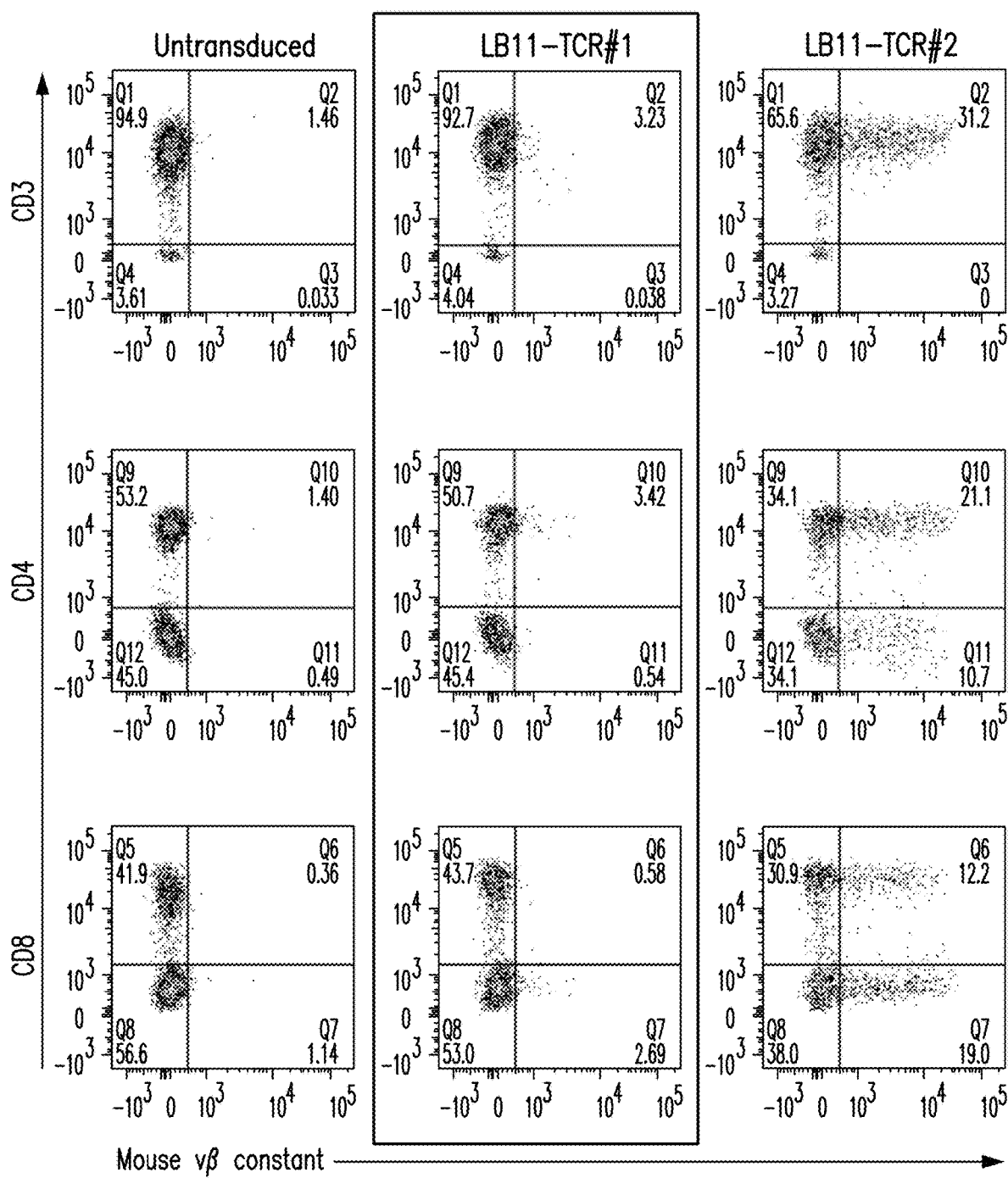
FIG. 20 depicts the efficiency of transduction of reconstructed LB11 TCRs in donor PBMCs: Allogeneic donor PBMC were transduced with retroviral particles carrying the molecular sequences for the alpha and beta chains of the LB11-derived TCR #1-4. Efficiency of transduction was determined by frequency of anti-mouse TCRβ constant staining in CD3+ (top), CD4+ (middle) and CD8+ (bottom) T cells at 4 days post-transduction.
Figure 20:
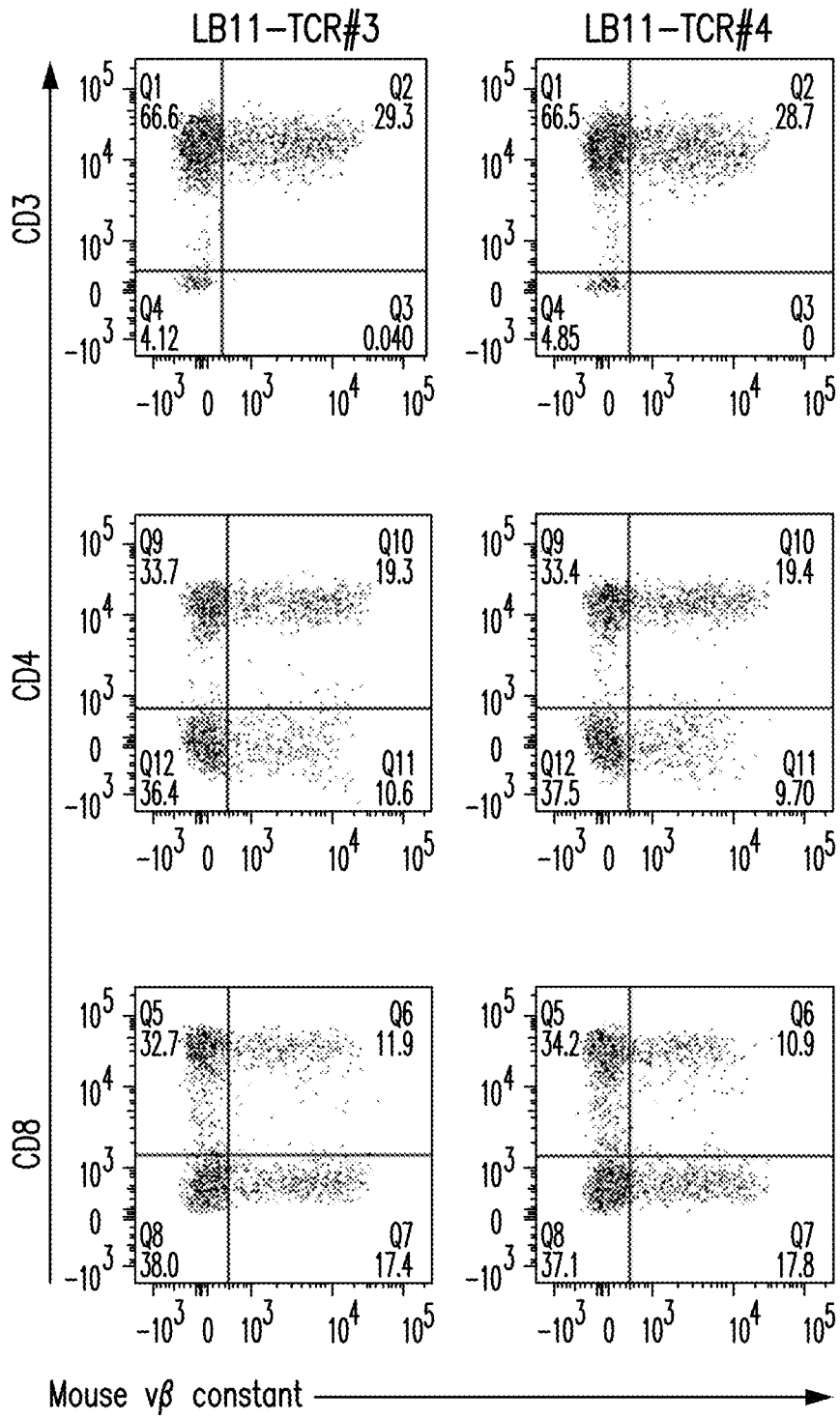

The efficiency of transduction of reconstructed LB11 TCRs in donor PBMCs is shown in FIG. 20. Allogeneic donor PBMC were transduced with retroviral particles carrying the molecular sequences for the alpha and beta chains of the LB11-derived TCR #1-4. Efficiency of transduction was determined by frequency of anti-mouse TCRβ constant staining in CD3+ (top), CD4+ (middle) and CD8+ (bottom) T cells at 4 days post-transduction.

Figure 21:
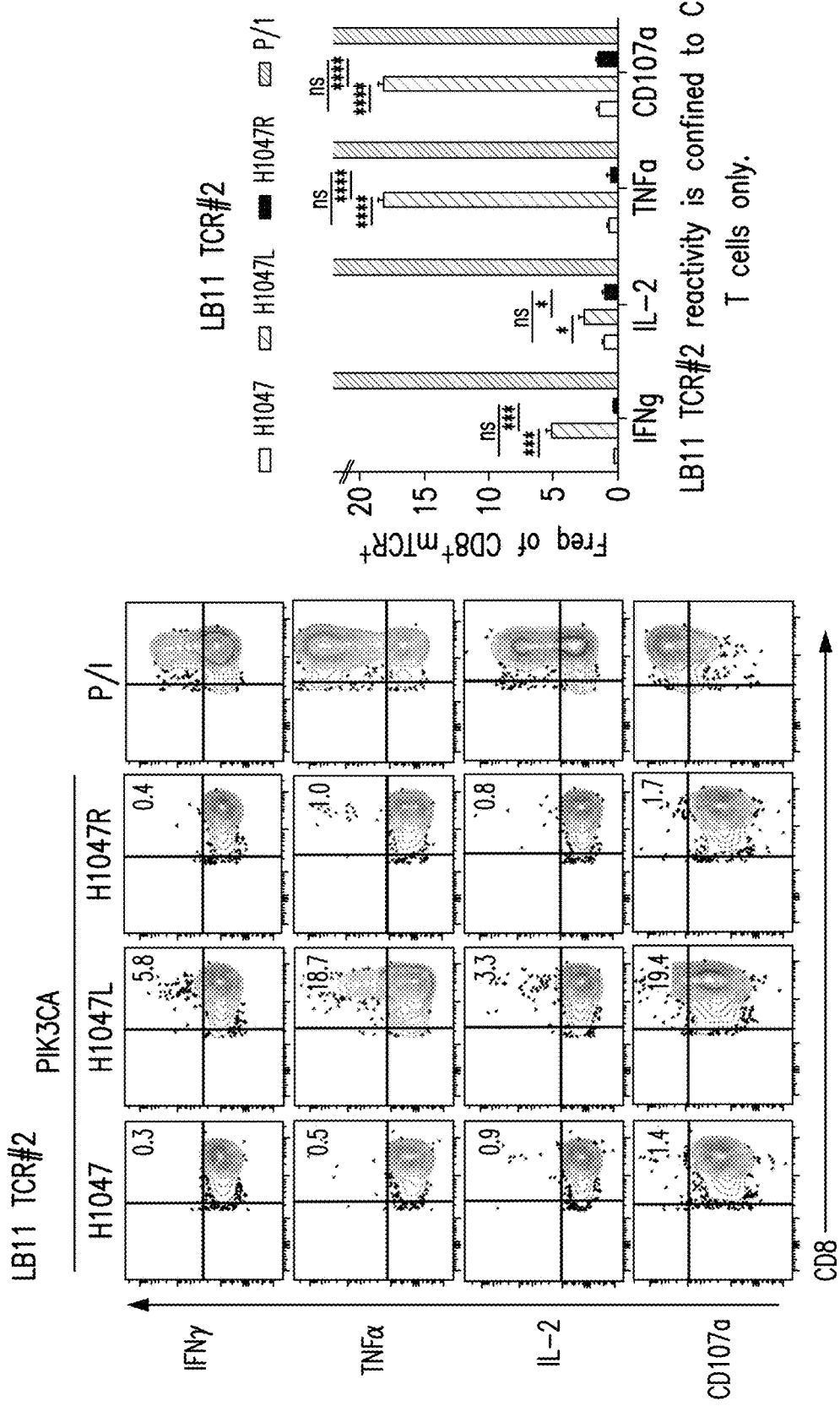
FIG. 21 depicts confirmation of the conference of mutation-specific recognition by LB11 TCR #2. Donor PBMC with stably integrated LB11 TCR #2 were cocultured with dendritic cells expressing either H1047 WT, H1047L or H1047R mutants. Dot plots (left) and bar graph summary (right) from intracellular cytokine staining of the inflammatory markers, IFNγ, TNFα, IL-2 and CD107a show mutation-specific recognition of H1047L by transduced CD8+ cells. PMA-Ionomycin bypassing TCR-mediated stimulation was included as a positive control.

The conference of mutation-specific recognition by LB11 TCR #2 was confirmed as shown in FIG. 21. Donor PBMC with stably integrated LB11 TCR #2 were cocultured with dendritic cells expressing either H1047 WT, H1047L or H1047R mutants. Dot plots (left) and bar graph summary (right) from intracellular cytokine staining of the inflammatory markers, IFNγ, TNFα, IL-2 and CD107a show mutation-specific recognition of H1047L by transduced CD8+ cells. PMA-Ionomycin bypassing TCR-mediated stimulation was included as a positive control.

Figure 22:
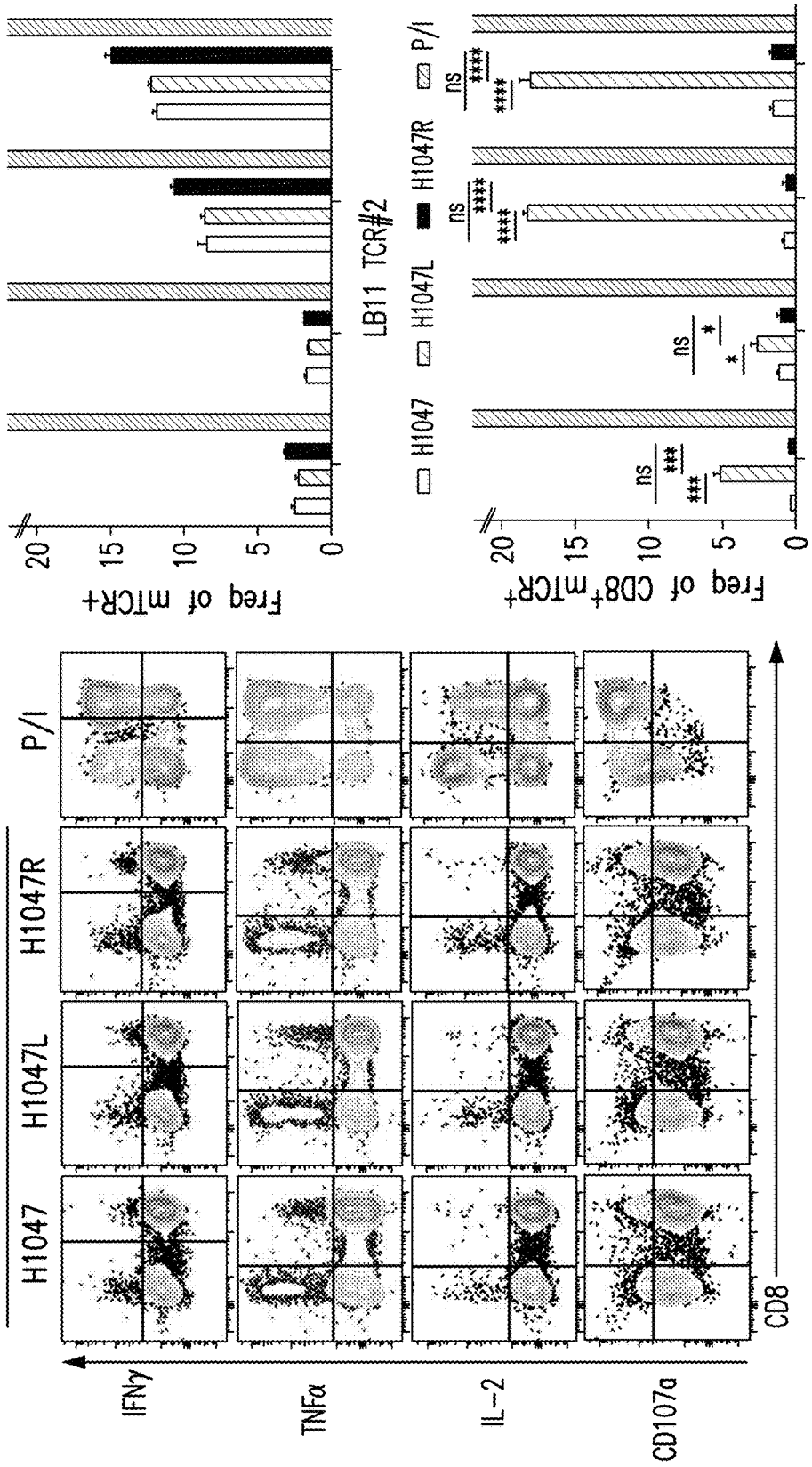
FIG. 22 depicts comparable cytokine production in a clinical grade TCR against a cancer germline antigen. Donor PBMCs were stably integrated with the cognate antigen, MAGE-A3. Dot plots (left) from intracellular cytokine staining of the inflammatory cytokines, IFNγ, TNFα, IL-2 and CD107a showed recognition of MAGE-A3 by transduced CD8+ cells. PMA-Ionomycin bypassing TCR-mediated stimulation was included as a positive control. Bar graph summary on the right comparing the cytokine-producing frequencies of mTCR+ cells in 6F9-transduced (upper) and LB11 TCR #2-transduced (lower) cells.

Comparable cytokine production in a clinical grade TCR against a cancer germline antigen was analyzed as shown in FIG. 22. Donor PBMCs were stably integrated with the cognate antigen, MAGE-A3. Dot plots (left) from intracellular cytokine staining of the inflammatory cytokines, IFNγ, TNFα, IL-2 and CD107a showed recognition of MAGE-A3 by transduced CD8+ cells. PMA-Ionomycin bypassing TCR-mediated stimulation was included as a positive control. Bar graph summary on the right comparing the cytokine-producing frequencies of mTCR+ cells in 6F9-transduced and LB11 TCR #2-transduced cells.

Figure 23:
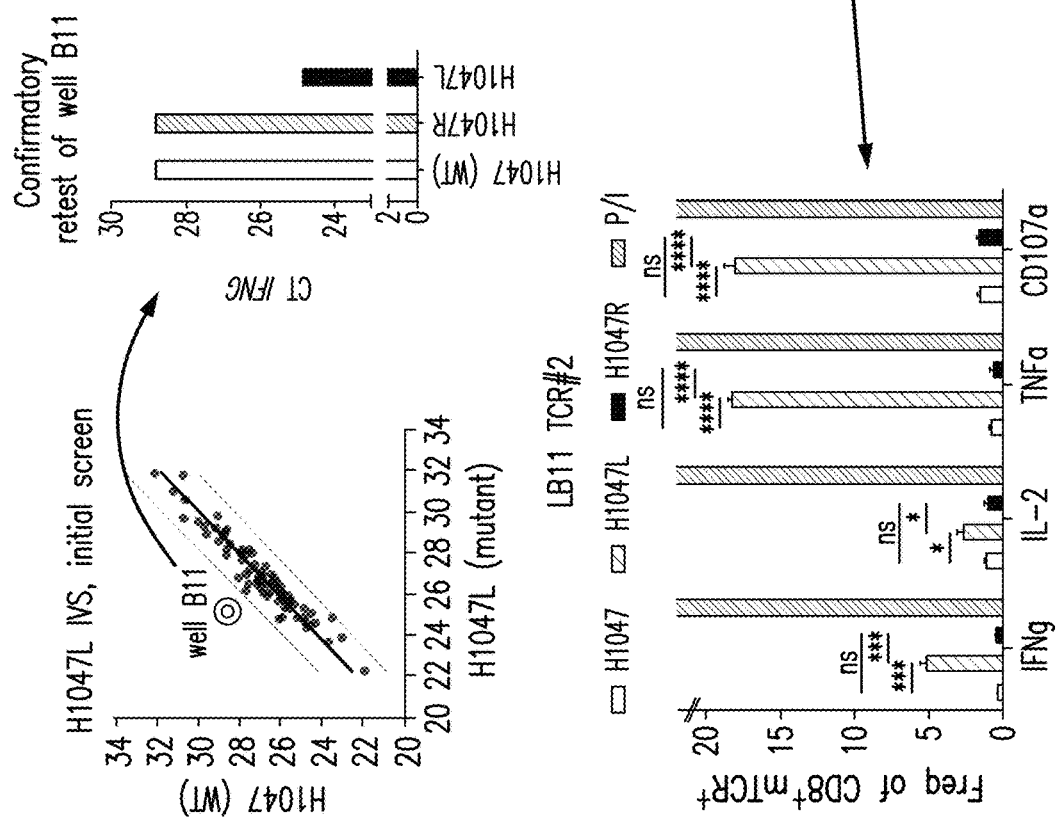
FIG. 23 depicts a closed loop from in vitro sensitization to TCR discovery. Healthy donor PBMCs sourced for mutation-specific TCRs allowed detection of a rare event (1/96). Sequencing rapidly determined the top clonotypes in the positive well. Synthetic reconstruction and testing of the TCR conclusively isolated a mutation-specific TCR, thus closing the loop from sensitization to identification to isolation of a TCR against a driver mutation.

A summary of a closed loop from in vitro sensitization to TCR discovery is shown in FIG. 23. Healthy donor PBMCs sourced for mutation-specific TCRs allowed detection of a rare event (1/96). Sequencing rapidly determined the top clonotypes in the positive well. Synthetic reconstruction and testing of the TCR conclusively isolated a mutation-specific TCR, thus closing the loop from sensitization to identification to isolation of a TCR against a driver mutation.

Example 2: Confirmation of PIK3CA-Targeted TCR, LB11-2

Figure 24:
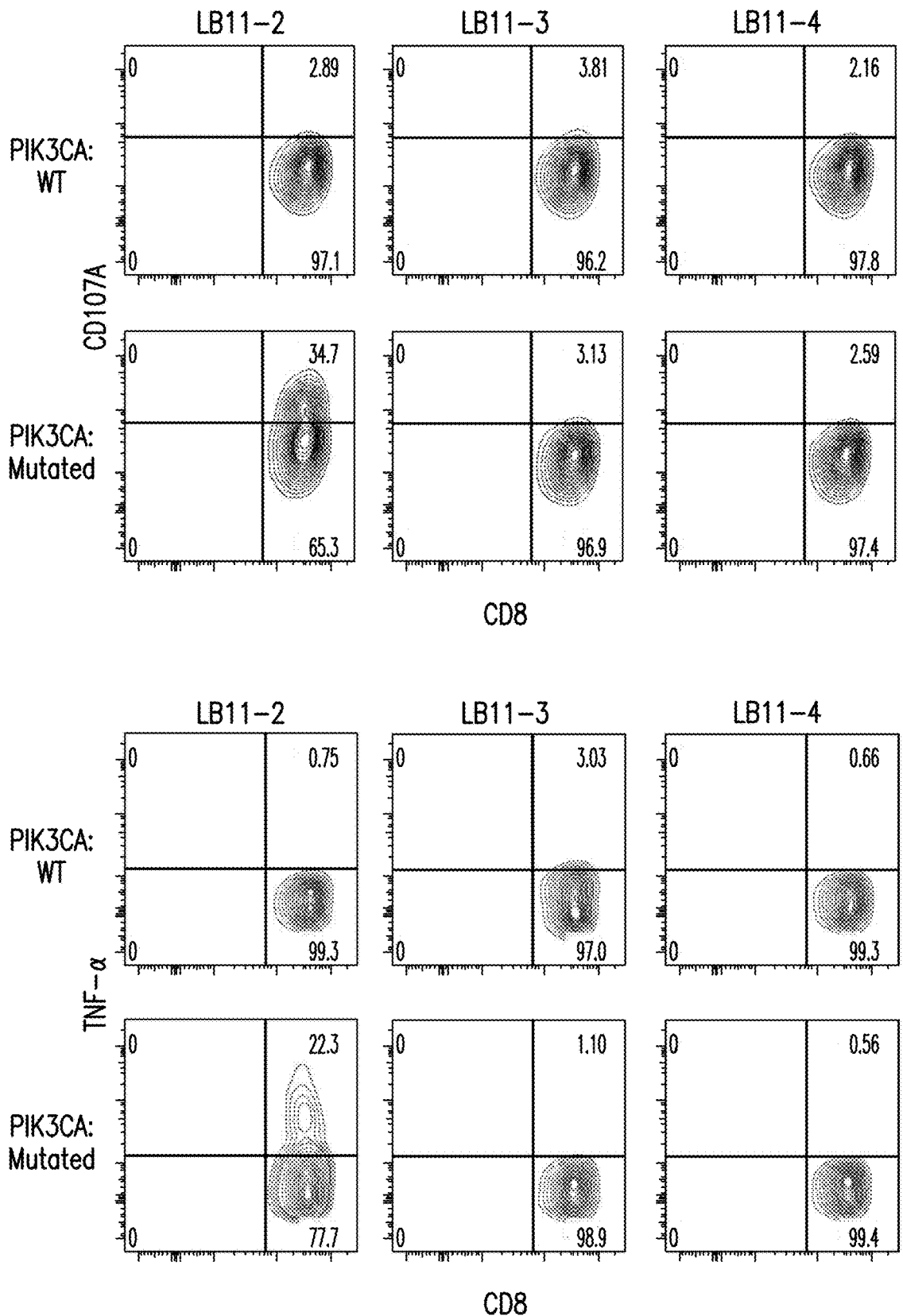
FIG. 24 depicts mutation-specific reactivity of TCRs identified via VDJ sequencing of well LB11. The genetic sequences encoding the alpha and beta chains of mutation-specific TCR derived from VDJ sequencing were cloned into a retroviral vector and stably integrated into allogeneic donor cells. The 3 unique TCR sequences derived from VDJ sequencing of well LB11 were tested. TCR-transduced cells were cocultured with autologous dendritic cells (DC) that had been transiently transfected with RNA encoding either wildtype or mutant PIK3CA. Reactivity was determined by observing the production of the degranulation marker, CD107A, (upper panels) or the inflammatory cytokine, TNF-α, (lower panels) in response to the DC expressing mutated PIK3CA.

This example further characterizes mutant PIK3CA-targeted TCR, LB11-2. As shown in FIG. 24, mutation-specific reactivity of TCRs identified via VDJ sequencing from well LB11 were further tested. The genetic sequences encoding the alpha and beta chains of mutation-specific TCR derived from VDJ sequencing were cloned into a retroviral vector and stably integrated into allogeneic donor cells. The 3 unique TCR sequences tested were LB11-2, LB11-3 and LB11-4. TCR-transduced cells were cocultured with autologous dendritic cells (DC) that had been transiently transfected with RNA encoding either wildtype or mutant PIK3CA. Reactivity was determined by observing the production of the degranulation marker, CD107A, (upper panels) or the inflammatory cytokine, TNF-α, (lower panels) in response to the DC expressing mutated PIK3CA. LB11-2 was the only mutation-specific TCR identified within this set.

Figure 25:
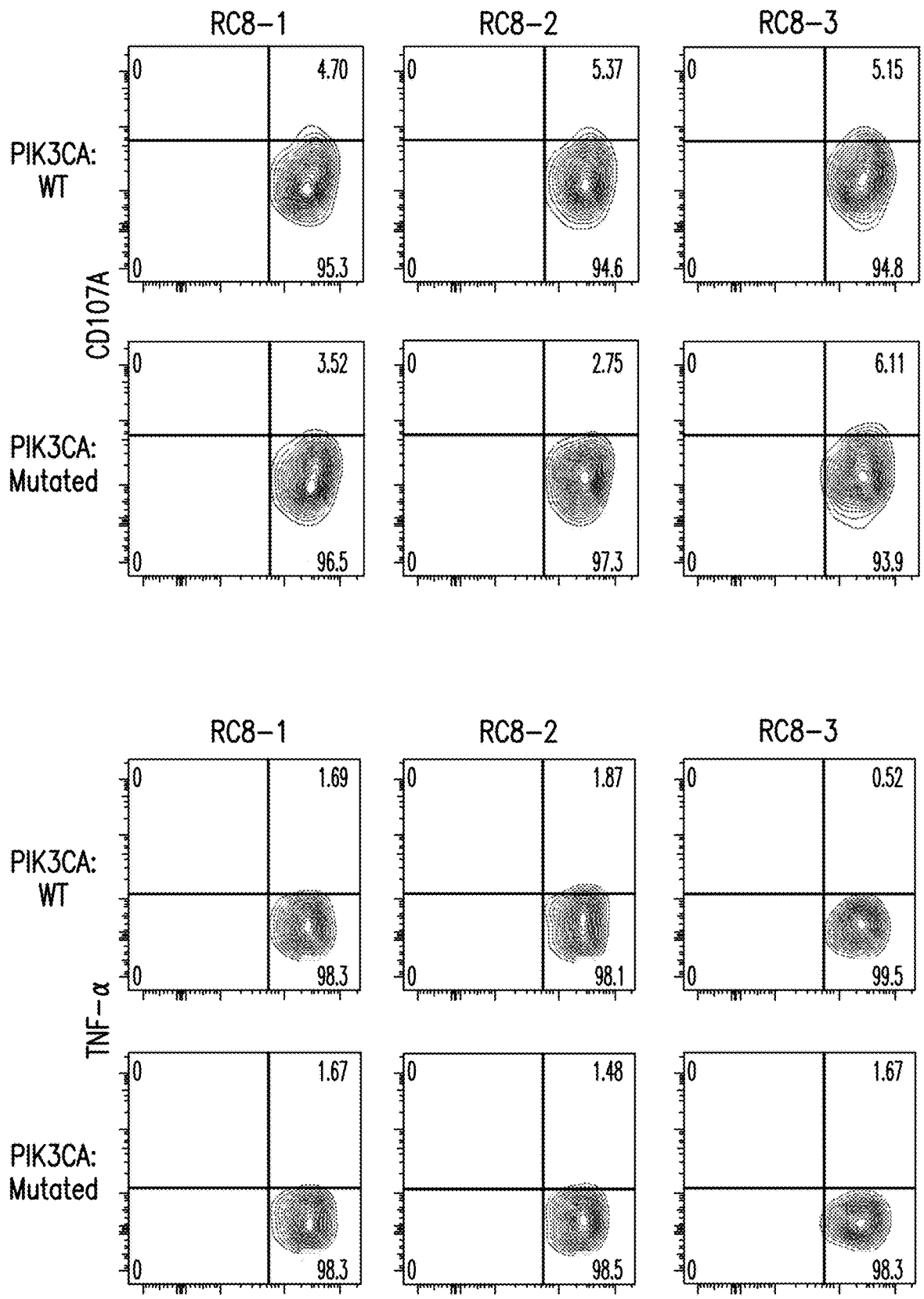
FIG. 25 depicts mutation-specific reactivity of TCRs identified via VDJ sequencing of well RC8. The genetic sequences encoding the alpha and beta chains of mutation-specific TCR derived from VDJ sequencing were cloned into a retroviral vector and stably integrated into allogeneic donor cells. The 3 unique TCR sequences derived from VDJ sequencing of well RC8 were tested. TCR-transduced cells were cocultured with autologous dendritic cells (DC) that had been transiently transfected with RNA encoding either wildtype or mutant PIK3CA. Reactivity was determined by observing the production of the degranulation marker, CD107A, (upper panels) or the inflammatory cytokine, TNF-α, (lower panels) in response to the DC expressing mutated PIK3CA.

Similarly, FIG. 25 shows testing of mutation-specific reactivity of TCRs identified via VDJ sequencing from well RC8 using the same method. None of the three TCRs derived from well RC8 were identified to be mutation-specific.

Figure 26:
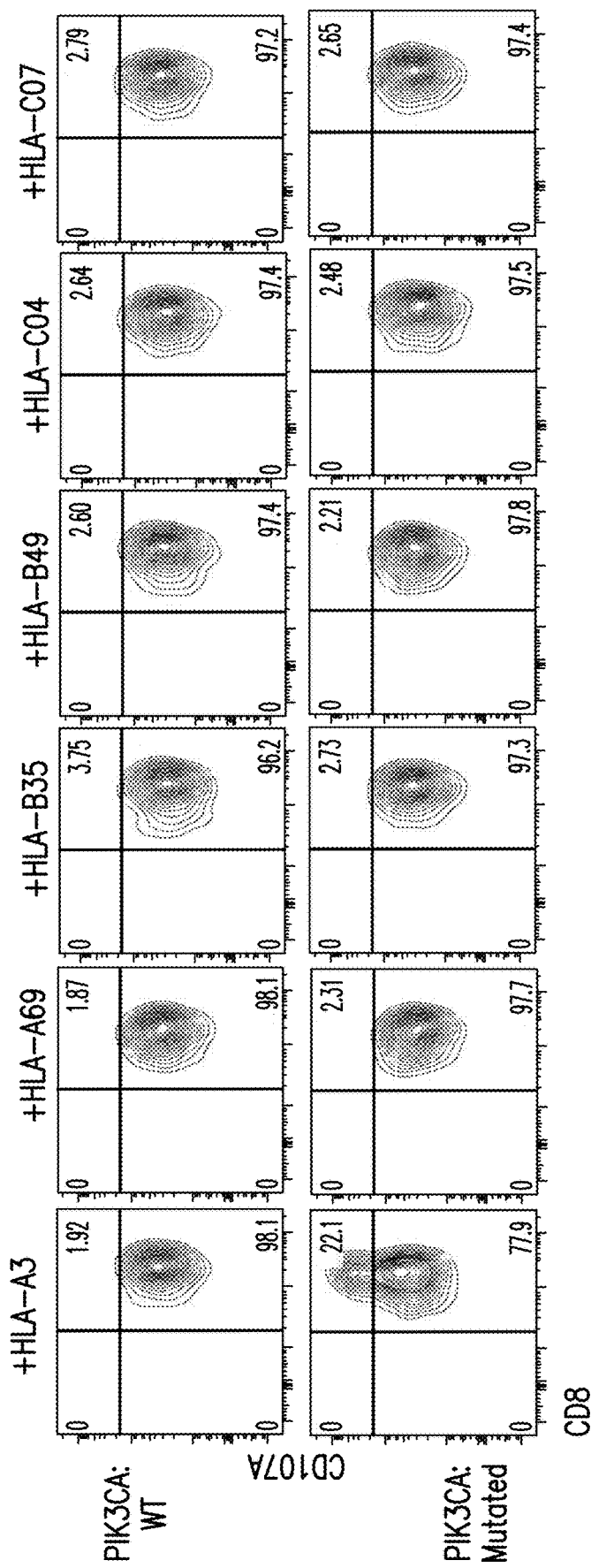
FIG. 26 depicts identification of HLA-A3 as the restriction element for PIK3CA-mutation specific TCR, LB11-2. LB11-2 TCR were retrovirally integrated into the genome of healthy donor T cells. At day 4-6 post-transduction, T cells were incubated with monkey-derived antigen-presenting cells (COS-7) that had been co-electroporated with RNA encoding a single Class I HLA allele, and either the wildtype or mutated PIK3CA RNA. The mutated version comprised a histidine to leucine substitution at position 1047 (H1047L). Cells were gated on CD8+ TCR+ expression. A change in production of the degranulation protein, CD107A, was used to indicate the presence of mutation-specific reactivity in the context of the right HLA allele.
Figure 27:
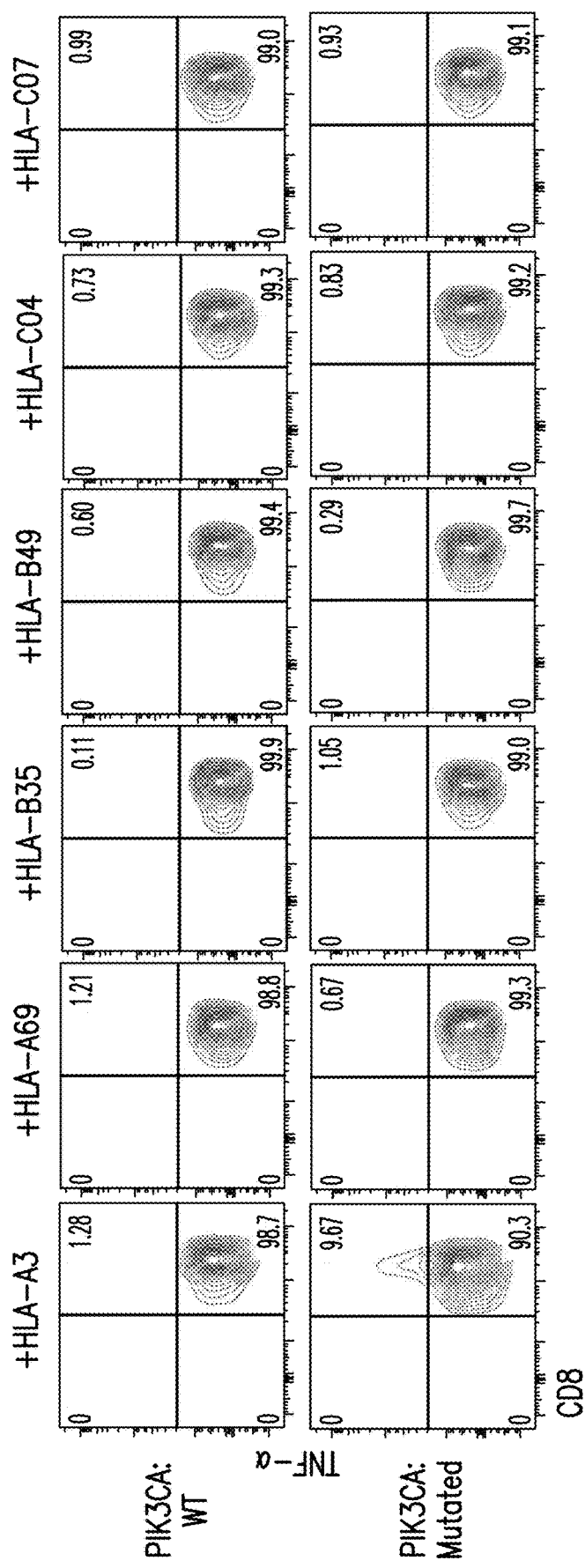
FIG. 27 depicts identification of HLA-A3 as the restriction element for PIK3CA-mutation specific TCR, LB11-2. LB11-2 TCR were retrovirally integrated into the genome of healthy donor T cells. At day 4-6 post-transduction, T cells were incubated with monkey-derived antigen-presenting cells (COS-7) that had been co-electroporated with RNA encoding a single Class I HLA allele, and either the wildtype or mutated PIK3CA RNA. The mutated version comprised a histidine to leucine substitution at position 1047 (H1047L). Cells were gated on CD8+ TCR+ expression. A change in production of the inflammatory cytokine, TNF-α, was used to indicate the presence of mutation-specific reactivity in the context of the right HLA allele.

Furthermore, HLA-A3 was identified as the restriction element for PIK3CA-mutation specific TCR, LB11-2. LB11-2 TCR were retrovirally integrated into the genome of healthy donor T cells. At day 4-6 post-transduction, T cells were incubated with monkey-derived antigen-presenting cells (COS-7) that had been co-electroporated with RNA encoding a single Class I HLA allele, and either the wildtype or mutated PIK3CA RNA. The mutated version comprised a histidine to leucine substitution at position 1047 (H1047L). Cells were gated on CD8+TCR+ expression. As shown in FIGS. 26 and 27, changes in production of the degranulation protein, CD107A and the inflammatory cytokine, TNF-α, respectively, were used to indicate the presence of mutation-specific reactivity in the context of the right HLA allele. The data showed that LB11-2 recognized mutated H1047L in the context of HLA-A3.

Figure 28:
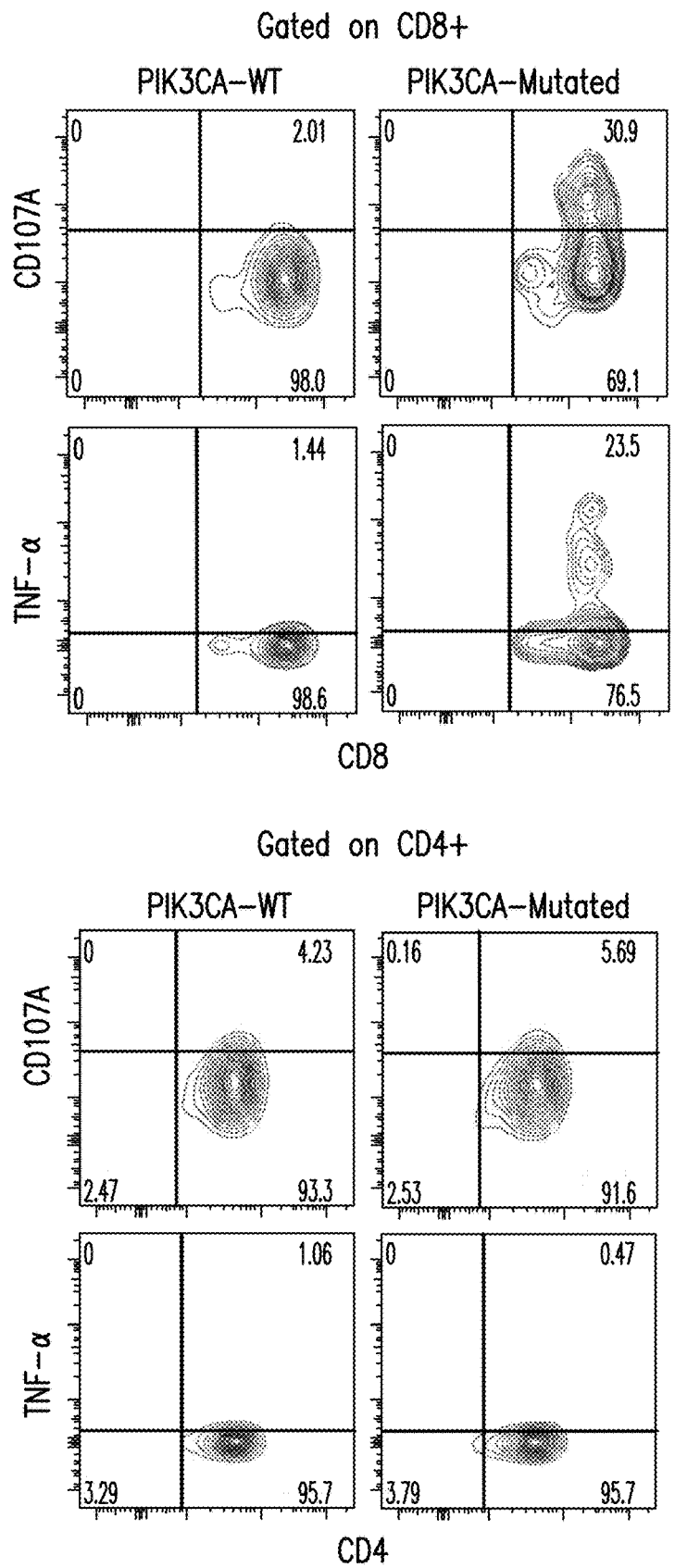
FIG. 28 depicts that PIK3CA-mutant specific TCR, LB11-2, is co-receptor-dependent. LB11-2 TCR were retrovirally integrated into the genome of healthy donor T cells. At day 4-6 post-transduction, T cells were incubated with monkey-derived antigen-presenting cells (COS-7) that had been co-electroporated with RNA encoding HLA-A3, and either the wildtype or mutated PIK3CA RNA. Cells were gated on CD8+TCR+ (upper panels) or CD4+TCR+ (lower panels) expression. A change in production of the CD107A and TNF-α, was used to indicate the presence of mutation-specific reactivity.

Additionally, FIG. 28 shows that PIK3CA-mutant specific TCR, LB11-2, was co-receptor-dependent. LB11-2 TCR were retrovirally integrated into the genome of healthy donor T cells. At day 4-6 post-transduction, T cells were incubated with monkey-derived antigen-presenting cells (COS-7) that had been co-electroporated with RNA encoding HLA-A3, and either the wildtype or mutated PIK3CA RNA. Cells were gated on CD8+TCR+ (upper panels) or CD4+TCR+ (lower panels) expression. A change in production of the CD107A and TNF-α, was used to indicate the presence of mutation-specific reactivity. The data demonstrated that LB11-2 was not functional within the CD4+ T cell, and required the presence of the CD8 coreceptor in order to recognize mutated H1047L.

The sequence of LB11-2 were identified, which comprises: TRBV5-6*01, TRD1*01, TRJ2-7*01, TRAV26-1*02, and TRAJ22*01. The alpha chain variable region comprised SEQ ID NO: 47, and the beta chain variable region comprised SEQ ID NO: 48.

From the foregoing description, it will be apparent that variations and modifications may be made to the invention described herein to adopt it to various usages and conditions. Such embodiments are also within the scope of the following claims.

All patents and publications and sequences referred to by accession or reference number mentioned in this specification are herein incorporated by reference to the same extent as if each independent patent and publication and sequence was specifically and individually indicated to be incorporated by reference.

What is claimed is:

1. A T cell receptor (TCR) comprising:
   a) an alpha (α) chain variable region that comprises a CDR1 comprising the amino acid sequence set forth in SEQ ID NO: 41, a CDR2 comprising the amino acid sequence set forth in SEQ ID NO: 42, and a CDR3 comprising the amino acid sequence set forth in SEQ ID NO: 43; and
   b) a beta (β) chain variable region that comprises a CDR1 comprising the amino acid sequence set forth in SEQ ID NO: 44, a CDR2 comprising the amino acid sequence set forth in SEQ ID NO: 45, and a CDR3 comprising the amino acid sequence set forth in SEQ ID NO: 46.

2. The TCR of claim 1, wherein the α chain variable region comprises an amino acid sequence that is at least 80% identical to the amino acid sequence set forth in SEQ ID NO: 47.

3. The TCR of claim 1, wherein the α chain variable region comprises the amino acid sequence set forth in SEQ ID NO: 47.

4. The TCR of claim 1, wherein the β chain variable region comprising an amino acid sequence that is at least 80% identical to the amino acid sequence set forth in SEQ ID NO: 48.

5. The TCR of claim 1, wherein the β chain variable region comprises the amino acid sequence set forth in SEQ ID NO: 48.

6. The TCR of claim 1, wherein:
   a) the α chain variable region comprises an amino acid sequence that is at least 80% identical to the amino acid sequence set forth in SEQ ID NO: 47; and
   b) the β chain variable region comprises an amino acid sequence that is at least 80% identical to the amino acid sequence set forth in SEQ ID NO: 48.

7. The TCR of claim 1, wherein
   a) the α chain variable region comprises the amino acid sequence set forth in SEQ ID NO: 47; and
   b) the β chain variable region comprises the amino acid sequence set forth in SEQ ID NO: 48.

8. The TCR of claim 1, wherein the extracellular domain comprises i) an α chain comprising the amino acid sequence set forth in SEQ ID NO: 49; and ii) a β chain comprising the amino acid sequence set forth in SEQ ID NO: 50.

9. The TCR of claim 1, wherein the TCR is expressed from a vector.

10. The TCR of claim 1, wherein the TCR further comprises a modified α-chain constant region, a modified β-chain constant region, or both the modified a-chain constant region and the modified β-chain constant region.

11. The TCR of claim 10, wherein the modified α-chain constant region comprises an amino acid sequence that is at least 80% identical to the amino acid sequence set forth in SEQ ID NO: 81.

12. The TCR of claim 10, wherein the modified α-chain constant region comprises the amino acid sequence set forth in SEQ ID NO: 81.

13. The TCR of claim 10, wherein the modified β-chain constant region comprises an amino acid sequence that is at least 80% identical to the amino acid sequence set forth in SEQ ID NO: 83.

14. The TCR of claim 10, wherein the modified β-chain constant region comprises the amino acid sequence set forth in SEQ ID NO: 83.

15. An isolated immunoresponsive cell comprising the TCR of claim 1.

16. The isolated immunoresponsive cell of claim 15, wherein the immunoresponsive cell is transduced with the TCR.

17. The isolated immunoresponsive cell of claim 15, wherein the TCR is constitutively expressed on the surface of the immunoresponsive cell.

18. The isolated immunoresponsive cell of claim 15, wherein the immunoresponsive cell is selected from the group consisting of a T cell, a Natural Killer (NK) cell, a lymphoid progenitor cell, a T cell-precursor cell, a pluripotent stem cell, and a pluripotent stem cell-derived lymphoid cell.

19. The isolated immunoresponsive cell of claim 18, wherein the immunoresponsive cell is a T cell.

20. The isolated immunoresponsive cell of claim 19, wherein the T cell is selected from the group consisting of a cytotoxic T lymphocyte (CTL), a regulatory T cell, and a central memory T cell.

21. A composition comprising the isolated immunoresponsive cell of claim 15.

22. The composition of claim 21, wherein the composition further comprises a pharmaceutically acceptable carrier.

23. A nucleic acid molecule encoding the T cell receptor (TCR) of claim 1.

24. A vector comprising the nucleic acid molecule of claim 23.

25. An isolated host cell comprising the nucleic acid molecule of claim 23.

26. A method for producing an immunoresponsive cell that binds to a human mutant PIK3CA polypeptide, the method comprising introducing into the immunoresponsive cell a nucleic acid molecule that encodes the TCR of claim 1.

27. A method comprising administering to a subject the immunoresponsive cell of claim 15.

28. A kit comprising the immunoresponsive cell of claim 15.

\* \* \* \* \*

SEQUENCE LISTING

```
<160> NUMBER OF SEQ ID NOS: 131

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Ser Ala Ile Tyr Asn
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Gln Ser Ser Gln Arg Glu
1               5

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Ala Val Lys Gly Ser Asp Asp Tyr Lys Leu Ser Phe
1               5                   10

<210> SEQ ID NO 4
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 4

Lys Gly His Ser His
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Gly His Ser His
1               5

<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Ala Ser Ser Pro Val Asn Leu Ala Gly Val Ser Arg Ala Asp Thr
1               5                   10                  15

Gln Tyr Phe

<210> SEQ ID NO 7
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
                20                  25                  30

Pro Glu Gly Glu Asn Leu Val Leu Asn Cys Ser Phe Thr Asp Ser Ala
            35                  40                  45

Ile Tyr Asn Leu Gln Trp Phe Arg Gln Asp Pro Gly Lys Gly Leu Thr
        50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Lys
            100                 105                 110

Gly Ser Asp Asp Tyr Lys Leu Ser Phe Gly Ala Gly Thr Thr Val Thr
        115                 120                 125

Val Arg Ala
    130

<210> SEQ ID NO 8
```

<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Asp Thr Arg Val Leu Cys Cys Ala Val Ile Cys Leu Leu Gly Ala
1               5                   10                  15

Gly Leu Ser Asn Ala Gly Val Met Gln Asn Pro Arg His Leu Val Arg
            20                  25                  30

Arg Arg Gly Gln Glu Ala Arg Leu Arg Cys Ser Pro Met Lys Gly His
        35                  40                  45

Ser His Val Tyr Trp Tyr Arg Gln Leu Pro Glu Glu Gly Leu Lys Phe
    50                  55                  60

Met Val Tyr Leu Gln Lys Glu Asn Ile Ile Asp Glu Ser Gly Met Pro
65                  70                  75                  80

Lys Glu Arg Phe Ser Ala Glu Phe Pro Lys Gly Pro Ser Ile Leu
                85                  90                  95

Arg Ile Gln Gln Val Val Arg Gly Asp Ser Ala Ala Tyr Phe Cys Ala
            100                 105                 110

Ser Ser Pro Val Asn Leu Ala Gly Val Ser Arg Ala Asp Thr Gln Tyr
        115                 120                 125

Phe Gly Pro Gly Thr Arg Leu Thr Val Leu
    130                 135

<210> SEQ ID NO 9
<211> LENGTH: 268
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Lys
            100                 105                 110

Gly Ser Asp Asp Tyr Lys Leu Ser Phe Gly Ala Gly Thr Thr Val Thr
        115                 120                 125

Val Arg Ala Asn Ile Gln Asn Pro Glu Pro Ala Val Tyr Gln Leu Lys
    130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

```
Asp Lys Cys Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
            195                 200                 205

Lys Glu Thr Asn Ala Thr Tyr Pro Ser Ser Asp Val Pro Cys Asp Ala
    210                 215                 220

Thr Leu Thr Glu Lys Ser Phe Glu Thr Asp Met Asn Leu Asn Phe Gln
225                 230                 235                 240

Asn Leu Val Ile Val Leu Arg Ile Leu Leu Lys Val Ala Gly
            245                 250                 255

Phe Asn Leu Leu Met Thr Leu Arg Leu Trp Ser Ser
            260                 265

<210> SEQ ID NO 10
<211> LENGTH: 311
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Asp Thr Arg Val Leu Cys Cys Ala Val Ile Cys Leu Leu Gly Ala
1               5                   10                  15

Gly Leu Ser Asn Ala Gly Val Met Gln Asn Pro Arg His Leu Val Arg
            20                  25                  30

Arg Arg Gly Gln Glu Ala Arg Leu Arg Cys Ser Pro Met Lys Gly His
        35                  40                  45

Ser His Val Tyr Trp Tyr Arg Gln Leu Pro Glu Glu Gly Leu Lys Phe
    50                  55                  60

Met Val Tyr Leu Gln Lys Glu Asn Ile Ile Asp Glu Ser Gly Met Pro
65                  70                  75                  80

Lys Glu Arg Phe Ser Ala Glu Phe Pro Lys Gly Pro Ser Ile Leu
            85                  90                  95

Arg Ile Gln Gln Val Val Arg Gly Asp Ser Ala Ala Tyr Phe Cys Ala
            100                 105                 110

Ser Ser Pro Val Asn Leu Ala Gly Val Ser Arg Ala Asp Thr Gln Tyr
            115                 120                 125

Phe Gly Pro Gly Thr Arg Leu Thr Val Leu Glu Asp Leu Arg Asn Val
    130                 135                 140

Thr Pro Pro Lys Val Ser Leu Phe Glu Pro Ser Lys Ala Glu Ile Ala
145                 150                 155                 160

Asn Lys Gln Lys Ala Thr Leu Val Cys Leu Ala Arg Gly Phe Phe Pro
            165                 170                 175

Asp His Val Glu Leu Ser Trp Trp Val Asn Gly Lys Glu Val His Ser
            180                 185                 190

Gly Val Cys Thr Asp Pro Gln Ala Tyr Lys Glu Ser Asn Tyr Ser Tyr
        195                 200                 205

Cys Leu Ser Ser Arg Leu Arg Val Ser Ala Thr Phe Trp His Asn Pro
    210                 215                 220

Arg Asn His Phe Arg Cys Gln Val Gln Phe His Gly Leu Ser Glu Glu
225                 230                 235                 240

Asp Lys Trp Pro Glu Gly Ser Pro Lys Pro Val Thr Gln Asn Ile Ser
            245                 250                 255

Ala Glu Ala Trp Gly Arg Ala Asp Cys Gly Ile Thr Ser Ala Ser Tyr
```

```
              260                 265                 270
Gln Gln Gly Val Leu Ser Ala Thr Ile Leu Tyr Glu Ile Leu Leu Gly
            275                 280                 285

Lys Ala Thr Leu Tyr Ala Val Leu Val Ser Thr Leu Val Val Met Ala
        290                 295                 300

Met Val Lys Arg Lys Asn Ser
305                 310

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Ser Gly Phe Asn Gly
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asn Val Leu Asp Gly Leu
1               5

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Cys Ala Val Thr Ser Trp Gly Lys Leu Gln Phe
1               5                   10

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Gly His Thr Ala
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Phe Gln Gly Asn Ser Ala
```

```
<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Ala Ser Ser Pro Arg Gly Tyr Gln Pro Gln His Phe
1               5                   10

<210> SEQ ID NO 17
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Trp Gly Val Phe Leu Leu Tyr Val Ser Met Lys Met Gly Gly Thr
1               5                   10                  15

Thr Gly Gln Asn Ile Asp Gln Pro Thr Glu Met Thr Ala Thr Glu Gly
            20                  25                  30

Ala Ile Val Gln Ile Asn Cys Thr Tyr Gln Thr Ser Gly Phe Asn Gly
        35                  40                  45

Leu Phe Trp Tyr Gln Gln His Ala Gly Glu Ala Pro Thr Phe Leu Ser
    50                  55                  60

Tyr Asn Val Leu Asp Gly Leu Glu Glu Lys Gly Arg Phe Ser Ser Phe
65                  70                  75                  80

Leu Ser Arg Ser Lys Gly Tyr Ser Tyr Leu Leu Leu Lys Glu Leu Gln
                85                  90                  95

Met Lys Asp Ser Ala Ser Tyr Leu Cys Ala Val Thr Ser Trp Gly Lys
            100                 105                 110

Leu Gln Phe Lys Leu Gln Phe Gly Ala Gly Thr Gln Val Val Val Thr
        115                 120                 125

Pro

<210> SEQ ID NO 18
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Gly Thr Arg Leu Leu Phe Trp Val Ala Phe Cys Leu Leu Gly Ala
1               5                   10                  15

Tyr His Thr Gly Ala Gly Val Ser Gln Ser Pro Ser Asn Lys Val Thr
            20                  25                  30

Glu Lys Gly Lys Asp Val Glu Leu Arg Cys Asp Pro Ile Ser Gly His
        35                  40                  45

Thr Ala Leu Tyr Trp Tyr Arg Gln Arg Leu Gly Gln Gly Leu Glu Phe
    50                  55                  60

Leu Ile Tyr Phe Gln Gly Asn Ser Ala Pro Asp Lys Ser Gly Leu Pro
65                  70                  75                  80
```

Ser Asp Arg Phe Ser Ala Glu Arg Thr Gly Glu Ser Val Ser Thr Leu
            85                  90                  95

Thr Ile Gln Arg Thr Gln Gln Glu Asp Ser Ala Val Tyr Leu Cys Ala
            100                 105                 110

Ser Ser Pro Arg Gly Tyr Gln Pro Gln His Phe Gly Asp Gly Thr Arg
            115                 120                 125

Leu Ser Ile Leu
    130

<210> SEQ ID NO 19
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Trp Gly Val Phe Leu Leu Tyr Val Ser Met Lys Met Gly Gly Thr
1               5                   10                  15

Thr Gly Gln Asn Ile Asp Gln Pro Thr Glu Met Thr Ala Thr Glu Gly
            20                  25                  30

Ala Ile Val Gln Ile Asn Cys Thr Tyr Gln Thr Ser Gly Phe Asn Gly
        35                  40                  45

Leu Phe Trp Tyr Gln Gln His Ala Gly Glu Ala Pro Thr Phe Leu Ser
    50                  55                  60

Tyr Asn Val Leu Asp Gly Leu Glu Glu Lys Gly Arg Phe Ser Ser Phe
65                  70                  75                  80

Leu Ser Arg Ser Lys Gly Tyr Ser Tyr Leu Leu Leu Lys Glu Leu Gln
                85                  90                  95

Met Lys Asp Ser Ala Ser Tyr Leu Cys Ala Val Thr Ser Trp Gly Lys
            100                 105                 110

Leu Gln Phe Lys Leu Gln Phe Gly Ala Gly Thr Gln Val Val Val Thr
        115                 120                 125

Pro Asn Ile Gln Asn Pro Glu Pro Ala Val Tyr Gln Leu Lys Asp Pro
    130                 135                 140

Arg Ser Gln Asp Ser Thr Leu Cys Leu Phe Thr Asp Phe Asp Ser Gln
145                 150                 155                 160

Ile Asn Val Pro Lys Thr Met Glu Ser Gly Thr Phe Ile Thr Asp Lys
                165                 170                 175

Cys Val Leu Asp Met Lys Ala Met Asp Ser Lys Ser Asn Gly Ala Ile
            180                 185                 190

Ala Trp Ser Asn Gln Thr Ser Phe Thr Cys Gln Asp Ile Phe Lys Glu
        195                 200                 205

Thr Asn Ala Thr Tyr Pro Ser Ser Asp Val Pro Cys Asp Ala Thr Leu
    210                 215                 220

Thr Glu Lys Ser Phe Glu Thr Asp Met Asn Leu Asn Phe Gln Asn Leu
225                 230                 235                 240

Leu Val Ile Val Leu Arg Ile Leu Leu Leu Lys Val Ala Gly Phe Asn
                245                 250                 255

Leu Leu Met Thr Leu Arg Leu Trp Ser Ser
            260                 265

<210> SEQ ID NO 20
<211> LENGTH: 305
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Gly Thr Arg Leu Leu Phe Trp Val Ala Phe Cys Leu Leu Gly Ala
1               5                   10                  15

Tyr His Thr Gly Ala Gly Val Ser Gln Ser Pro Ser Asn Lys Val Thr
            20                  25                  30

Glu Lys Gly Lys Asp Val Glu Leu Arg Cys Asp Pro Ile Ser Gly His
        35                  40                  45

Thr Ala Leu Tyr Trp Tyr Arg Gln Arg Leu Gly Gln Gly Leu Glu Phe
    50                  55                  60

Leu Ile Tyr Phe Gln Gly Asn Ser Ala Pro Asp Lys Ser Gly Leu Pro
65                  70                  75                  80

Ser Asp Arg Phe Ser Ala Glu Arg Thr Gly Glu Ser Val Ser Thr Leu
                85                  90                  95

Thr Ile Gln Arg Thr Gln Gln Glu Asp Ser Ala Val Tyr Leu Cys Ala
            100                 105                 110

Ser Ser Pro Arg Gly Tyr Gln Pro Gln His Phe Gly Asp Gly Thr Arg
        115                 120                 125

Leu Ser Ile Leu Glu Asp Leu Arg Asn Val Thr Pro Pro Lys Val Ser
130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Cys Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Thr Leu Val Val Met Ala Met Val Lys Arg Lys Asn
    290                 295                 300

Ser
305

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Thr Ser Asp Gln Ser Tyr Gly
1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Gly Ser Tyr Asp Glu Gln Asn
1               5

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Cys Ala Met Arg Glu Val Leu Asp Asn Thr Asp Lys Leu Ile Phe
1               5                   10                  15

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Gly His Ser His
1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Leu Gln Lys Glu Asn Ile
1               5

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Cys Ala Ser Ser Pro Pro Glu Ala Gly Leu Asp Thr Glu Ala Phe Phe
1               5                   10                  15

<210> SEQ ID NO 27
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Gln Ser Tyr Gly Leu Phe Trp Tyr Lys Gln Pro Ser Ser Gly Glu
    50                  55                  60

Met Ile Phe Leu Ile Tyr Gln Gly Ser Tyr Asp Glu Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Arg Glu Val Leu Asp Asn Thr Asp Lys Leu Ile Phe Gly Thr
        115                 120                 125

Gly Thr Arg Leu Gln Val Phe Pro
    130                 135

<210> SEQ ID NO 28
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Asp Thr Arg Val Leu Cys Cys Ala Val Ile Cys Leu Leu Gly Ala
1               5                   10                  15

Gly Leu Ser Asn Ala Gly Val Met Gln Asn Pro Arg His Leu Val Arg
            20                  25                  30

Arg Arg Gly Gln Glu Ala Arg Leu Arg Cys Ser Pro Met Lys Gly His
        35                  40                  45

Ser His Val Tyr Trp Tyr Arg Gln Leu Pro Glu Glu Gly Leu Lys Phe
    50                  55                  60

Met Val Tyr Leu Gln Lys Glu Asn Ile Ile Asp Glu Ser Gly Met Pro
65                  70                  75                  80

Lys Glu Arg Phe Ser Ala Glu Phe Pro Lys Glu Gly Pro Ser Ile Leu
                85                  90                  95

Arg Ile Gln Gln Val Val Arg Gly Asp Ser Ala Ala Tyr Phe Cys Ala
            100                 105                 110

Ser Ser Pro Pro Glu Ala Gly Leu Asp Thr Glu Ala Phe Phe Gly Gln
        115                 120                 125

Gly Thr Arg Leu Thr Val Val
    130                 135

<210> SEQ ID NO 29
<211> LENGTH: 273
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

```
Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Gln Ser Tyr Gly Leu Phe Trp Tyr Lys Gln Pro Ser Ser Gly Glu
    50                  55                  60

Met Ile Phe Leu Ile Tyr Gln Gly Ser Tyr Asp Glu Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
                100                 105                 110

Ala Met Arg Glu Val Leu Asp Asn Thr Asp Lys Leu Ile Phe Gly Thr
            115                 120                 125

Gly Thr Arg Leu Gln Val Phe Pro Asn Ile Gln Asn Pro Glu Pro Ala
            130                 135                 140

Val Tyr Gln Leu Lys Asp Pro Arg Ser Gln Asp Ser Thr Leu Cys Leu
145                 150                 155                 160

Phe Thr Asp Phe Asp Ser Gln Ile Asn Val Pro Lys Thr Met Glu Ser
                165                 170                 175

Gly Thr Phe Ile Thr Asp Lys Cys Val Leu Asp Met Lys Ala Met Asp
                180                 185                 190

Ser Lys Ser Asn Gly Ala Ile Ala Trp Ser Asn Gln Thr Ser Phe Thr
            195                 200                 205

Cys Gln Asp Ile Phe Lys Glu Thr Asn Ala Thr Tyr Pro Ser Ser Asp
            210                 215                 220

Val Pro Cys Asp Ala Thr Leu Thr Glu Lys Ser Phe Glu Thr Asp Met
225                 230                 235                 240

Asn Leu Asn Phe Gln Asn Leu Leu Val Ile Val Leu Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 30
<211> LENGTH: 308
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Asp Thr Arg Val Leu Cys Cys Ala Val Ile Cys Leu Leu Gly Ala
1               5                   10                  15

Gly Leu Ser Asn Ala Gly Val Met Gln Asn Pro Arg His Leu Val Arg
            20                  25                  30

Arg Arg Gly Gln Glu Ala Arg Leu Arg Cys Ser Pro Met Lys Gly His
            35                  40                  45

Ser His Val Tyr Trp Tyr Arg Gln Leu Pro Glu Glu Gly Leu Lys Phe
        50                  55                  60

Met Val Tyr Leu Gln Lys Glu Asn Ile Ile Asp Glu Ser Gly Met Pro
65                  70                  75                  80
```

```
Lys Glu Arg Phe Ser Ala Glu Phe Pro Lys Glu Gly Pro Ser Ile Leu
                85                  90                  95

Arg Ile Gln Gln Val Val Arg Gly Asp Ser Ala Ala Tyr Phe Cys Ala
            100                 105                 110

Ser Ser Pro Pro Glu Ala Gly Leu Asp Thr Glu Ala Phe Phe Gly Gln
        115                 120                 125

Gly Thr Arg Leu Thr Val Val Glu Asp Leu Arg Asn Val Thr Pro Pro
130                 135                 140

Lys Val Ser Leu Phe Glu Pro Ser Lys Ala Glu Ile Ala Asn Lys Gln
145                 150                 155                 160

Lys Ala Thr Leu Val Cys Leu Ala Arg Gly Phe Phe Pro Asp His Val
                165                 170                 175

Glu Leu Ser Trp Trp Val Asn Gly Lys Glu Val His Ser Gly Val Cys
            180                 185                 190

Thr Asp Pro Gln Ala Tyr Lys Glu Ser Asn Tyr Ser Tyr Cys Leu Ser
        195                 200                 205

Ser Arg Leu Arg Val Ser Ala Thr Phe Trp His Asn Pro Arg Asn His
210                 215                 220

Phe Arg Cys Gln Val Gln Phe His Gly Leu Ser Glu Glu Asp Lys Trp
225                 230                 235                 240

Pro Glu Gly Ser Pro Lys Pro Val Thr Gln Asn Ile Ser Ala Glu Ala
                245                 250                 255

Trp Gly Arg Ala Asp Cys Gly Ile Thr Ser Ala Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Thr Leu Val Val Met Ala Met Val Lys
290                 295                 300

Arg Lys Asn Ser
305

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asn Ser Ala Phe Gln Tyr
1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Tyr Ser Ser Gly Asn
1               5

<210> SEQ ID NO 33
<211> LENGTH: 13
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 33

Cys Ala Met Asn Ser Gly Gly Tyr Gln Lys Val Thr Phe
1               5                   10

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Phe Gln Ala Thr Thr
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Asn Glu Gly Ser Lys Ala
1               5

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Cys Ser Ala Arg Glu Gln Gly Pro Leu Glu Glu Gln Tyr Phe
1               5                   10

<210> SEQ ID NO 37
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

```
Phe Ile Arg Asp Ser Gln Pro Ser Asp Ser Ala Thr Tyr Leu Cys Ala
            100                 105                 110

Met Asn Ser Gly Gly Tyr Gln Lys Val Thr Phe Gly Ile Gly Thr Lys
        115                 120                 125

Leu Gln Val Ile Pro
    130

<210> SEQ ID NO 38
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Leu Leu Leu Leu Leu Leu Gly Pro Ala Gly Ser Gly Leu Gly
1               5                   10                  15

Ala Val Val Ser Gln His Pro Ser Arg Val Ile Cys Lys Ser Gly Thr
            20                  25                  30

Ser Val Lys Ile Glu Cys Arg Ser Leu Asp Phe Gln Ala Thr Thr Met
        35                  40                  45

Phe Trp Tyr Arg Gln Phe Pro Lys Gln Ser Leu Met Leu Met Ala Thr
    50                  55                  60

Ser Asn Glu Gly Ser Lys Ala Thr Tyr Glu Gln Gly Val Glu Lys Asp
65                  70                  75                  80

Lys Phe Leu Ile Asn His Ala Ser Leu Thr Leu Ser Thr Leu Thr Val
                85                  90                  95

Thr Ser Ala His Pro Glu Asp Ser Ser Phe Tyr Ile Cys Ser Ala Cys
            100                 105                 110

Ser Ala Arg Glu Gln Gly Pro Leu Glu Glu Gln Tyr Phe Gly Pro Gly
        115                 120                 125

Thr Arg Leu Thr Val Thr
    130

<210> SEQ ID NO 39
<211> LENGTH: 270
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110
```

Met Asn Ser Gly Gly Tyr Gln Lys Val Thr Phe Gly Ile Gly Thr Lys
                115                 120                 125

Leu Gln Val Ile Pro Asn Ile Gln Asn Pro Glu Pro Ala Val Tyr Gln
130                 135                 140

Leu Lys Asp Pro Arg Ser Gln Asp Ser Thr Leu Cys Leu Phe Thr Asp
145                 150                 155                 160

Phe Asp Ser Gln Ile Asn Val Pro Lys Thr Met Glu Ser Gly Thr Phe
                165                 170                 175

Ile Thr Asp Lys Cys Val Leu Asp Met Lys Ala Met Asp Ser Lys Ser
                180                 185                 190

Asn Gly Ala Ile Ala Trp Ser Asn Gln Thr Ser Phe Thr Cys Gln Asp
                195                 200                 205

Ile Phe Lys Glu Thr Asn Ala Thr Tyr Pro Ser Ser Asp Val Pro Cys
                210                 215                 220

Asp Ala Thr Leu Thr Glu Lys Ser Phe Glu Thr Asp Met Asn Leu Asn
225                 230                 235                 240

Phe Gln Asn Leu Leu Val Ile Val Leu Arg Ile Leu Leu Leu Lys Val
                245                 250                 255

Ala Gly Phe Asn Leu Leu Met Thr Leu Arg Leu Trp Ser Ser
                260                 265                 270

<210> SEQ ID NO 40
<211> LENGTH: 307
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Leu Leu Leu Leu Leu Leu Gly Pro Ala Gly Ser Gly Leu Gly
1               5                   10                  15

Ala Val Val Ser Gln His Pro Ser Arg Val Ile Cys Lys Ser Gly Thr
                20                  25                  30

Ser Val Lys Ile Glu Cys Arg Ser Leu Asp Phe Gln Ala Thr Thr Met
                35                  40                  45

Phe Trp Tyr Arg Gln Phe Pro Lys Gln Ser Leu Met Leu Met Ala Thr
50                  55                  60

Ser Asn Glu Gly Ser Lys Ala Thr Tyr Glu Gln Gly Val Glu Lys Asp
65                  70                  75                  80

Lys Phe Leu Ile Asn His Ala Ser Leu Thr Leu Ser Thr Leu Thr Val
                85                  90                  95

Thr Ser Ala His Pro Glu Asp Ser Ser Phe Tyr Ile Cys Ser Ala Cys
                100                 105                 110

Ser Ala Arg Glu Gln Gly Pro Leu Glu Glu Gln Tyr Phe Gly Pro Gly
                115                 120                 125

Thr Arg Leu Thr Val Thr Glu Asp Leu Arg Asn Val Thr Pro Pro Lys
                130                 135                 140

Val Ser Leu Phe Glu Pro Ser Lys Ala Glu Ile Ala Asn Lys Gln Lys
145                 150                 155                 160

Ala Thr Leu Val Cys Leu Ala Arg Gly Phe Phe Pro Asp His Val Glu
                165                 170                 175

Leu Ser Trp Trp Val Asn Gly Lys Glu Val His Ser Gly Val Cys Thr
                180                 185                 190

Asp Pro Gln Ala Tyr Lys Glu Ser Asn Tyr Ser Tyr Cys Leu Ser Ser
                195                 200                 205

```
Arg Leu Arg Val Ser Ala Thr Phe Trp His Asn Pro Arg Asn His Phe
    210                 215                 220
Arg Cys Gln Val Gln Phe His Gly Leu Ser Glu Glu Asp Lys Trp Pro
225                 230                 235                 240
Glu Gly Ser Pro Lys Pro Val Thr Gln Asn Ile Ser Ala Glu Ala Trp
                245                 250                 255
Gly Arg Ala Asp Cys Gly Ile Thr Ser Ala Ser Tyr Gln Gln Gly Val
            260                 265                 270
Leu Ser Ala Thr Ile Leu Tyr Glu Ile Leu Leu Gly Lys Ala Thr Leu
        275                 280                 285
Tyr Ala Val Leu Val Ser Thr Leu Val Val Met Ala Met Val Lys Arg
    290                 295                 300
Lys Asn Ser
305

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Thr Ile Ser Gly Asn Glu Tyr
1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Leu Lys Asn Asn
1               5

<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Cys Ile Val Arg Val Ala Gly Ser Ala Arg Gln Leu Thr Phe
1               5                   10

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ser Gly His Asp Thr
1               5
```

```
<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Tyr Tyr Glu Glu Glu Glu
1               5

<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Cys Ala Ser Ser Phe Gly Thr Ala Thr Tyr Glu Gln Tyr Phe
1               5                   10

<210> SEQ ID NO 47
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Arg Leu Val Ala Arg Val Thr Val Phe Leu Thr Phe Gly Thr Ile
1               5                   10                  15

Ile Asp Ala Lys Thr Thr Gln Pro Pro Ser Met Asp Cys Ala Glu Gly
                20                  25                  30

Arg Ala Ala Asn Leu Pro Cys Asn His Ser Thr Ile Ser Gly Asn Glu
            35                  40                  45

Tyr Val Tyr Trp Tyr Arg Gln Ile His Ser Gln Gly Pro Gln Tyr Ile
        50                  55                  60

Ile His Gly Leu Lys Asn Asn Glu Thr Asn Glu Met Ala Ser Leu Ile
65                  70                  75                  80

Ile Thr Glu Asp Arg Lys Ser Ser Thr Leu Ile Leu Pro His Ala Thr
                85                  90                  95

Leu Arg Asp Thr Ala Val Tyr Tyr Cys Ile Val Arg Val Ala Gly Ser
            100                 105                 110

Ala Arg Gln Leu Thr Phe Gly Ser Gly Thr Gln Leu Thr Val Leu Pro
        115                 120                 125

<210> SEQ ID NO 48
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Gly Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
                20                  25                  30
```

```
Thr Arg Gly Gln Gln Val Thr Leu Arg Cys Ser Pro Lys Ser Gly His
        35                  40                  45

Asp Thr Val Ser Trp Tyr Gln Gln Ala Leu Gly Gln Gly Pro Gln Phe
 50                  55                  60

Ile Phe Gln Tyr Tyr Glu Glu Glu Arg Gln Arg Gly Asn Phe Pro
 65                  70                  75                  80

Asp Arg Phe Ser Gly His Gln Phe Pro Asn Tyr Ser Ser Glu Leu Asn
                 85                  90                  95

Val Asn Ala Leu Leu Leu Gly Asp Ser Ala Leu Tyr Leu Cys Ala Ser
            100                 105                 110

Ser Phe Gly Thr Ala Thr Tyr Glu Gln Tyr Phe Gly Pro Gly Thr Arg
        115                 120                 125

Leu Thr Val Thr
    130
```

<210> SEQ ID NO 49
<211> LENGTH: 265
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

```
Met Arg Leu Val Ala Arg Val Thr Val Phe Leu Thr Phe Gly Thr Ile
 1               5                  10                  15

Ile Asp Ala Lys Thr Thr Gln Pro Pro Ser Met Asp Cys Ala Glu Gly
                 20                  25                  30

Arg Ala Ala Asn Leu Pro Cys Asn His Ser Thr Ile Ser Gly Asn Glu
            35                  40                  45

Tyr Val Tyr Trp Tyr Arg Gln Ile His Ser Gln Gly Pro Gln Tyr Ile
 50                  55                  60

Ile His Gly Leu Lys Asn Asn Glu Thr Asn Glu Met Ala Ser Leu Ile
 65                  70                  75                  80

Ile Thr Glu Asp Arg Lys Ser Ser Thr Leu Ile Leu Pro His Ala Thr
                 85                  90                  95

Leu Arg Asp Thr Ala Val Tyr Tyr Cys Ile Val Arg Val Ala Gly Ser
            100                 105                 110

Ala Arg Gln Leu Thr Phe Gly Ser Gly Thr Gln Leu Thr Val Leu Pro
        115                 120                 125

Asn Ile Gln Asn Pro Glu Pro Ala Val Tyr Gln Leu Lys Asp Pro Arg
130                 135                 140

Ser Gln Asp Ser Thr Leu Cys Leu Phe Thr Asp Phe Asp Ser Gln Ile
145                 150                 155                 160

Asn Val Pro Lys Thr Met Glu Ser Gly Thr Phe Ile Thr Asp Lys Cys
                165                 170                 175

Val Leu Asp Met Lys Ala Met Asp Ser Lys Ser Asn Gly Ala Ile Ala
            180                 185                 190

Trp Ser Asn Gln Thr Ser Phe Thr Cys Gln Asp Ile Phe Lys Glu Thr
        195                 200                 205

Asn Ala Thr Tyr Pro Ser Ser Asp Val Pro Cys Asp Ala Thr Leu Thr
    210                 215                 220

Glu Lys Ser Phe Glu Thr Asp Met Asn Leu Asn Phe Gln Asn Leu Leu
225                 230                 235                 240

Val Ile Val Leu Arg Ile Leu Leu Leu Lys Val Ala Gly Phe Asn Leu
                245                 250                 255
```

```
Leu Met Thr Leu Arg Leu Trp Ser Ser
        260                 265
```

```
<210> SEQ ID NO 50
<211> LENGTH: 305
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Met Gly Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
            20                  25                  30

Thr Arg Gly Gln Gln Val Thr Leu Arg Cys Ser Pro Lys Ser Gly His
        35                  40                  45

Asp Thr Val Ser Trp Tyr Gln Gln Ala Leu Gly Gln Gly Pro Gln Phe
    50                  55                  60

Ile Phe Gln Tyr Tyr Glu Glu Glu Arg Gln Arg Gly Asn Phe Pro
65                  70                  75                  80

Asp Arg Phe Ser Gly His Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
            100                 105                 110

Ser Phe Gly Thr Ala Thr Tyr Glu Gln Tyr Phe Gly Pro Gly Thr Arg
        115                 120                 125

Leu Thr Val Thr Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Cys Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Thr Leu Val Val Met Ala Met Val Lys Arg Lys Asn
    290                 295                 300

Ser
305
```

```
<210> SEQ ID NO 51
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 51

Asp Ser Ala Ser Asn Tyr
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ile Arg Ser Asn Val Gly Glu
1               5

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Cys Ala Ala Ser Ile Pro Gly Thr Ala Ser Lys Leu Thr Phe
1               5                   10

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Met Asn His Glu Tyr
1               5

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Met Asn Val Glu Val
1               5

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Cys Ala Ser Ser Pro Tyr Arg Gln Gly Ser Tyr Gly Tyr Thr Phe
1               5                   10                  15
```

<210> SEQ ID NO 57
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
                20                  25                  30

Gln Glu Gly Asp Ser Ala Val Ile Lys Cys Thr Tyr Ser Asp Ser Ala
            35                  40                  45

Ser Asn Tyr Phe Pro Trp Tyr Lys Gln Glu Leu Gly Lys Gly Pro Gln
    50                  55                  60

Leu Ile Ile Asp Ile Arg Ser Asn Val Gly Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Ser
                100                 105                 110

Ile Pro Gly Thr Ala Ser Lys Leu Thr Phe Gly Thr Gly Thr Arg Leu
            115                 120                 125

Gln Val Thr Leu
    130

<210> SEQ ID NO 58
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
                20                  25                  30

Val Thr Gly Lys Lys Leu Thr Val Thr Cys Ser Gln Asn Met Asn His
            35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
                100                 105                 110

Ser Pro Tyr Arg Gln Gly Ser Tyr Gly Tyr Thr Phe Gly Ser Gly Thr
            115                 120                 125

Arg Leu Thr Val Val
    130

<210> SEQ ID NO 59

<211> LENGTH: 269
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Gly Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Ser
            100                 105                 110

Ile Pro Gly Thr Ala Ser Lys Leu Thr Phe Gly Thr Gly Thr Arg Leu
        115                 120                 125

Gln Val Thr Leu Asn Ile Gln Asn Pro Glu Pro Ala Val Tyr Gln Leu
    130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Cys Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
        195                 200                 205

Phe Lys Glu Thr Asn Ala Thr Tyr Pro Ser Ser Asp Val Pro Cys Asp
    210                 215                 220

Ala Thr Leu Thr Glu Lys Ser Phe Glu Thr Asp Met Asn Leu Asn Phe
225                 230                 235                 240

Gln Asn Leu Leu Val Ile Val Leu Arg Ile Leu Leu Leu Lys Val Ala
                245                 250                 255

Gly Phe Asn Leu Leu Met Thr Leu Arg Leu Trp Ser Ser
            260                 265

<210> SEQ ID NO 60
<211> LENGTH: 306
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

```
Glu Tyr Met Ser Trp Tyr Arg Gln Asp Pro Gly Leu Gly Leu Arg Gln
        50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Pro Tyr Arg Gln Gly Ser Tyr Gly Tyr Thr Phe Gly Ser Gly Thr
        115                 120                 125

Arg Leu Thr Val Val Glu Asp Leu Arg Asn Val Thr Pro Pro Lys Val
        130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Cys Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
        210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr Gln Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Thr Leu Val Val Met Ala Met Val Lys Arg Lys
        290                 295                 300

Asn Ser
305

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asn Thr Ala Phe Asp Tyr
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ile Arg Pro Asp Val Ser Glu
1               5
```

<210> SEQ ID NO 63
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Cys Ala Ala Ser Thr Gly Asn Phe Asn Lys Phe Tyr Phe
1               5                   10

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ser Gly His Asn Ser
1               5

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Phe Asn Asn Asn Val Pro
1               5

<210> SEQ ID NO 66
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Cys Ala Ser Asn Arg Gln Gly Thr Val Thr Glu Ala Phe Phe
1               5                   10

<210> SEQ ID NO 67
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Asp Lys Ile Leu Gly Ala Ser Phe Leu Val Leu Trp Leu Gln Leu
1               5                   10                  15

Cys Trp Val Ser Gly Gln Gln Lys Glu Lys Ser Asp Gln Gln Gln Val
                20                  25                  30

Lys Gln Ser Pro Gln Ser Leu Ile Val Gln Lys Gly Gly Ile Ser Ile
        35                  40                  45

Ile Asn Cys Ala Tyr Glu Asn Thr Ala Phe Asp Tyr Phe Pro Trp Tyr
    50                  55                  60

```
Gln Gln Phe Pro Gly Lys Gly Pro Ala Leu Leu Ile Ala Ile Arg Pro
 65                  70                  75                  80

Asp Val Ser Glu Lys Lys Glu Gly Arg Phe Thr Ile Ser Phe Asn Lys
                 85                  90                  95

Ser Ala Lys Gln Phe Ser Leu His Ile Met Asp Ser Gln Pro Gly Asp
            100                 105                 110

Ser Ala Thr Tyr Phe Cys Ala Ala Ser Thr Gly Asn Phe Asn Lys Phe
        115                 120                 125

Tyr Phe Gly Ser Gly Thr Lys Leu Asn Val Lys Pro
    130                 135                 140

<210> SEQ ID NO 68
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Met Asp Ser Trp Thr Phe Cys Cys Val Ser Leu Cys Ile Leu Val Ala
 1               5                  10                  15

Lys His Thr Asp Ala Gly Val Ile Gln Ser Pro Arg His Glu Val Thr
                20                  25                  30

Glu Met Gly Gln Glu Val Thr Leu Arg Cys Lys Pro Ile Ser Gly His
            35                  40                  45

Asn Ser Leu Phe Trp Tyr Arg Gln Thr Met Met Arg Gly Leu Glu Leu
 50                  55                  60

Leu Ile Tyr Phe Asn Asn Asn Val Pro Ile Asp Asp Ser Gly Met Pro
 65                  70                  75                  80

Glu Asp Arg Phe Ser Ala Lys Met Pro Asn Ala Ser Phe Ser Thr Leu
                 85                  90                  95

Lys Ile Gln Pro Ser Glu Pro Arg Asp Ser Ala Val Tyr Phe Cys Ala
            100                 105                 110

Ser Asn Arg Gln Gly Thr Val Thr Glu Ala Phe Phe Gly Gln Gly Thr
        115                 120                 125

Arg Leu Thr Val Val
    130

<210> SEQ ID NO 69
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Met Asp Lys Ile Leu Gly Ala Ser Phe Leu Val Leu Trp Leu Gln Leu
 1               5                  10                  15

Cys Trp Val Ser Gly Gln Gln Lys Glu Lys Ser Asp Gln Gln Gln Val
                20                  25                  30

Lys Gln Ser Pro Gln Ser Leu Ile Val Gln Lys Gly Gly Ile Ser Ile
            35                  40                  45

Ile Asn Cys Ala Tyr Glu Asn Thr Ala Phe Asp Tyr Phe Pro Trp Tyr
 50                  55                  60

Gln Gln Phe Pro Gly Lys Gly Pro Ala Leu Leu Ile Ala Ile Arg Pro
 65                  70                  75                  80
```

```
Asp Val Ser Glu Lys Lys Glu Gly Arg Phe Thr Ile Ser Phe Asn Lys
                85                  90                  95

Ser Ala Lys Gln Phe Ser Leu His Ile Met Asp Ser Gln Pro Gly Asp
            100                 105                 110

Ser Ala Thr Tyr Phe Cys Ala Ala Ser Thr Gly Asn Phe Asn Lys Phe
        115                 120                 125

Tyr Phe Gly Ser Gly Thr Lys Leu Asn Val Lys Pro Asn Ile Gln Asn
    130                 135                 140

Pro Glu Pro Ala Val Tyr Gln Leu Lys Asp Pro Arg Ser Gln Asp Ser
145                 150                 155                 160

Thr Leu Cys Leu Phe Thr Asp Phe Asp Ser Gln Ile Asn Val Pro Lys
                165                 170                 175

Thr Met Glu Ser Gly Thr Phe Ile Thr Asp Lys Cys Val Leu Asp Met
            180                 185                 190

Lys Ala Met Asp Ser Lys Ser Asn Gly Ala Ile Ala Trp Ser Asn Gln
        195                 200                 205

Thr Ser Phe Thr Cys Gln Asp Ile Phe Lys Glu Thr Asn Ala Thr Tyr
    210                 215                 220

Pro Ser Ser Asp Val Pro Cys Asp Ala Thr Leu Thr Glu Lys Ser Phe
225                 230                 235                 240

Glu Thr Asp Met Asn Leu Asn Phe Gln Asn Leu Leu Val Ile Val Leu
                245                 250                 255

Arg Ile Leu Leu Leu Lys Val Ala Gly Phe Asn Leu Leu Met Thr Leu
            260                 265                 270

Arg Leu Trp Ser Ser
        275

<210> SEQ ID NO 70
<211> LENGTH: 306
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
                20                  25                  30

Glu Met Gly Gln Glu Val Thr Leu Arg Cys Lys Pro Ile Ser Gly His
            35                  40                  45

Asn Ser Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Asn Arg Gln Gly Thr Val Thr Glu Ala Phe Phe Gly Gln Gly Thr
        115                 120                 125

Arg Leu Thr Val Val Glu Asp Leu Arg Asn Val Thr Pro Pro Lys Val
    130                 135                 140

Ser Leu Phe Glu Pro Ser Lys Ala Glu Ile Ala Asn Lys Gln Lys Ala
```

```
            145                 150                 155                 160
Thr Leu Val Cys Leu Ala Arg Gly Phe Phe Pro Asp His Val Glu Leu
                165                 170                 175

Ser Trp Trp Val Asn Gly Lys Glu Val His Ser Gly Val Cys Thr Asp
                180                 185                 190

Pro Gln Ala Tyr Lys Glu Ser Asn Tyr Ser Tyr Cys Leu Ser Ser Arg
                195                 200                 205

Leu Arg Val Ser Ala Thr Phe Trp His Asn Pro Arg Asn His Phe Arg
        210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr Gln Gln Gly Val Leu
                260                 265                 270

Ser Ala Thr Ile Leu Tyr Glu Ile Leu Leu Gly Lys Ala Thr Leu Tyr
                275                 280                 285

Ala Val Leu Val Ser Thr Leu Val Val Met Ala Met Val Lys Arg Lys
        290                 295                 300

Asn Ser
305

<210> SEQ ID NO 71
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

His Ala Gly Leu Ser Asn Arg Leu Ala Arg Asp Asn Glu Leu Arg Glu
1               5                   10                  15

Asn Asp Lys Glu Gln Leu Lys Ala Ile Ser Thr Arg Asp Pro Leu Ser
                20                  25                  30

Glu Ile Thr Glu Gln Glu Lys Asp Phe Leu Trp Ser His Arg His Tyr
            35                  40                  45

Cys Val Thr Ile Pro Glu Ile Leu Pro Lys Leu Leu Leu Ser Val Lys
        50                  55                  60

Trp
65

<210> SEQ ID NO 72
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

His Ala Gly Leu Ser Asn Arg Leu Ala Arg Asp Asn Glu Leu Arg Glu
1               5                   10                  15

Asn Asp Lys Glu Gln Leu Lys Ala Ile Ser Thr Arg Asp Pro Leu Ser
                20                  25                  30

Lys Ile Thr Glu Gln Glu Lys Asp Phe Leu Trp Ser His Arg His Tyr
            35                  40                  45

Cys Val Thr Ile Pro Glu Ile Leu Pro Lys Leu Leu Leu Ser Val Lys
```

```
                    50                  55                  60
Trp
 65

<210> SEQ ID NO 73
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Leu Ser Asn Arg Leu Ala Arg Asp Asn Glu Leu Arg Glu Asn Asp Lys
 1               5                  10                  15

Glu Gln Leu Lys Ala Ile Ser Thr Arg Asp Pro Leu Ser Glu Ile Thr
            20                  25                  30

Glu Gln Glu Lys Asp Phe Leu Trp Ser His Arg His Tyr Cys Val Thr
        35                  40                  45

Ile Pro Glu Ile Leu Pro Lys Leu Leu Leu Ser Val Lys Trp Asn Ser
    50                  55                  60

Arg
 65

<210> SEQ ID NO 74
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Leu Ser Asn Arg Leu Ala Arg Asp Asn Glu Leu Arg Glu Asn Asp Lys
 1               5                  10                  15

Glu Gln Leu Lys Ala Ile Ser Thr Arg Asp Pro Leu Ser Glu Ile Thr
            20                  25                  30

Lys Gln Glu Lys Asp Phe Leu Trp Ser His Arg His Tyr Cys Val Thr
        35                  40                  45

Ile Pro Glu Ile Leu Pro Lys Leu Leu Leu Ser Val Lys Trp Asn Ser
    50                  55                  60

Arg
 65

<210> SEQ ID NO 75
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Lys Thr Leu Ala Leu Asp Lys Thr Glu Gln Glu Ala Leu Glu Tyr Phe
 1               5                  10                  15

Met Lys Gln Met Asn Asp Ala His His Gly Gly Trp Thr Thr Lys Met
            20                  25                  30

Asp Trp Ile Phe His Thr Ile Lys Gln His Ala Leu Asn
        35                  40                  45

<210> SEQ ID NO 76
```

<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Lys Thr Leu Ala Leu Asp Lys Thr Glu Gln Glu Ala Leu Glu Tyr Phe
1               5                   10                  15

Met Lys Gln Met Asn Asp Ala Arg His Gly Gly Trp Thr Thr Lys Met
            20                  25                  30

Asp Trp Ile Phe His Thr Ile Lys Gln His Ala Leu Asn
        35                  40                  45

<210> SEQ ID NO 77
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Lys Thr Leu Ala Leu Asp Lys Thr Glu Gln Glu Ala Leu Glu Tyr Phe
1               5                   10                  15

Met Lys Gln Met Asn Asp Ala Leu His Gly Gly Trp Thr Thr Lys Met
            20                  25                  30

Asp Trp Ile Phe His Thr Ile Lys Gln His Ala Leu Asn
        35                  40                  45

<210> SEQ ID NO 78
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly His Ser Tyr Thr Thr Ala Glu Glu Leu Ala Gly Ile Gly Ile Leu
1               5                   10                  15

Thr Val Ile Leu Gly Val Leu Leu Leu
            20                  25

<210> SEQ ID NO 79
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ile Leu Gly Asp Pro Lys Lys Leu Leu Thr Gln His Phe Val Gln Glu
1               5                   10                  15

Asn Tyr Leu Glu Tyr Arg Gln Val Pro
            20                  25

<210> SEQ ID NO 80
<211> LENGTH: 141
<212> TYPE: PRT
<213> ORGANISM: Homo sapiens

<400> SEQUENCE: 80

```
Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
            35                  40                  45

Val Leu Asp Met Arg Ser Met Asp Phe Lys Ser Asn Ser Ala Val Ala
        50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
                100                 105                 110

Gln Asn Leu Ser Val Ile Gly Phe Arg Ile Leu Leu Lys Val Ala
            115                 120                 125

Gly Phe Asn Leu Leu Met Thr Leu Arg Leu Trp Ser Ser
    130                 135                 140
```

<210> SEQ ID NO 81
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

```
Asn Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Cys
            35                  40                  45

Val Leu Asp Met Lys Ala Met Asp Ser Lys Ser Asn Gly Ala Ile Ala
        50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Leu
                100                 105                 110

Val Ile Val Leu Arg Ile Leu Leu Leu Lys Val Ala Gly Phe Asn Leu
            115                 120                 125

Leu Met Thr Leu Arg Leu Trp Ser Ser
    130                 135
```

<210> SEQ ID NO 82
<211> LENGTH: 177
<212> TYPE: PRT
<213> ORGANISM: Homo sapiens

<400> SEQUENCE: 82

```
Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30
```

Ala Thr Gly Phe Phe Pro Asp His Val Glu Leu Ser Trp Trp Val Asn
            35                  40                  45

Gly Lys Glu Val His Ser Gly Val Ser Thr Asp Pro Gln Pro Leu Lys
 50                  55                  60

Glu Gln Pro Ala Leu Asn Asp Ser Arg Tyr Cys Leu Ser Ser Arg Leu
 65                  70                  75                  80

Arg Val Ser Ala Thr Phe Trp Gln Asn Pro Arg Asn His Phe Arg Cys
                 85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
                115                 120                 125

Ala Asp Cys Gly Phe Thr Ser Val Ser Tyr Gln Gln Gly Val Leu Ser
130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 83
<211> LENGTH: 173
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Glu Asp Leu Arg Asn Val Thr Pro Pro Lys Val Ser Leu Phe Glu Pro
 1               5                  10                  15

Ser Lys Ala Glu Ile Ala Asn Lys Gln Lys Ala Thr Leu Val Cys Leu
                20                  25                  30

Ala Arg Gly Phe Phe Pro Asp His Val Glu Leu Ser Trp Trp Val Asn
            35                  40                  45

Gly Lys Glu Val His Ser Gly Val Cys Thr Asp Pro Gln Ala Tyr Lys
 50                  55                  60

Glu Ser Asn Tyr Ser Tyr Cys Leu Ser Ser Arg Leu Arg Val Ser Ala
 65                  70                  75                  80

Thr Phe Trp His Asn Pro Arg Asn His Phe Arg Cys Gln Val Gln Phe
                 85                  90                  95

His Gly Leu Ser Glu Glu Asp Lys Trp Pro Glu Gly Ser Pro Lys Pro
                100                 105                 110

Val Thr Gln Asn Ile Ser Ala Glu Ala Trp Gly Arg Ala Asp Cys Gly
                115                 120                 125

Ile Thr Ser Ala Ser Tyr Gln Gln Gly Val Leu Ser Ala Thr Ile Leu
                130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170

<210> SEQ ID NO 84
<211> LENGTH: 27
<212> TYPE: PRT
<213> ORGANISM: Unknown

```
<220> FEATURE:
<223> OTHER INFORMATION: Description of Unknown:
      Furin-2A-peptide sequence

<400> SEQUENCE: 84

Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro
            20                  25

<210> SEQ ID NO 85
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ser Gly Ser Gly
1

<210> SEQ ID NO 86
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Cys Ala Val Arg Pro Leu Tyr Gly Gly Ser Tyr Ile Pro Thr Phe
1               5                   10                  15

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Cys Ala Val Asn Phe Gly Gly Gly Lys Leu Ile Phe
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Cys Val Leu Gly Gly Gly Ser Ala Arg Gln Leu Thr Phe
1               5                   10

<210> SEQ ID NO 89
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89
```

```
Cys Ala Val Asn Lys Arg Ser Asn Tyr Gln Leu Ile Trp
1               5                   10
```

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

```
Cys Val Val Asn Asp Gly Thr Tyr Lys Tyr Ile Phe
1               5                   10
```

<210> SEQ ID NO 91
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

```
Cys Ala Ala Ser Met Ile Ala Arg Leu Met Phe
1               5                   10
```

<210> SEQ ID NO 92
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

```
Cys Ala Met Arg Asp Phe Ser Gly Gly Tyr Asn Lys Leu Ile Phe
1               5                   10                  15
```

<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

```
Cys Ala Gly His Pro Leu Asn Asp Met Arg Phe
1               5                   10
```

<210> SEQ ID NO 94
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

```
Cys Ala Phe Val Arg Asn Asn Asn Ala Arg Leu Met Phe
1               5                   10
```

<210> SEQ ID NO 95
<211> LENGTH: 15
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 95

Cys Ala Glu Ser Leu Met Asp Thr Gly Arg Arg Ala Leu Thr Phe
1               5                   10                  15

<210> SEQ ID NO 96
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Cys Ala Ser Ser Tyr Val Gly Asn Thr Gly Glu Leu Phe Phe
1               5                   10

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Cys Ala Ser Ser Leu Ser Phe Gly Thr Glu Ala Phe Phe
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Cys Ala Ser Ser Arg Met Asn Thr Glu Ala Phe Phe
1               5                   10

<210> SEQ ID NO 99
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Cys Ala Ser Ser Tyr Phe Gln Gly Ala Ala Glu Ala Phe Phe
1               5                   10

<210> SEQ ID NO 100
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Cys Ala Ser Ser Pro Lys Gln Gln Tyr Glu Gln Tyr Phe
1               5                   10
```

```
<210> SEQ ID NO 101
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Cys Ala Ser Ser Phe Thr Thr Gly Val Gly Thr Glu Ala Phe Phe
1               5                   10                  15

<210> SEQ ID NO 102
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Cys Ala Ser Arg Lys Gln Asn Tyr Gly Tyr Thr Phe
1               5                   10

<210> SEQ ID NO 103
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Cys Ala Ser Ser Glu Asn Gly Gly Val Asp Glu Gln Phe Phe
1               5                   10

<210> SEQ ID NO 104
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Cys Ala Ser Ser Ser Ala Phe Thr Gly Thr Glu Asp Pro Gly Tyr Thr
1               5                   10                  15

Phe

<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Cys Ala Ser Ser Glu Trp Thr Ser Gly Asp Asn Glu Gln Phe Phe
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 106

Cys Ala Ser Ser Leu Gly Thr Phe Ser Thr Asp Thr Gln Tyr Phe
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Cys Ala Ser Ser Gln Gly Gly Arg Gly Glu Tyr Glu Ala Phe Phe
1               5                   10                  15

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Cys Ala Ser Ser Pro Gly Tyr Glu Gln Phe Phe
1               5                   10

<210> SEQ ID NO 109
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Cys Ala Ser Ser His Pro Leu Gly Gly Gln Gly Asn Thr Trp Gly Asn
1               5                   10                  15

Glu Gln Phe Phe
            20

<210> SEQ ID NO 110
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Cys Ala Ser Ser Phe Ser Gly Thr Gly Ala Phe Phe
1               5                   10

<210> SEQ ID NO 111
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Cys Ala Ser Ser Pro Thr Gly Thr Ser Gly Asn Glu Gln Tyr Phe
1               5                   10                  15
```

```
<210> SEQ ID NO 112
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Cys Ala Ser Ser Glu Gly His Leu Asn Thr Glu Ala Phe Phe
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Cys Ala Ser Ser Arg Val Gln Asn Glu Gln Phe Phe
1               5                   10

<210> SEQ ID NO 114
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Cys Ala Ser Ser Phe Ser Gly Thr Pro Pro Gln Pro Gln His Phe
1               5                   10                  15

<210> SEQ ID NO 115
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Cys Ala Ser Ser Leu Gln Gly Tyr Asn Glu Gln Phe Phe
1               5                   10

<210> SEQ ID NO 116
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Cys Ala Ser Ser Ile Pro Gly Lys Glu Thr Gln Tyr Phe
1               5                   10

<210> SEQ ID NO 117
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 117

Cys Ala Ser Ser Thr Thr Leu Thr Gly Ile Lys Asp Thr Phe
1               5                   10

<210> SEQ ID NO 118
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Cys Ala Ser Ser Tyr Gly Leu Thr Tyr Glu Gln Tyr Phe
1               5                   10

<210> SEQ ID NO 119
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Cys Ala Ser Ser Ser Leu Gly Asp Val Met Asn Thr Glu Ala Phe Phe
1               5                   10                  15

<210> SEQ ID NO 120
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Cys Ala Ser Ser Arg Gly Leu Gln Pro Thr Gln Tyr Phe
1               5                   10

<210> SEQ ID NO 121
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Cys Ala Ser Ser Phe Asn Pro Ser Tyr Glu Gln Tyr Phe
1               5                   10

<210> SEQ ID NO 122
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Cys Ala Ser Ser Leu Ser Gly Gly Gly Asp Tyr Gly Tyr Thr Phe
1               5                   10                  15

<210> SEQ ID NO 123
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 123

Cys Ala Ser Gly Gly Ser Gly Asn Thr Gly Lys Leu Ile Phe
1               5                   10

<210> SEQ ID NO 124
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Cys Ala Ser Ser Leu Gly Gln Phe Asn Tyr Glu Gln Tyr Phe
1               5                   10

<210> SEQ ID NO 125
<211> LENGTH: 606
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Met Asp Thr Arg Val Leu Cys Cys Ala Val Ile Cys Leu Leu Gly Ala
1               5                   10                  15

Gly Leu Ser Asn Ala Gly Val Met Gln Asn Pro Arg His Leu Val Arg
            20                  25                  30

Arg Arg Gly Gln Glu Ala Arg Leu Arg Cys Ser Pro Met Lys Gly His
        35                  40                  45

Ser His Val Tyr Trp Tyr Arg Gln Leu Pro Glu Glu Gly Leu Lys Phe
    50                  55                  60

Met Val Tyr Leu Gln Lys Glu Asn Ile Ile Asp Glu Ser Gly Met Pro
65                  70                  75                  80

Lys Glu Arg Phe Ser Ala Glu Phe Pro Lys Glu Gly Pro Ser Ile Leu
                85                  90                  95

Arg Ile Gln Gln Val Val Arg Gly Asp Ser Ala Ala Tyr Phe Cys Ala
            100                 105                 110

Ser Ser Pro Val Asn Leu Ala Gly Val Ser Arg Ala Asp Thr Gln Tyr
        115                 120                 125

Phe Gly Pro Gly Thr Arg Leu Thr Val Leu Glu Asp Leu Arg Asn Val
    130                 135                 140

Thr Pro Pro Lys Val Ser Leu Phe Glu Pro Ser Lys Ala Glu Ile Ala
145                 150                 155                 160

Asn Lys Gln Lys Ala Thr Leu Val Cys Leu Ala Arg Gly Phe Phe Pro
                165                 170                 175

Asp His Val Glu Leu Ser Trp Trp Val Asn Gly Lys Glu Val His Ser
            180                 185                 190

Gly Val Cys Thr Asp Pro Gln Ala Tyr Lys Glu Ser Asn Tyr Ser Tyr
        195                 200                 205

Cys Leu Ser Ser Arg Leu Arg Val Ser Ala Thr Phe Trp His Asn Pro
    210                 215                 220

Arg Asn His Phe Arg Cys Gln Val Gln Phe His Gly Leu Ser Glu Glu
225                 230                 235                 240
```

Asp Lys Trp Pro Glu Gly Ser Pro Lys Pro Val Thr Gln Asn Ile Ser
                245                 250                 255

Ala Glu Ala Trp Gly Arg Ala Asp Cys Gly Ile Thr Ser Ala Ser Tyr
            260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Thr Leu Val Met Ala
290                 295                 300

Met Val Lys Arg Lys Asn Ser Arg Ala Lys Arg Ser Gly Ser Gly Ala
305                 310                 315                 320

Thr Asn Phe Ser Leu Leu Lys Gln Ala Gly Asp Val Glu Glu Asn Pro
                325                 330                 335

Gly Pro Met Glu Thr Leu Leu Gly Leu Leu Ile Leu Trp Leu Gln Leu
            340                 345                 350

Gln Trp Val Ser Ser Lys Gln Glu Val Thr Gln Ile Pro Ala Ala Leu
        355                 360                 365

Ser Val Pro Glu Gly Glu Asn Leu Val Leu Asn Cys Ser Phe Thr Asp
    370                 375                 380

Ser Ala Ile Tyr Asn Leu Gln Trp Phe Arg Gln Asp Pro Gly Lys Gly
385                 390                 395                 400

Leu Thr Ser Leu Leu Leu Ile Gln Ser Ser Gln Arg Glu Gln Thr Ser
                405                 410                 415

Gly Arg Leu Asn Ala Ser Leu Asp Lys Ser Ser Gly Arg Ser Thr Leu
            420                 425                 430

Tyr Ile Ala Ala Ser Gln Pro Gly Asp Ser Ala Thr Tyr Leu Cys Ala
        435                 440                 445

Val Lys Gly Ser Asp Asp Tyr Lys Leu Ser Phe Gly Ala Gly Thr Thr
    450                 455                 460

Val Thr Val Arg Ala Asn Ile Gln Asn Pro Glu Pro Ala Val Tyr Gln
465                 470                 475                 480

Leu Lys Asp Pro Arg Ser Gln Asp Ser Thr Leu Cys Leu Phe Thr Asp
                485                 490                 495

Phe Asp Ser Gln Ile Asn Val Pro Lys Thr Met Glu Ser Gly Thr Phe
            500                 505                 510

Ile Thr Asp Lys Cys Val Leu Asp Met Lys Ala Met Asp Ser Lys Ser
        515                 520                 525

Asn Gly Ala Ile Ala Trp Ser Asn Gln Thr Ser Phe Thr Cys Gln Asp
    530                 535                 540

Ile Phe Lys Glu Thr Asn Ala Thr Tyr Pro Ser Ser Asp Val Pro Cys
545                 550                 555                 560

Asp Ala Thr Leu Thr Glu Lys Ser Phe Glu Thr Asp Met Asn Leu Asn
                565                 570                 575

Phe Gln Asn Leu Leu Val Ile Val Leu Arg Ile Leu Leu Leu Lys Val
            580                 585                 590

Ala Gly Phe Asn Leu Leu Met Thr Leu Arg Leu Trp Ser Ser
        595                 600                 605

<210> SEQ ID NO 126
<211> LENGTH: 598
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

```
Met Gly Thr Arg Leu Leu Phe Trp Val Ala Phe Cys Leu Leu Gly Ala
1               5                   10                  15

Tyr His Thr Gly Ala Gly Val Ser Gln Ser Pro Ser Asn Lys Val Thr
            20                  25                  30

Glu Lys Gly Lys Asp Val Glu Leu Arg Cys Asp Pro Ile Ser Gly His
        35                  40                  45

Thr Ala Leu Tyr Trp Tyr Arg Gln Arg Leu Gly Gln Gly Leu Glu Phe
    50                  55                  60

Leu Ile Tyr Phe Gln Gly Asn Ser Ala Pro Asp Lys Ser Gly Leu Pro
65                  70                  75                  80

Ser Asp Arg Phe Ser Ala Glu Arg Thr Gly Glu Ser Val Ser Thr Leu
                85                  90                  95

Thr Ile Gln Arg Thr Gln Gln Glu Asp Ser Ala Val Tyr Leu Cys Ala
            100                 105                 110

Ser Ser Pro Arg Gly Tyr Gln Pro Gln His Phe Gly Asp Gly Thr Arg
        115                 120                 125

Leu Ser Ile Leu Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Cys Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Thr Leu Val Val Met Ala Met Val Lys Arg Lys Asn
    290                 295                 300

Ser Arg Ala Lys Arg Ser Gly Ser Gly Ala Thr Asn Phe Ser Leu Leu
305                 310                 315                 320

Lys Gln Ala Gly Asp Val Glu Glu Asn Pro Gly Pro Met Trp Gly Val
                325                 330                 335

Phe Leu Leu Tyr Val Ser Met Lys Met Gly Gly Thr Thr Gly Gln Asn
            340                 345                 350

Ile Asp Gln Pro Thr Glu Met Thr Ala Thr Glu Gly Ala Ile Val Gln
        355                 360                 365

Ile Asn Cys Thr Tyr Gln Thr Ser Gly Phe Asn Gly Leu Phe Trp Tyr
    370                 375                 380

Gln Gln His Ala Gly Glu Ala Pro Thr Phe Leu Ser Tyr Asn Val Leu
385                 390                 395                 400

Asp Gly Leu Glu Glu Lys Gly Arg Phe Ser Ser Phe Leu Ser Arg Ser
                405                 410                 415
```

```
Lys Gly Tyr Ser Tyr Leu Leu Lys Glu Leu Gln Met Lys Asp Ser
            420                 425                 430

Ala Ser Tyr Leu Cys Ala Val Thr Ser Trp Gly Lys Leu Gln Phe Lys
        435                 440                 445

Leu Gln Phe Gly Ala Gly Thr Gln Val Val Thr Pro Asn Ile Gln
    450                 455                 460

Asn Pro Glu Pro Ala Val Tyr Gln Leu Lys Asp Pro Arg Ser Gln Asp
465                 470                 475                 480

Ser Thr Leu Cys Leu Phe Thr Asp Phe Asp Ser Gln Ile Asn Val Pro
            485                 490                 495

Lys Thr Met Glu Ser Gly Thr Phe Ile Thr Asp Lys Cys Val Leu Asp
            500                 505                 510

Met Lys Ala Met Asp Ser Lys Ser Asn Gly Ala Ile Ala Trp Ser Asn
            515                 520                 525

Gln Thr Ser Phe Thr Cys Gln Asp Ile Phe Lys Glu Thr Asn Ala Thr
    530                 535                 540

Tyr Pro Ser Ser Asp Val Pro Cys Asp Ala Thr Leu Thr Glu Lys Ser
545                 550                 555                 560

Phe Glu Thr Asp Met Asn Leu Asn Phe Gln Asn Leu Leu Val Ile Val
            565                 570                 575

Leu Arg Ile Leu Leu Leu Lys Val Ala Gly Phe Asn Leu Leu Met Thr
            580                 585                 590

Leu Arg Leu Trp Ser Ser
            595

<210> SEQ ID NO 127
<211> LENGTH: 608
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Met Asp Thr Arg Val Leu Cys Cys Ala Val Ile Cys Leu Leu Gly Ala
1               5                   10                  15

Gly Leu Ser Asn Ala Gly Val Met Gln Asn Pro Arg His Leu Val Arg
            20                  25                  30

Arg Arg Gly Gln Glu Ala Arg Leu Arg Cys Ser Pro Met Lys Gly His
        35                  40                  45

Ser His Val Tyr Trp Tyr Arg Gln Leu Pro Glu Glu Gly Leu Lys Phe
    50                  55                  60

Met Val Tyr Leu Gln Lys Glu Asn Ile Ile Asp Glu Ser Gly Met Pro
65              70                  75                  80

Lys Glu Arg Phe Ser Ala Glu Phe Pro Lys Glu Gly Pro Ser Ile Leu
                85                  90                  95

Arg Ile Gln Gln Val Val Arg Gly Asp Ser Ala Ala Tyr Phe Cys Ala
            100                 105                 110

Ser Ser Pro Pro Glu Ala Gly Leu Asp Thr Glu Ala Phe Phe Gly Gln
        115                 120                 125

Gly Thr Arg Leu Thr Val Val Glu Asp Leu Arg Asn Val Thr Pro Pro
    130                 135                 140

Lys Val Ser Leu Phe Glu Pro Ser Lys Ala Glu Ile Ala Asn Lys Gln
145                 150                 155                 160

Lys Ala Thr Leu Val Cys Leu Ala Arg Gly Phe Phe Pro Asp His Val
```

```
                165                 170                 175
Glu Leu Ser Trp Trp Val Asn Gly Lys Glu Val His Ser Gly Val Cys
            180                 185                 190

Thr Asp Pro Gln Ala Tyr Lys Glu Ser Asn Tyr Ser Tyr Cys Leu Ser
            195                 200                 205

Ser Arg Leu Arg Val Ser Ala Thr Phe Trp His Asn Pro Arg Asn His
            210                 215                 220

Phe Arg Cys Gln Val Gln Phe His Gly Leu Ser Glu Glu Asp Lys Trp
225                 230                 235                 240

Pro Glu Gly Ser Pro Lys Pro Val Thr Gln Asn Ile Ser Ala Glu Ala
                245                 250                 255

Trp Gly Arg Ala Asp Cys Gly Ile Thr Ser Ala Ser Tyr Gln Gln Gly
                260                 265                 270

Val Leu Ser Ala Thr Ile Leu Tyr Glu Ile Leu Leu Gly Lys Ala Thr
            275                 280                 285

Leu Tyr Ala Val Leu Val Ser Thr Leu Val Val Met Ala Met Val Lys
            290                 295                 300

Arg Lys Asn Ser Arg Ala Lys Arg Ser Gly Ser Gly Ala Thr Asn Phe
305                 310                 315                 320

Ser Leu Leu Lys Gln Ala Gly Asp Val Glu Glu Asn Pro Gly Pro Met
                325                 330                 335

Ser Leu Ser Leu Leu Lys Val Val Thr Ala Ser Leu Trp Leu Gly
                340                 345                 350

Pro Gly Ile Ala Gln Lys Ile Thr Gln Thr Gln Pro Gly Met Phe Val
            355                 360                 365

Gln Glu Lys Glu Ala Val Thr Leu Asp Cys Thr Tyr Asp Thr Ser Asp
370                 375                 380

Gln Ser Tyr Gly Leu Phe Trp Tyr Lys Gln Pro Ser Ser Gly Glu Met
385                 390                 395                 400

Ile Phe Leu Ile Tyr Gln Gly Ser Tyr Asp Glu Gln Asn Ala Thr Glu
            405                 410                 415

Gly Arg Tyr Ser Leu Asn Phe Gln Lys Ala Arg Lys Ser Ala Asn Leu
            420                 425                 430

Val Ile Ser Ala Ser Gln Leu Gly Asp Ser Ala Met Tyr Phe Cys Ala
            435                 440                 445

Met Arg Glu Val Leu Asp Asn Thr Asp Lys Leu Ile Phe Gly Thr Gly
450                 455                 460

Thr Arg Leu Gln Val Phe Pro Asn Ile Gln Asn Pro Glu Pro Ala Val
465                 470                 475                 480

Tyr Gln Leu Lys Asp Pro Arg Ser Gln Asp Ser Thr Leu Cys Leu Phe
            485                 490                 495

Thr Asp Phe Asp Ser Gln Ile Asn Val Pro Lys Thr Met Glu Ser Gly
            500                 505                 510

Thr Phe Ile Thr Asp Lys Cys Val Leu Asp Met Lys Ala Met Asp Ser
            515                 520                 525

Lys Ser Asn Gly Ala Ile Ala Trp Ser Asn Gln Thr Ser Phe Thr Cys
            530                 535                 540

Gln Asp Ile Phe Lys Glu Thr Asn Ala Thr Tyr Pro Ser Ser Asp Val
545                 550                 555                 560

Pro Cys Asp Ala Thr Leu Thr Glu Lys Ser Phe Glu Thr Asp Met Asn
                565                 570                 575

Leu Asn Phe Gln Asn Leu Leu Val Ile Val Leu Arg Ile Leu Leu Leu
            580                 585                 590
```

```
Lys Val Ala Gly Phe Asn Leu Leu Met Thr Leu Arg Leu Trp Ser Ser
        595                 600                 605

<210> SEQ ID NO 128
<211> LENGTH: 604
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Met Leu Leu Leu Leu Leu Leu Gly Pro Ala Gly Ser Gly Leu Gly
1               5                   10                  15

Ala Val Val Ser Gln His Pro Ser Arg Val Ile Cys Lys Ser Gly Thr
            20                  25                  30

Ser Val Lys Ile Glu Cys Arg Ser Leu Asp Phe Gln Ala Thr Thr Met
        35                  40                  45

Phe Trp Tyr Arg Gln Phe Pro Lys Gln Ser Leu Met Leu Met Ala Thr
    50                  55                  60

Ser Asn Glu Gly Ser Lys Ala Thr Tyr Glu Gln Gly Val Glu Lys Asp
65                  70                  75                  80

Lys Phe Leu Ile Asn His Ala Ser Leu Thr Leu Ser Thr Leu Thr Val
                85                  90                  95

Thr Ser Ala His Pro Glu Asp Ser Ser Phe Tyr Ile Cys Ser Ala Cys
            100                 105                 110

Ser Ala Arg Glu Gln Gly Pro Leu Glu Glu Gln Tyr Phe Gly Pro Gly
        115                 120                 125

Thr Arg Leu Thr Val Thr Glu Asp Leu Arg Asn Val Thr Pro Pro Lys
    130                 135                 140

Val Ser Leu Phe Glu Pro Ser Lys Ala Glu Ile Ala Asn Lys Gln Lys
145                 150                 155                 160

Ala Thr Leu Val Cys Leu Ala Arg Gly Phe Phe Pro Asp His Val Glu
                165                 170                 175

Leu Ser Trp Trp Val Asn Gly Lys Glu Val His Ser Gly Val Cys Thr
            180                 185                 190

Asp Pro Gln Ala Tyr Lys Glu Ser Asn Tyr Ser Tyr Cys Leu Ser Ser
        195                 200                 205

Arg Leu Arg Val Ser Ala Thr Phe Trp His Asn Pro Arg Asn His Phe
    210                 215                 220

Arg Cys Gln Val Gln Phe His Gly Leu Ser Glu Glu Asp Lys Trp Pro
225                 230                 235                 240

Glu Gly Ser Pro Lys Pro Val Thr Gln Asn Ile Ser Ala Glu Ala Trp
                245                 250                 255

Gly Arg Ala Asp Cys Gly Ile Thr Ser Ala Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Thr Leu Val Val Met Ala Met Val Lys Arg
    290                 295                 300

Lys Asn Ser Arg Ala Lys Arg Ser Gly Ser Gly Ala Thr Asn Phe Ser
305                 310                 315                 320

Leu Leu Lys Gln Ala Gly Asp Val Glu Glu Asn Pro Gly Pro Met Met
                325                 330                 335

Lys Ser Leu Arg Val Leu Leu Val Ile Leu Trp Leu Gln Leu Ser Trp
```

```
                340                 345                 350
Val Trp Ser Gln Gln Lys Glu Val Gln Asp Pro Gly Pro Leu Ser
            355                 360                 365
Val Pro Glu Gly Ala Ile Val Ser Leu Asn Cys Thr Tyr Ser Asn Ser
370                 375                 380
Ala Phe Gln Tyr Phe Met Trp Tyr Arg Gln Tyr Ser Arg Lys Gly Pro
385                 390                 395                 400
Glu Leu Leu Met Tyr Thr Tyr Ser Ser Gly Asn Lys Glu Asp Gly Arg
                405                 410                 415
Phe Thr Ala Gln Val Asp Lys Ser Ser Lys Tyr Ile Ser Leu Phe Ile
            420                 425                 430
Arg Asp Ser Gln Pro Ser Asp Ser Ala Thr Tyr Leu Cys Ala Met Asn
            435                 440                 445
Ser Gly Gly Tyr Gln Lys Val Thr Phe Gly Ile Gly Thr Lys Leu Gln
            450                 455                 460
Val Ile Pro Asn Ile Gln Asn Pro Glu Pro Ala Val Tyr Gln Leu Lys
465                 470                 475                 480
Asp Pro Arg Ser Gln Asp Ser Thr Leu Cys Leu Phe Thr Asp Phe Asp
                485                 490                 495
Ser Gln Ile Asn Val Pro Lys Thr Met Glu Ser Gly Thr Phe Ile Thr
                500                 505                 510
Asp Lys Cys Val Leu Asp Met Lys Ala Met Asp Ser Lys Ser Asn Gly
            515                 520                 525
Ala Ile Ala Trp Ser Asn Gln Thr Ser Phe Thr Cys Gln Asp Ile Phe
            530                 535                 540
Lys Glu Thr Asn Ala Thr Tyr Pro Ser Ser Asp Val Pro Cys Asp Ala
545                 550                 555                 560
Thr Leu Thr Glu Lys Ser Phe Glu Thr Asp Met Asn Leu Asn Phe Gln
                565                 570                 575
Asn Leu Leu Val Ile Val Leu Arg Ile Leu Leu Leu Lys Val Ala Gly
            580                 585                 590
Phe Asn Leu Leu Met Thr Leu Arg Leu Trp Ser Ser
            595                 600

<210> SEQ ID NO 129
<211> LENGTH: 597
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Met Gly Pro Gly Leu Leu Cys Trp Ala Leu Leu Cys Leu Leu Gly Ala
1               5                   10                  15
Gly Leu Val Asp Ala Gly Val Thr Gln Ser Pro Thr His Leu Ile Lys
            20                  25                  30
Thr Arg Gly Gln Gln Val Thr Leu Arg Cys Ser Pro Lys Ser Gly His
            35                  40                  45
Asp Thr Val Ser Trp Tyr Gln Gln Ala Leu Gly Gln Gly Pro Gln Phe
            50                  55                  60
Ile Phe Gln Tyr Tyr Glu Glu Glu Arg Gln Arg Gly Asn Phe Pro
65                  70                  75                  80
Asp Arg Phe Ser Gly His Gln Phe Pro Asn Tyr Ser Ser Glu Leu Asn
                85                  90                  95
```

```
Val Asn Ala Leu Leu Leu Gly Asp Ser Ala Leu Tyr Leu Cys Ala Ser
            100                 105                 110

Ser Phe Gly Thr Ala Thr Tyr Glu Gln Tyr Phe Gly Pro Gly Thr Arg
        115                 120                 125

Leu Thr Val Thr Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
            165                 170                 175

Trp Trp Val Asn Gly Lys Glu Val His Ser Gly Val Cys Thr Asp Pro
            180                 185                 190

Gln Ala Tyr Lys Glu Ser Asn Tyr Ser Tyr Cys Leu Ser Ser Arg Leu
            195                 200                 205

Arg Val Ser Ala Thr Phe Trp His Asn Pro Arg Asn His Phe Arg Cys
            210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
            245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
            275                 280                 285

Val Leu Val Ser Thr Leu Val Val Met Ala Met Val Lys Arg Lys Asn
            290                 295                 300

Ser Arg Ala Lys Arg Ser Gly Ser Gly Ala Thr Asn Phe Ser Leu Leu
305                 310                 315                 320

Lys Gln Ala Gly Asp Val Glu Glu Asn Pro Gly Pro Met Arg Leu Val
            325                 330                 335

Ala Arg Val Thr Val Phe Leu Thr Phe Gly Thr Ile Ile Asp Ala Lys
            340                 345                 350

Thr Thr Gln Pro Pro Ser Met Asp Cys Ala Glu Gly Arg Ala Ala Asn
            355                 360                 365

Leu Pro Cys Asn His Ser Thr Ile Ser Gly Asn Glu Tyr Val Tyr Trp
    370                 375                 380

Tyr Arg Gln Ile His Ser Gln Gly Pro Gln Tyr Ile Ile His Gly Leu
385                 390                 395                 400

Lys Asn Asn Glu Thr Asn Glu Met Ala Ser Leu Ile Ile Thr Glu Asp
            405                 410                 415

Arg Lys Ser Ser Thr Leu Ile Leu Pro His Ala Thr Leu Arg Asp Thr
            420                 425                 430

Ala Val Tyr Tyr Cys Ile Val Arg Val Ala Gly Ser Ala Arg Gln Leu
            435                 440                 445

Thr Phe Gly Ser Gly Thr Gln Leu Thr Val Leu Pro Asn Ile Gln Asn
            450                 455                 460

Pro Glu Pro Ala Val Tyr Gln Leu Lys Asp Pro Arg Ser Gln Asp Ser
465                 470                 475                 480

Thr Leu Cys Leu Phe Thr Asp Phe Asp Ser Gln Ile Asn Val Pro Lys
            485                 490                 495

Thr Met Glu Ser Gly Thr Phe Ile Thr Asp Lys Cys Val Leu Asp Met
            500                 505                 510

Lys Ala Met Asp Ser Lys Ser Asn Gly Ala Ile Ala Trp Ser Asn Gln
```

```
            515                 520                 525

Thr Ser Phe Thr Cys Gln Asp Ile Phe Lys Glu Thr Asn Ala Thr Tyr
    530                 535                 540

Pro Ser Ser Asp Val Pro Cys Asp Ala Thr Leu Thr Glu Lys Ser Phe
545                 550                 555                 560

Glu Thr Asp Met Asn Leu Asn Phe Gln Asn Leu Leu Val Ile Val Leu
                565                 570                 575

Arg Ile Leu Leu Leu Lys Val Ala Gly Phe Asn Leu Leu Met Thr Leu
                580                 585                 590

Arg Leu Trp Ser Ser
                595

<210> SEQ ID NO 130
<211> LENGTH: 602
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
                20                  25                  30

Val Thr Gly Lys Lys Leu Thr Val Thr Cys Ser Gln Asn Met Asn His
            35                  40                  45

Glu Tyr Met Ser Trp Tyr Arg Gln Asp Pro Gly Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
                100                 105                 110

Ser Pro Tyr Arg Gln Gly Ser Tyr Gly Tyr Thr Phe Gly Ser Gly Thr
                115                 120                 125

Arg Leu Thr Val Val Glu Asp Leu Arg Asn Val Thr Pro Pro Lys Val
                130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Cys Thr Asp
                180                 185                 190

Pro Gln Ala Tyr Lys Glu Ser Asn Tyr Ser Tyr Cys Leu Ser Ser Arg
                195                 200                 205

Leu Arg Val Ser Ala Thr Phe Trp His Asn Pro Arg Asn His Phe Arg
                210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr Gln Gln Gly Val Leu
                260                 265                 270
```

```
Ser Ala Thr Ile Leu Tyr Glu Ile Leu Leu Gly Lys Ala Thr Leu Tyr
            275                 280                 285

Ala Val Leu Val Ser Thr Leu Val Val Met Ala Met Val Lys Arg Lys
        290                 295                 300

Asn Ser Arg Ala Lys Arg Ser Gly Ser Gly Ala Thr Asn Phe Ser Leu
305                 310                 315                 320

Leu Lys Gln Ala Gly Asp Val Glu Glu Asn Pro Gly Pro Met Thr Ser
                325                 330                 335

Ile Arg Ala Val Phe Ile Phe Leu Trp Leu Gln Leu Asp Leu Val Asn
                340                 345                 350

Gly Glu Asn Val Glu Gln His Pro Ser Thr Leu Ser Val Gln Glu Gly
            355                 360                 365

Asp Ser Ala Val Ile Lys Cys Thr Tyr Ser Asp Ser Ala Ser Asn Tyr
        370                 375                 380

Phe Pro Trp Tyr Lys Gln Glu Leu Gly Lys Gly Pro Gln Leu Ile Ile
385                 390                 395                 400

Asp Ile Arg Ser Asn Val Gly Glu Lys Lys Asp Gln Arg Ile Ala Val
                405                 410                 415

Thr Leu Asn Lys Thr Ala Lys His Phe Ser Leu His Ile Thr Glu Thr
                420                 425                 430

Gln Pro Glu Asp Ser Ala Val Tyr Phe Cys Ala Ala Ser Ile Pro Gly
            435                 440                 445

Thr Ala Ser Lys Leu Thr Phe Gly Thr Gly Thr Arg Leu Gln Val Thr
        450                 455                 460

Leu Asn Ile Gln Asn Pro Glu Pro Ala Val Tyr Gln Leu Lys Asp Pro
465                 470                 475                 480

Arg Ser Gln Asp Ser Thr Leu Cys Leu Phe Thr Asp Phe Asp Ser Gln
                485                 490                 495

Ile Asn Val Pro Lys Thr Met Glu Ser Gly Thr Phe Ile Thr Asp Lys
                500                 505                 510

Cys Val Leu Asp Met Lys Ala Met Asp Ser Lys Ser Asn Gly Ala Ile
            515                 520                 525

Ala Trp Ser Asn Gln Thr Ser Phe Thr Cys Gln Asp Ile Phe Lys Glu
        530                 535                 540

Thr Asn Ala Thr Tyr Pro Ser Ser Asp Val Pro Cys Asp Ala Thr Leu
545                 550                 555                 560

Thr Glu Lys Ser Phe Glu Thr Asp Met Asn Leu Asn Phe Gln Asn Leu
                565                 570                 575

Leu Val Ile Val Leu Arg Ile Leu Leu Leu Lys Val Ala Gly Phe Asn
                580                 585                 590

Leu Leu Met Thr Leu Arg Leu Trp Ser Ser
            595                 600

<210> SEQ ID NO 131
<211> LENGTH: 610
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30
```

-continued

Glu Met Gly Gln Glu Val Thr Leu Arg Cys Lys Pro Ile Ser Gly His
         35                  40                  45

Asn Ser Leu Phe Trp Tyr Arg Gln Thr Met Met Arg Gly Leu Glu Leu
 50                      55                  60

Leu Ile Tyr Phe Asn Asn Asn Val Pro Ile Asp Asp Ser Gly Met Pro
 65                  70                  75                  80

Glu Asp Arg Phe Ser Ala Lys Met Pro Asn Ala Ser Phe Ser Thr Leu
                     85                  90                  95

Lys Ile Gln Pro Ser Glu Pro Arg Asp Ser Ala Val Tyr Phe Cys Ala
                100                 105                 110

Ser Asn Arg Gln Gly Thr Val Thr Glu Ala Phe Phe Gly Gln Gly Thr
            115                 120                 125

Arg Leu Thr Val Val Glu Asp Leu Arg Asn Val Thr Pro Pro Lys Val
    130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Cys Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
    210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr Gln Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Thr Leu Val Val Met Ala Met Val Lys Arg Lys
    290                 295                 300

Asn Ser Arg Ala Lys Arg Ser Gly Ser Gly Ala Thr Asn Phe Ser Leu
305                 310                 315                 320

Leu Lys Gln Ala Gly Asp Val Glu Glu Asn Pro Gly Pro Met Asp Lys
                325                 330                 335

Ile Leu Gly Ala Ser Phe Leu Val Leu Trp Leu Gln Leu Cys Trp Val
            340                 345                 350

Ser Gly Gln Gln Lys Glu Lys Ser Asp Gln Gln Val Lys Gln Ser
        355                 360                 365

Pro Gln Ser Leu Ile Val Gln Lys Gly Gly Ile Ser Ile Ile Asn Cys
    370                 375                 380

Ala Tyr Glu Asn Thr Ala Phe Asp Tyr Phe Pro Trp Tyr Gln Gln Phe
385                 390                 395                 400

Pro Gly Lys Gly Pro Ala Leu Leu Ile Ala Ile Arg Pro Asp Val Ser
                405                 410                 415

Glu Lys Lys Glu Gly Arg Phe Thr Ile Ser Phe Asn Lys Ser Ala Lys
            420                 425                 430

Gln Phe Ser Leu His Ile Met Asp Ser Gln Pro Gly Asp Ser Ala Thr
        435                 440                 445

```
Tyr Phe Cys Ala Ala Ser Thr Gly Asn Phe Asn Lys Phe Tyr Phe Gly
    450             455             460
Ser Gly Thr Lys Leu Asn Val Lys Pro Asn Ile Gln Asn Pro Glu Pro
465             470             475             480
Ala Val Tyr Gln Leu Lys Asp Pro Arg Ser Gln Asp Ser Thr Leu Cys
            485             490             495
Leu Phe Thr Asp Phe Asp Ser Gln Ile Asn Val Pro Lys Thr Met Glu
            500             505             510
Ser Gly Thr Phe Ile Thr Asp Lys Cys Val Leu Asp Met Lys Ala Met
            515             520             525
Asp Ser Lys Ser Asn Gly Ala Ile Ala Trp Ser Asn Gln Thr Ser Phe
530             535             540
Thr Cys Gln Asp Ile Phe Lys Glu Thr Asn Ala Thr Tyr Pro Ser Ser
545             550             555             560
Asp Val Pro Cys Asp Ala Thr Leu Thr Glu Lys Ser Phe Glu Thr Asp
            565             570             575
Met Asn Leu Asn Phe Gln Asn Leu Leu Val Ile Val Leu Arg Ile Leu
            580             585             590
Leu Leu Lys Val Ala Gly Phe Asn Leu Leu Met Thr Leu Arg Leu Trp
            595             600             605
Ser Ser
610
```